US010767185B2

(12) United States Patent
Lin et al.

(10) Patent No.: US 10,767,185 B2
(45) Date of Patent: Sep. 8, 2020

(54) METHOD OF PREPARING PORCINE CIRCOVIRUS TYPE 2 CAPSID PROTEIN AND PHARMACEUTICAL COMPOSITION COMPRISING SAME

(71) Applicant: AGRICULTURAL TECHNOLOGY RESEARCH INSTITUTE, HsinChu (TW)

(72) Inventors: Jiunn-Horng Lin, HsinChu (TW); Zeng-Weng Chen, HsinChu (TW); Jyh-Perng Wang, HsinChu (TW); Tzu-Ting Peng, HsinChu (TW); Huei-Yu Lee, HsinChu (TW); Weng-Zeng Huang, HsinChu (TW); Shih-Rong Wang, HsinChu (TW); Cheng-Yao Yang, HsinChu (TW)

(73) Assignee: AGRICULTURAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 15/778,062

(22) PCT Filed: Dec. 28, 2015

(86) PCT No.: PCT/CN2015/099172
§ 371 (c)(1),
(2) Date: May 22, 2018

(87) PCT Pub. No.: WO2017/113050
PCT Pub. Date: Jul. 6, 2017

(65) Prior Publication Data
US 2019/0078101 A1    Mar. 14, 2019

(51) Int. Cl.
*C12N 15/63* (2006.01)
*C12N 15/70* (2006.01)
(Continued)

(52) U.S. Cl.
CPC .......... *C12N 15/635* (2013.01); *A61K 38/162* (2013.01); *A61K 39/12* (2013.01);
(Continued)

(58) Field of Classification Search
None
See application file for complete search history.

(56) References Cited

U.S. PATENT DOCUMENTS 5,049,378 A * 9/1991 Campos ............... A61K 38/212
424/85.4
7,833,533 B2 * 11/2010 Grubman ............. A61K 38/212
424/216.1
(Continued)

FOREIGN PATENT DOCUMENTS

| CN | 101426522 A | 5/2009 |
| CN | 102839189 A | 12/2012 |

(Continued)

OTHER PUBLICATIONS

Dong et al. (Human Vaccines & Immunotherapeutics 9:4, 808-811; Apr. 2013).*

(Continued)

*Primary Examiner* — Shanon A. Foley
(74) *Attorney, Agent, or Firm* — Birch, Stewart, Kolasch & Birch, LLP

(57) ABSTRACT

The present invention provides a preparation method for PCV2 capsid protein and a pharmaceutical composition containing said capsid protein. The method of the present invention uses a novel arabinose-induced expression vector and thereby improves the synthesis efficiency of said PCV2 capsid protein. On the other hand, the present pharmaceutical composition combines said capsid protein and other favorable components at a proper ratio so that achieves excellent immune-inducing effects.

15 Claims, 11 Drawing Sheets

Figure 1:
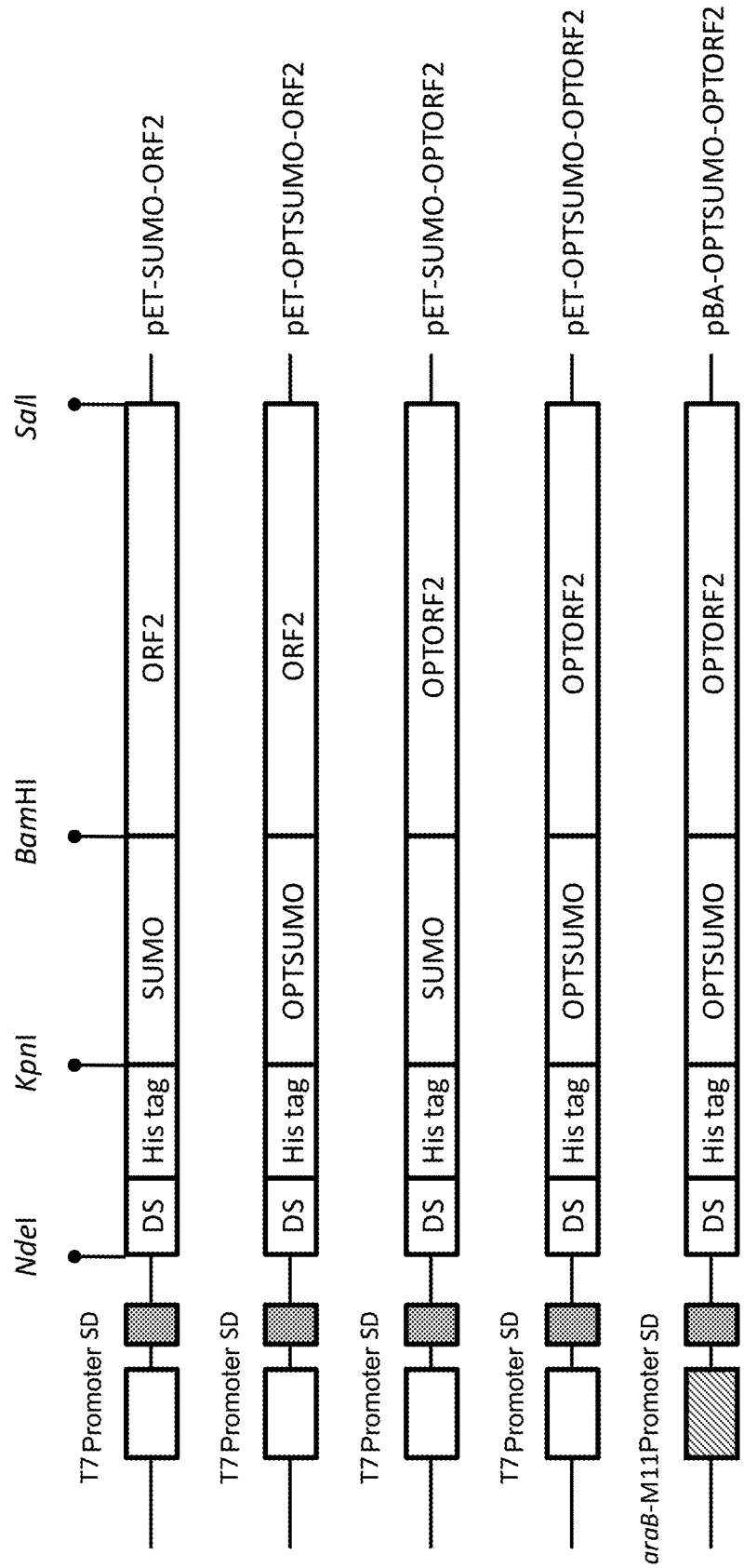

Specification includes a Sequence Listing.

(51) Int. Cl.
  *A61P 31/20* (2006.01)
  *A61K 38/16* (2006.01)
  *A61K 47/42* (2017.01)
  *A61K 39/12* (2006.01)
  *C07K 14/57* (2006.01)
  *A61K 39/00* (2006.01)
  *C07K 14/56* (2006.01)

(52) U.S. Cl.
  CPC .............. *A61K 47/42* (2013.01); *A61P 31/20* (2018.01); *A61K 2039/552* (2013.01); *A61K 2039/55522* (2013.01); *A61K 2039/55555* (2013.01); *A61K 2039/55566* (2013.01); *C07K 14/56* (2013.01); *C07K 14/57* (2013.01); *C12N 15/70* (2013.01); *C12N 2750/10033* (2013.01); *C12N 2750/10034* (2013.01)

(56) References Cited

U.S. PATENT DOCUMENTS

| | | | | |
|---|---|---|---|---|
| 2004/0101513 | A1* | 5/2004 | Zuckermann | A61K 39/12 424/93.2 |
| 2009/0017064 | A1* | 1/2009 | Wu | A61K 39/12 424/205.1 |
| 2011/0092391 | A1* | 4/2011 | Hayes | C07K 14/005 506/26 |

FOREIGN PATENT DOCUMENTS

| | | |
|---|---|---|
| CN | 103059124 A | 4/2013 |
| CN | 104371963 A | 2/2015 |
| JP | 2009-522310 A | 6/2009 |

OTHER PUBLICATIONS

Kontsek et al. (Acta Virologica. 1997; 41: 349-353).*
Alignment SEQ ID 1 with Geneseq database No. ADM47499 Jun. 2004.*
Alignment SEQ ID 2 with Geneseq database No. AWH42331 Apr. 2009.*
Alignment SEQ ID 3 with Geneseq database No. AOG50838 Dec. 2007.*
Definition of "synergism" provided by www.merriam-webster.com/dictionary/synergism Sep. 6, 2019.*
International Search Report (PCT/ISA/210) issued in PCT/CN2015/099172, dated Oct. 10, 2016.
Fuchizaki et al., "Synergistic Antiviral Effect of a Combination of Mouse Interferon-α and Interferon-γ on Mouse Hepatitis Virus", Journal of Medical Virology 69, pp. 188-194, 2003.
Prokulevich, "Interferon Veterinary Drugs", Bulletin of the Belarusian State University, Series 2, No. 3, pp. 51-55, 2011.

* cited by examiner

A

B

*: P<0.05; **: P<0.01.

SEQUENCE LISTING

```
<160> NUMBER OF SEQ ID NOS: 100

<210> SEQ ID NO 1
<211> LENGTH: 10
<212> TYPE: DNA
<213> ORGANISM: Enterobacteria phage t7

<400> SEQUENCE: 1
tttaacttta                                                          10

<210> SEQ ID NO 2
<211> LENGTH: 6
<212> TYPE: DNA
<213> ORGANISM: Escherichia coli

<400> SEQUENCE: 2 aggagg                                                               6
```

```
<210> SEQ ID NO 3
<211> LENGTH: 2
<212> TYPE: DNA
<213> ORGANISM: Escherichia coli

<400> SEQUENCE: 3 tg                                                                         2

<210> SEQ ID NO 4
<211> LENGTH: 89
<212> TYPE: DNA
<213> ORGANISM: Artificial Sequence
<220> FEATURE:
<223> OTHER INFORMATION: Synthetic: expression cassette

<400> SEQUENCE: 4
ggatcctacc tgacgctttt tatcgcaact tgctactgtt tctccatacc cgttttttttg         60 tttaacttta agaaggagga atacatatg                                            89

<210> SEQ ID NO 5
<211> LENGTH: 19
<212> TYPE: DNA
<213> ORGANISM: Artificial Sequence
<220> FEATURE:
<223> OTHER INFORMATION: Synthetic: primer

<400> SEQUENCE: 5
accagcgcac ttcggcagc                                                       19

<210> SEQ ID NO 6
<211> LENGTH: 29
<212> TYPE: DNA
<213> ORGANISM: Artificial Sequence
<220> FEATURE:
<223> OTHER INFORMATION: Synthetic: primer

<400> SEQUENCE: 6
aatacttaca gcgcacttct ttcgttttc                                            29

<210> SEQ ID NO 7
<211> LENGTH: 36
<212> TYPE: DNA
<213> ORGANISM: Artificial Sequence
<220> FEATURE:
<223> OTHER INFORMATION: Synthetic: primer

<400> SEQUENCE: 7
caatatggat ccatgacgta tccaaggagg cgtttc                                    36

<210> SEQ ID NO 8
<211> LENGTH: 44
<212> TYPE: DNA
<213> ORGANISM: Artificial Sequence
<220> FEATURE:
<223> OTHER INFORMATION: Synthetic: primer

<400> SEQUENCE: 8
gatatagtcg acttagggtt taagtgggggg gtctttaaga ttaa                          44

<210> SEQ ID NO 9
<211> LENGTH: 702
<212> TYPE: DNA
<213> ORGANISM: Porcine circovirus

<400> SEQUENCE: 9
```

```
atgacgtatc caaggaggcg tttccgcaga cgaagacacc gccccgcag ccatcttggc    60 cagatcctcc gccgccgccc ctggctcgtc caccccgcc accgttaccg ctggagaagg    120
aaaaatggca tcttcaacac ccgcctctcc cgcaccttcg gatatactgt aaaggctagc    180
acagtcagaa cgccctcctg ggcggtggac atgatgagat ttaatattaa cgactttgtt    240 ccccgggag gggggaccaa caaaatctct atacccttg aatactacag ataagaaag     300 gttaaggttg aattctggcc ctgctcccca atcacccagg gtgacagggg agtgggctcc    360
actgctgtta ttctagatga taactttgta actaaggcca cagccctaac ctatgacccc    420
tatgtaaact actcctcccg ccatacaatc ccccaaccct tctcctacca ctcccggtac    480
tttaccccca aacctgtcct tgattccact attgattact ccaaccaaa cagcaaaagg    540 aatcagattt ggctgaggct acaaacctcg gcaaatgtgg accacgtagg cctcggcact    600
gcgttcgaaa acagtaaata cgaccaggac tacaatatcc gtgtaactat gtatgtacaa    660
ttcagagaat ttaatcttaa agacccccca cttaaaccct aa                      702
```

<210> SEQ ID NO 10
<211> LENGTH: 73
<212> TYPE: DNA
<213> ORGANISM: Artificial Sequence
<220> FEATURE:
<223> OTHER INFORMATION: Synthetic: primer

<400> SEQUENCE: 10

```
atgacctacc cgcgtcgtcg tttccgtcgt cgtcgtcacc gtccgcgttc tcacctgggt    60
cagatcctgc gtc                                                      73
```

<210> SEQ ID NO 11
<211> LENGTH: 93
<212> TYPE: DNA
<213> ORGANISM: Artificial Sequence
<220> FEATURE:
<223> OTHER INFORMATION: Synthetic: primer

<400> SEQUENCE: 11

```
agacgggtgt tgaagatacc gtttttacga cgccaacggt aacggtgacg cgggtgaacc    60
agccacggac gacgacgcag atctgaccc agg                                 93
```

<210> SEQ ID NO 12
<211> LENGTH: 77
<212> TYPE: DNA
<213> ORGANISM: Artificial Sequence
<220> FEATURE:
<223> OTHER INFORMATION: Synthetic: primer

<400> SEQUENCE: 12

```
aacggtatct tcaacacccg tctgtctcgt accttcggtt acaccgttaa agcgtctacc    60
gttcgtaccc cgtcttg                                                  77
```

<210> SEQ ID NO 13
<211> LENGTH: 85
<212> TYPE: DNA
<213> ORGANISM: Artificial Sequence
<220> FEATURE:
<223> OTHER INFORMATION: Synthetic: primer

<400> SEQUENCE: 13

```
attttgttgg taccaccacc cggcggaacg aagtcgttga tgttgaaacg catcatgtca    60
accgcccaag acggggtacg aacgg                                         85
```

<210> SEQ ID NO 14
<211> LENGTH: 84
<212> TYPE: DNA
<213> ORGANISM: Artificial Sequence
<220> FEATURE:
<223> OTHER INFORMATION: Synthetic: primer

<400> SEQUENCE: 14
cgggtggtgg taccaacaaa atctctatcc cgttcgaata ctaccgtatc cgtaaagtta    60
aagttgagtt ttggccgtgc tctc    84

<210> SEQ ID NO 15
<211> LENGTH: 86
<212> TYPE: DNA
<213> ORGANISM: Artificial Sequence
<220> FEATURE:
<223> OTHER INFORMATION: Synthetic: primer

<400> SEQUENCE: 15
gtaacgaagt tgtcgtccag gataaccgcg gtagaaccaa caccacggtc accctgggtg    60
atcggagagc acggccaaaa ctcaac    86

<210> SEQ ID NO 16
<211> LENGTH: 90
<212> TYPE: DNA
<213> ORGANISM: Artificial Sequence
<220> FEATURE:
<223> OTHER INFORMATION: Synthetic: primer

<400> SEQUENCE: 16
gttatcctgg acgacaactt cgttaccaaa gcgaccgcgc tgacctacga cccgtacgtt    60
aactactctt ctcgtcacac catcccgcag    90

<210> SEQ ID NO 17
<211> LENGTH: 90
<212> TYPE: DNA
<213> ORGANISM: Artificial Sequence
<220> FEATURE:
<223> OTHER INFORMATION: Synthetic: primer

<400> SEQUENCE: 17
cggctggaag tagtcgatgg tagagtccag aaccggtttc ggggtgaagt aacgagagtg    60
gtaagagaac ggctgcggga tggtgtgacg    90

<210> SEQ ID NO 18
<211> LENGTH: 75
<212> TYPE: DNA
<213> ORGANISM: Artificial Sequence
<220> FEATURE:
<223> OTHER INFORMATION: Synthetic: primer

<400> SEQUENCE: 18
ctaccatcga ctacttccag ccgaactcta acgtaaccag atctggctg cgtctgcaga    60 cctctgcgaa cgttg    75

<210> SEQ ID NO 19
<211> LENGTH: 67
<212> TYPE: DNA
<213> ORGANISM: Artificial Sequence
<220> FEATURE:
<223> OTHER INFORMATION: Synthetic: primer

```
<400> SEQUENCE: 19
ctggtcgtat ttagagtttt cgaacgcggt acccagacca acgtggtcaa cgttcgcaga      60
ggtctgc                                                                67

<210> SEQ ID NO 20
<211> LENGTH: 64
<212> TYPE: DNA
<213> ORGANISM: Artificial Sequence
<220> FEATURE:
<223> OTHER INFORMATION: Synthetic: primer

<400> SEQUENCE: 20
cgttcgaaaa ctctaaatac gaccaggact acaacatccg tgttaccatg tacgttcagt      60
tccg                                                                   64

<210> SEQ ID NO 21
<211> LENGTH: 60
<212> TYPE: DNA
<213> ORGANISM: Artificial Sequence
<220> FEATURE:
<223> OTHER INFORMATION: Synthetic: primer

<400> SEQUENCE: 21
ttacggtttc agcggcgggt ctttcaggtt aaactcacgg aactgaacgt acatggtaac      60

<210> SEQ ID NO 22
<211> LENGTH: 36
<212> TYPE: DNA
<213> ORGANISM: Artificial Sequence
<220> FEATURE:
<223> OTHER INFORMATION: Synthetic: primer

<400> SEQUENCE: 22
gatataggat ccatgaccta cccgcgtcgt cgtttc                                36

<210> SEQ ID NO 23
<211> LENGTH: 36
<212> TYPE: DNA
<213> ORGANISM: Artificial Sequence
<220> FEATURE:
<223> OTHER INFORMATION: Synthetic: primer

<400> SEQUENCE: 23
caatatgtcg acttattacg gtttcagcgg cgggtc                                36

<210> SEQ ID NO 24
<211> LENGTH: 705
<212> TYPE: DNA
<213> ORGANISM: Porcine circovirus

<400> SEQUENCE: 24
atgacctacc cgcgtcgtcg tttccgtcgt cgtcgtcacc gtccgcgttc tcacctgggt      60
cagatcctgc gtcgtcgtcc gtggctggtt cacccgcgtc accgttaccg ttggcgtcgt     120
aaaaacggta tcttcaacac ccgtctgtct cgtaccttcg gttacaccgt taaagcgtct     180
accgttcgta ccccgtcttg gcggttgac atgatgcgtt tcaacatcaa cgacttcgtt     240
ccgccgggtg gtggtaccaa caaaatctct atcccgttcg aatactaccg tatccgtaaa     300
gttaaagttg agttttggcc gtgctctccg atcacccagg gtgaccgtgg tgttggttct     360
accgcggtta tcctggacga caacttcgtt accaaagcga ccgcgctgac ctacgacccg     420
tacgttaact actcttctcg tcacaccatc ccgcagccgt tctcttacca ctctcgttac     480
```

```
ttcaccccga aaccggttct ggactctacc atcgactact tccagccgaa ctctaaacgt      540
aaccagatct ggctgcgtct gcagacctct gcgaacgttg accacgttgg tctgggtacc      600
gcgttcgaaa actctaaata cgaccaggac tacaacatcc gtgttaccat gtacgttcag      660
ttccgtgagt taacctgaa agacccgccg ctgaaaccgt aataa                       705
```

<210> SEQ ID NO 25
<211> LENGTH: 37
<212> TYPE: DNA
<213> ORGANISM: Artificial Sequence
<220> FEATURE:
<223> OTHER INFORMATION: Synthetic: primer

<400> SEQUENCE: 25

```
gatataggta ccatgtcgga ctcagaagtc aatcaag                               37
```

<210> SEQ ID NO 26
<211> LENGTH: 36
<212> TYPE: DNA
<213> ORGANISM: Artificial Sequence
<220> FEATURE:
<223> OTHER INFORMATION: Synthetic: primer

<400> SEQUENCE: 26

```
caatatggat ccaccaccaa tctgttctct gtgagc                                36
```

<210> SEQ ID NO 27
<211> LENGTH: 58
<212> TYPE: DNA
<213> ORGANISM: Artificial Sequence
<220> FEATURE:
<223> OTHER INFORMATION: Synthetic: primer

<400> SEQUENCE: 27

```
atgagcgata gcgaagtgaa ccaagaagcg aaaccggaag tgaaaccgga agtgaaac        58
```

<210> SEQ ID NO 28
<211> LENGTH: 61
<212> TYPE: DNA
<213> ORGANISM: Artificial Sequence
<220> FEATURE:
<223> OTHER INFORMATION: Synthetic: primer

<400> SEQUENCE: 28

```
gctgccgtca ctaactttca ggttgatgtg ggtttccggt ttcacttccg gtttcacttc      60
c                                                                      61
```

<210> SEQ ID NO 29
<211> LENGTH: 62
<212> TYPE: DNA
<213> ORGANISM: Artificial Sequence
<220> FEATURE:
<223> OTHER INFORMATION: Synthetic: primer

<400> SEQUENCE: 29

```
cctgaaagtt agtgacggca gctctgaaat tttctttaag atcaaaaaga ccacgccgct      60
gc                                                                     62
```

<210> SEQ ID NO 30
<211> LENGTH: 55
<212> TYPE: DNA
<213> ORGANISM: Artificial Sequence
<220> FEATURE:

<223> OTHER INFORMATION: Synthetic: primer

<400> SEQUENCE: 30
tgccctgacg tttggcaaac gcttccatca ggcgacgcag cggcgtggtc ttttt    55

<210> SEQ ID NO 31
<211> LENGTH: 53
<212> TYPE: DNA
<213> ORGANISM: Artificial Sequence
<220> FEATURE:
<223> OTHER INFORMATION: Synthetic: primer

<400> SEQUENCE: 31
tttgccaaac gtcagggcaa ggaaatggat agtctgcgtt cctgtatga cgg    53

<210> SEQ ID NO 32
<211> LENGTH: 53
<212> TYPE: DNA
<213> ORGANISM: Artificial Sequence
<220> FEATURE:
<223> OTHER INFORMATION: Synthetic: primer

<400> SEQUENCE: 32
ttccggggtt tgatccgcct ggatgcgaat accgtcatac aggaaacgca gac    53

<210> SEQ ID NO 33
<211> LENGTH: 53
<212> TYPE: DNA
<213> ORGANISM: Artificial Sequence
<220> FEATURE:
<223> OTHER INFORMATION: Synthetic: primer

<400> SEQUENCE: 33
gcggatcaaa ccccggaaga cctggacatg aagacaacg acattatcga agc    53

<210> SEQ ID NO 34
<211> LENGTH: 46
<212> TYPE: DNA
<213> ORGANISM: Artificial Sequence
<220> FEATURE:
<223> OTHER INFORMATION: Synthetic: primer

<400> SEQUENCE: 34
gccgccgatt tgttcacggt gtgcttcgat aatgtcgttg tcttcc    46

<210> SEQ ID NO 35
<211> LENGTH: 37
<212> TYPE: DNA
<213> ORGANISM: Artificial Sequence
<220> FEATURE:
<223> OTHER INFORMATION: Synthetic: primer

<400> SEQUENCE: 35
caatatggta ccatgagcga tagcgaagtg aaccaag    37

<210> SEQ ID NO 36
<211> LENGTH: 31
<212> TYPE: DNA
<213> ORGANISM: Artificial Sequence
<220> FEATURE:
<223> OTHER INFORMATION: Synthetic: primer

<400> SEQUENCE: 36
gatataggat ccgccgccga tttgttcacg g    31

```
<210> SEQ ID NO 37
<211> LENGTH: 294
<212> TYPE: DNA
<213> ORGANISM: Escherichia coli

<400> SEQUENCE: 37
atgagcgata gcgaagtgaa ccaagaagcg aaaccggaag tgaaaccgga agtgaaaccg      60
gaaacccaca tcaacctgaa agttagtgac ggcagctctg aaatttctt taagatcaaa     120 aagaccacgc cgctgcgtcg cctgatggaa gcgtttgcca acgtcagggg caaggaaatg     180
gatagtctgc gtttcctgta tgacggtatt cgcatccagg cggatcaaac cccggaagac     240
ctggacatgg aagacaacga cattattgaa gcacaccgtg aacaaatcgg cggc           294

<210> SEQ ID NO 38
<211> LENGTH: 82
<212> TYPE: DNA
<213> ORGANISM: Artificial Sequence
<220> FEATURE:
<223> OTHER INFORMATION: Synthetic: primer

<400> SEQUENCE: 38
gatatacata tgaaaaaaaa attcgtatcg catcaccatc accatcacag cggtggtggt      60
accccagatc tgggtaccct gg                                              82

<210> SEQ ID NO 39
<211> LENGTH: 19
<212> TYPE: DNA
<213> ORGANISM: Artificial Sequence
<220> FEATURE:
<223> OTHER INFORMATION: Synthetic: primer

<400> SEQUENCE: 39
gctagttatt gctcagcgg                                                  19

<210> SEQ ID NO 40
<211> LENGTH: 18
<212> TYPE: DNA
<213> ORGANISM: Artificial Sequence
<220> FEATURE:
<223> OTHER INFORMATION: Synthetic: primer

<400> SEQUENCE: 40
aaaaaaaaat tcgtatcg                                                   18

<210> SEQ ID NO 41
<211> LENGTH: 18
<212> TYPE: DNA
<213> ORGANISM: Artificial Sequence
<220> FEATURE:
<223> OTHER INFORMATION: Synthetic: primer

<400> SEQUENCE: 41
catcaccatc accatcac                                                   18

<210> SEQ ID NO 42
<211> LENGTH: 6315
<212> TYPE: DNA
<213> ORGANISM: Artificial Sequence
<220> FEATURE:
<223> OTHER INFORMATION: Synthetic: plasmid

<400> SEQUENCE: 42
atccggatat agttcctcct ttcagcaaaa aaccccctcaa gacccgttta gaggccccaa     60
```

```
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttaggg tttaagtggg gggtctttaa gattaaattc tctgaattgt acatacatag    240
ttacacggat attgtagtcc tggtcgtatt tactgttttc gaacgcagtg ccgaggccta    300
cgtggtccac atttgccgag gtttgtagcc tcagccaaat ctgattcctt ttgctgtttg    360 gttgaagta atcaatagtg gaatcaagga caggtttggg ggtaaagtac cgggagtggt     420
aggagaaggg ttgggggatt gtatggcggg aggagtagtt tacataggg tcataggtta     480 gggctgtggc cttagttaca aagttatcat ctagaataac agcagtggag cccactcccc    540
tgtcaccctg ggtgattggg gagcagggcc agaattcaac cttaacctt cttattctgt     600 agtattcaaa gggtatagag attttgttgg tcccccctcc cggggaaca aagtcgttaa     660 tattaaatct catcatgtcc accgcccagg agggcgttct gactgtgcta gcctttacag    720
tatatccgaa ggtgcgggag aggcgggtgt tgaagatgcc attttccctt ctccagcggt    780
aacggtggcg ggggtggacg agccagggge ggcggcggag gatctggcca agatggctgc    840
gggggcggtg tcttcgtctg cggaaacgcc tccttggata cgtcatggat ccaccaccaa    900
tctgttctct gtgagcctca ataatatcgt tatcctccat gtccaaatct tcaggggtct    960
gatcagcttg aattctaata ccgtcgtaca agaatcttaa ggagtccatt tccttaccct   1020
gtcttttagc gaacgcttcc atcagccttc ttaaaggagt ggtcttttg atcttaaaga    1080 agatttctga agatccatcg gacacccttta aattgatgtg agtctcaggc ttgacttctg   1140
gcttgacctc tggcttagct tcttgattga cttctgagtc cgacatggta ccaccaccgc   1200
tgtgatggtg atggtgatgc gatacgaatt ttttttcat atgtatatct ccttcttaaa    1260
gttaaacaaa attatttcta gaggggaatt gttatccgct cacaattccc ctatagtgag   1320
tcgtattaat ttcgcgggat cgagatcgat ctcgatcctc tacgccggac gcatcgtggc   1380
cggcatcacc ggcgccacag gtgcggttgc tggcgcctat atcgccgaca tcaccgatgg   1440
ggaagatcgg gctcgccact tcgggctcat gagcgcttgt ttcggcgtgg gtatggtggc   1500
aggccccgtg gccgggggac tgttgggcgc catctccttg catgcaccat tccttgcggc   1560
ggcggtgctc aacggcctca acctactact gggctgcttc ctaatgcagg agtcgcataa   1620
gggagagcgt cgagatcccg gacaccatcg aatggcgcaa aacctttcgc ggtatggcat   1680
gatagcgccc ggaagagagt caattcaggg tggtgaatgt gaaaccagta acgttatacg   1740
atgtcgcaga gtatgccggt gtctcttatc agaccgtttc ccgcgtggtg aaccaggcca   1800
gccacgtttc tgcgaaaacg cgggaaaaag tggaagcggc gatggcggag ctgaattaca   1860
ttcccaaccg cgtggcacaa caactggcgg caaacagtc gttgctgatt ggcgttgcca    1920
cctccagtct ggccctgcac gcgccgtcgc aaattgtcgc ggcgattaaa tctcgcgccg   1980
atcaactggg tgccagcgtg gtggtgtcga tggtagaacg aagcggcgtc gaagcctgta   2040
aagcggcggt gcacaatctt ctcgcgcaac gcgtcagtgg gctgatcatt aactatccgc   2100
tggatgacca ggatgccatt gctgtggaag ctgcctgcac taatgttccg gcgttatttc   2160
ttgatgtctc tgaccagaca cccatcaaca gtattatttt ctcccatgaa gacggtacgc   2220
gactgggcgt ggagcatctg gtcgcattgg gtcaccagca atcgcgctg ttagcgggcc    2280 cattaagttc tgtctcggcg cgtctgcgtc tggctggctg cataaatat ctcactcgca    2340 atcaaattca gccgatagcg gaacgggaag gcgactggag tgccatgtcc ggttttcaac   2400
aaaccatgca aatgctgaat gagggcatcg ttcccactgc gatgctggtt gccaacgatc   2460
```

```
agatggcgct gggcgcaatg cgcgccatta ccgagtccgg gctgcgcgtt ggtgcggaca   2520
tctcggtagt gggatacgac gataccgaag acagctcatg ttatatcccg ccgttaacca   2580
ccatcaaaca ggattttcgc ctgctggggc aaaccagcgt ggaccgcttg ctgcaactct   2640
ctcagggcca ggcggtgaag ggcaatcagc tgttgcccgt ctcactggtg aaagaaaaa   2700 ccaccctggc gcccaatacg caaaccgcct ctccccgcgc gttggccgat tcattaatgc   2760
agctggcacg acaggtttcc cgactggaaa gcgggcagtg agcgcaacgc aattaatgta   2820
agttagctca ctcattaggc accgggatct cgaccgatgc ccttgagagc cttcaaccca   2880
gtcagctcct tccggtgggc gcggggcatg actatcgtcg ccgcacttat gactgtcttc   2940
tttatcatgc aactcgtagg acaggtgccg gcagcgctct gggtcatttt cggcgaggac   3000
cgctttcgct ggagcgcgac gatgatcggc ctgtcgcttg cggtattcgg aatcttgcac   3060
gccctcgctc aagccttcgt cactggtccc gccaccaaac gtttcggcga agcaggcc    3120 attatcgccg gcatggcggc cccacggggtg cgcatgatcg tgctcctgtc gttgaggacc   3180
cggctaggct ggcggggttg ccttactggt tagcagaatg aatcaccgat acgcgagcga   3240
acgtgaagcg actgctgctg caaaacgtct gcgacctgag caacaacatg aatggtcttc   3300
ggtttccgtg tttcgtaaag tctggaaacg cggaagtcag cgccctgcac cattatgttc   3360
cggatctgca tcgcaggatg ctgctggcta ccctgtggaa cacctacatc tgtattaacg   3420
aagcgctggc attgaccctg agtgattttt ctctggtccc gccgcatcca taccgccagt   3480
tgtttaccct cacaacgttc cagtaaccgg gcatgttcat catcagtaac ccgtatcgtg   3540
agcatcctct ctcgtttcat cggtatcatt accccccatga acagaaatcc cccttacacg   3600
gaggcatcag tgaccaaaca ggaaaaaacc gcccttaaca tggcccgctt tatcagaagc   3660
cagacattaa cgcttctgga gaaactcaac gagctggacg cggatgaaca ggcagacatc   3720
tgtgaatcgc ttcacgacca cgctgatgag ctttaccgca gctgcctcgc gcgtttcggt   3780
gatgacggtg aaaacctctg acacatgcag ctcccggaga cggtcacagc ttgtctgtaa   3840
gcggatgccg ggagcagaca gcccgtcag ggcgcgtcag cgggtgttgg cgggtgtcgg   3900
ggcgcagcca tgacccagtc acgtagcgat agcggagtgt atactggctt aactatgcgg   3960
catcagagca gattgtactg agagtgcacc atatatgcgg tgtgaaatac cgcacagatg   4020
cgtaaggaga aaataccgca tcaggcgctc ttccgcttcc tcgctcactg actcgctgcg   4080
ctcggtcgtt cggctgcggc gagcggtatc agctcactca aaggcggtaa tacggttatc   4140
cacagaatca ggggataacg caggaaagaa catgtgagca aaaggccagc aaaaggccag   4200
gaaccgtaaa aaggccgcgt tgctggcgtt tttccatagg ctccgccccc ctgacgagca   4260
tcacaaaaat cgacgctcaa gtcagaggtg gcgaaacccg acaggactat aaagatacca   4320
ggcgtttccc cctggaagct ccctcgtgcg ctctcctgtt ccgaccctgc cgcttaccgg   4380
atacctgtcc gcctttctcc cttcgggaag cgtggcgctt tctcatagct cacgctgtag   4440
gtatctcagt tcggtgtagg tcgttcgctc caagctgggc tgtgtgcacg aaccccccgt   4500
tcagcccgac cgctgcgcct tatccggtaa ctatcgtctt gagtccaacc cggtaagaca   4560
cgacttatcg ccactggcag cagccactgg taacaggatt agcagagcga ggtatgtagg   4620
cggtgctaca gagttcttga agtggtggcc taactacggc tacactagaa ggacagtatt   4680
tggtatctgc gctctgctga agccagttac cttcggaaaa agagttggta gctcttgatc   4740
cggcaaacaa accaccgctg gtagcggtgg tttttttgtt tgcaagcagc agattacgcg   4800
```

| | | |
|---|---|---|
| cagaaaaaaa ggatctcaag aagatccttt gatcttttct acggggtctg acgctcagtg | 4860 | |
| gaacgaaaac tcacgttaag ggattttggt catgaacaat aaaactgtct gcttacataa | 4920 | |
| acagtaatac aagggggtgtt atgagccata ttcaacggga aacgtcttgc tctaggccgc | 4980 | |
| gattaaattc caacatggat gctgatttat atgggtataa atgggctcgc gataatgtcg | 5040 | |
| ggcaatcagg tgcgacaatc tatcgattgt atgggaagcc cgatgcgcca gagttgtttc | 5100 | |
| tgaaacatgg caaaggtagc gttgccaatg atgttacaga tgagatggtc agactaaact | 5160 | |
| ggctgacgga atttatgcct cttccgacca tcaagcattt tatccgtact cctgatgatg | 5220 | |
| catggttact caccactgcg atccccggga aaacagcatt ccaggtatta gaagaatatc | 5280 | |
| ctgattcagg tgaaaatatt gttgatgcgc tggcagtgtt cctgcgccgg ttgcattcga | 5340 | |
| ttcctgtttg taattgtcct tttaacagcg atcgcgtatt tcgtctcgct caggcgcaat | 5400 | |
| cacgaatgaa taacggtttg gttgatgcga gtgattttga tgacgagcgt aatggctggc | 5460 | |
| ctgttgaaca gtctggaaa gaaatgcata aacttttgcc attctcaccg gattcagtcg | 5520 | |
| tcactcatgg tgatttctca cttgataacc ttatttttga cgaggggaaa ttaataggtt | 5580 | |
| gtattgatgt tggacgagtc ggaatcgcag accgatacca ggatcttgcc atcctatgga | 5640 | |
| actgcctcgg tgagttttct ccttcattac agaaacggct ttttcaaaaa tatggtattg | 5700 | |
| ataatcctga tatgaataaa ttgcagtttc atttgatgct cgatgagttt ttctaagaat | 5760 | |
| taattcatga gcggatacat atttgaatgt atttagaaaa ataaacaaat aggggttccg | 5820 | |
| cgcacatttc cccgaaaagt gccacctgaa attgtaaacg ttaatatttt gttaaaattc | 5880 | |
| gcgttaaatt tttgttaaat cagctcattt tttaaccaat aggccgaaat cggcaaaatc | 5940 | |
| ccttataaat caaaagaata accgagata gggttgagtg ttgttccagt ttggaacaag | 6000 | |
| agtccactat taaagaacgt ggactccaac gtcaaagggc gaaaaaccgt ctatcagggc | 6060 | |
| gatggcccac tacgtgaacc atcaccctaa tcaagttttt tggggtcgag gtgccgtaaa | 6120 | |
| gcactaaatc ggaaccctaa agggagcccc cgatttagag cttgacgggg aaagccggcg | 6180 | |
| aacgtggcga gaaaggaagg gaagaaagcg aaaggagcgg cgctagggc gctggcaagt | 6240 | |
| gtagcggtca cgctgcgcgt aaccaccaca cccgccgcgc ttaatgcgcc gctacagggc | 6300 | |
| gcgtcccatt cgcca | 6315 | |

<210> SEQ ID NO 43
<211> LENGTH: 6315
<212> TYPE: DNA
<213> ORGANISM: Artificial Sequence
<220> FEATURE:
<223> OTHER INFORMATION: Synthetic: plasmid

<400> SEQUENCE: 43

| | | |
|---|---|---|
| atccggatat agttcctcct ttcagcaaaa aaccccctcaa gacccgttta gaggccccaa | 60 | |
| ggggttatgc tagttattgc tcagcggtgg cagcagccaa ctcagcttcc tttcgggctt | 120 | |
| tgttagcagc cggatctcag tggtggtggt ggtggtgctc gagtgcggcc gcaagcttgt | 180 | |
| cgacttaggg tttaagtggg gggtctttaa gattaaattc tctgaattgt acatacatag | 240 | |
| ttacacggat attgtagtcc tggtcgtatt tactgttttc gaacgcagtg ccgaggccta | 300 | |
| cgtggtccac atttgccgag gtttgtagcc tcagccaaat ctgattcctt tgctgtttg | 360 | |
| gttggaagta atcaatagtg gaatcaagga caggtttggg ggtaaagtac cgggagtggt | 420 | |
| aggagaaggg ttgggggatt gtatggcggg aggagtagtt tacataggggt cataggtta | 480 | |
| gggctgtggc cttagttaca aagttatcat ctagaataac agcagtggag cccactcccc | 540 | |

```
tgtcaccctg ggtgattggg gagcagggcc agaattcaac cttaacctttt cttattctgt    600 agtattcaaa gggtatagag attttgttgg tccccctcc cggggaaca aagtcgttaa       660 tattaaatct catcatgtcc accgcccagg agggcgttct gactgtgcta gcctttacag    720
tatatccgaa ggtgcgggag aggcgggtgt tgaagatgcc attttccctt ctccagcggt    780
aacggtggcg ggggtggacg agccagggcc ggcggcggag gatctggcca agatggctgc    840
gggggcggtg tcttcgtctg cggaaacgcc tccttggata cgtcatggat ccgccgccga    900
tttgttcacg gtgtgcttcg ataatgtcgt tgtcttccat gtccaggtct tccggggttt    960
gatccgcctg gatgcgaata ccgtcataca ggaaacgcag actatccatt tccttgccct   1020
gacgtttggc aaacgcttcc atcaggcgac gcagcggcgt ggtcttttttg atcttaaaga  1080 aaatttcaga gctgccgtca ctaactttca ggttgatgtg ggtttccggt ttcacttccg   1140
gtttcacttc cggtttcgct tcttggttca cttcgctatc gctcatggta ccaccaccgc   1200
tgtgatggtg atggtgatgc gatacgaatt tttttttcat atgtatatct ccttcttaaa   1260
gttaaacaaa attatttcta gagggaatt gttatccgct cacaattccc ctatagtgag    1320
tcgtattaat ttcgcgggat cgagatcgat ctcgatcctc tacgccggac gcatcgtggc   1380
cggcatcacc ggcgccacag gtgcggttgc tggcgcctat atcgccgaca tcaccgatgg   1440
ggaagatcgg gctcgccact tcgggctcat gagcgcttgt ttcggcgtgg gtatggtggc   1500
aggccccgtg gccggggac tgttgggcgc catctccttg catgcaccat tccttgcggc    1560
ggcggtgctc aacggcctca acctactact gggctgcttc ctaatgcagg agtcgcataa   1620
gggagagcgt cgagatcccg gacaccatcg aatggcgcaa aacctttcgc ggtatggcat   1680
gatagcgccc ggaagagagt caattcaggg tggtgaatgt gaaaccagta acgttatacg   1740
atgtcgcaga gtatgccggt gtctcttatc agaccgtttc ccgcgtggtg aaccaggcca   1800
gccacgtttc tgcgaaaacg cgggaaaaag tggaagcggc gatggcggag ctgaattaca   1860
ttcccaaccg cgtggcacaa caactggcgg gcaaacagtc gttgctgatt ggcgttgcca   1920
cctccagtct ggccctgcac gcgccgtcgc aaattgtcgc ggcgattaaa tctcgcgccg   1980
atcaactggg tgccagcgtg gtggtgtcga tggtagaacg aagcggcgtc gaagcctgta   2040
aagcggcggt gcacaatctt ctcgcgcaac gcgtcagtgg gctgatcatt aactatccgc   2100
tggatgacca ggatgccatt gctgtggaag ctgcctgcac taatgttccg gcgttatttc   2160
ttgatgtctc tgaccagaca cccatcaaca gtattattttt ctcccatgaa gacggtacgc  2220
gactgggcgt ggagcatctg gtcgcattgg gtcaccagca atcgcgctg ttagcgggcc    2280 cattaagttc tgtctcggcg cgtctgcgtc tggctggctg gcataaatat ctcactcgca   2340
atcaaattca gccgatagcg gaacgggaag gcgactggag tgccatgtcc ggttttcaac   2400
aaaccatgca aatgctgaat gagggcatcg ttcccactgc gatgctggtt gccaacgatc   2460
agatggcgct gggcgcaatg cgcgccatta ccgagtccgg gctgcgcgtt ggtgcggaca   2520
tctcggtagt gggatacgac gataccgaag acagctcatg ttatatcccg ccgttaacca   2580
ccatcaaaca ggattttcgc ctgctggggc aaaccagcgt ggaccgcttg ctgcaactct   2640
ctcagggcca ggcggtgaag gcaatcagc tgttgcccgt ctcactggtg aaagaaaaaa   2700
ccaccctggc gcccaatacg caaaccgcct ctccccgcgc gttggccgat tcattaatgc   2760
agctggcacg acaggtttcc cgactggaaa gcgggcagtg agcgcaacgc aattaatgta   2820
agttagctca ctcattaggc accgggatct cgaccgatgc ccttgagagc cttcaaccca   2880
```

```
gtcagctcct tccggtgggc gcggggcatg actatcgtcg ccgcacttat gactgtcttc   2940
tttatcatgc aactcgtagg acaggtgccg cagcgctct gggtcatttt cggcgaggac    3000
cgctttcgct ggagcgcgac gatgatcggc ctgtcgcttg cggtattcgg aatcttgcac   3060
gccctcgctc aagccttcgt cactggtccc gccaccaaac gtttcggcga aagcaggcc    3120 attatcgccg gcatggcggc cccacggtg cgcatgatcg tgctcctgtc gttgaggacc    3180
cggctaggct ggcggggttg ccttactggt tagcagaatg aatcaccgat acgcgagcga   3240
acgtgaagcg actgctgctg caaaacgtct gcgacctgag caacaacatg aatggtcttc   3300
ggtttccgtg tttcgtaaag tctggaaacg cggaagtcag cgccctgcac cattatgttc   3360
cggatctgca tcgcaggatg ctgctggcta ccctgtggaa cacctacatc tgtattaacg   3420
aagcgctggc attgaccctg agtgatttt tctctggtccc gccgcatcca taccgccagt   3480
tgtttaccct cacaacgttc cagtaaccgg gcatgttcat catcagtaac ccgtatcgtg   3540
agcatcctct ctcgtttcat cggtatcatt accccccatga acagaaatcc cccttacacg   3600
gaggcatcag tgaccaaaca ggaaaaaacc gcccttaaca tggcccgctt tatcagaagc   3660
cagacattaa cgcttctgga gaaactcaac gagctggacg cggatgaaca ggcagacatc   3720
tgtgaatcgc ttcacgacca cgctgatgag ctttaccgca gctgcctcgc gcgtttcggt   3780
gatgacggtg aaaacctctg acacatgcag ctcccggaga cggtcacagc ttgtctgtaa   3840
gcggatgccg ggagcagaca agcccgtcag ggcgcgtcag cgggtgttgg cgggtgtcgg   3900
ggcgcagcca tgacccagtc acgtagcgat agcggagtgt atactggctt aactatgcgg   3960
catcagagca gattgtactg agagtgcacc atatatgcgg tgtgaaatac cgcacagatg   4020
cgtaaggaga aaataccgca tcaggcgctc ttccgcttcc tcgctcactg actcgctgcg   4080
ctcggtcgtt cggctgcggc gagcggtatc agctcactca aaggcggtaa tacggttatc   4140
cacagaatca ggggataacg caggaaagaa catgtgagca aaaggccagc aaaaggccag   4200
gaaccgtaaa aaggccgcgt tgctggcgtt tttccatagg ctccgccccc ctgacgagca   4260
tcacaaaaat cgacgctcaa gtcagaggtg gcgaaacccg acaggactat aaagatacca   4320
ggcgtttccc cctggaagct ccctcgtgcg ctctcctgtt ccgaccctgc cgcttaccgg   4380
atacctgtcc gcctttctcc cttcgggaag cgtggcgctt tctcatagct cacgctgtag   4440
gtatctcagt tcggtgtagg tcgttcgctc caagctgggc tgtgtgcacg aaccccccgt   4500
tcagcccgac cgctgcgcct tatccggtaa ctatcgtctt gagtccaacc cggtaagaca   4560
cgacttatcg ccactggcag cagccactgg taacaggatt agcagagcga ggtatgtagg   4620
cggtgctaca gagttcttga agtggtggcc taactacggc tacactagaa ggacagtatt   4680
tggtatctgc gctctgctga agccagttac cttcggaaaa agagttggta gctcttgatc   4740
cggcaaacaa accaccgctg gtagcggtgg tttttttgtt tgcaagcagc agattacgcg   4800
cagaaaaaaa ggatctcaag aagatccttt gatcttttct acggggtctg acgctcagtg   4860
gaacgaaaac tcacgttaag ggattttggt catgaacaat aaaactgtct gcttacataa   4920
acagtaatac aagggggtgtt atgagccata ttcaacggga acgtcttgc tctaggccgc    4980 gattaaattc caacatggat gctgatttat atgggtataa atgggctcgc gataatgtcg   5040
ggcaatcagg tgcgacaatc tatcgattgt atgggaagcc cgatgcgcca gagttgtttc   5100
tgaaacatgg caaaggtagc gttgccaatg atgttacaga tgagatggtc agactaaact   5160
ggctgacgga atttatgcct cttccgacca tcaagcattt tatccgtact cctgatgatg   5220
catggttact caccactgcg atccccggga aaacagcatt ccaggtatta gaagaatatc   5280
```

```
ctgattcagg tgaaaatatt gttgatgcgc tggcagtgtt cctgcgccgg ttgcattcga      5340
ttcctgtttg taattgtcct tttaacagcg atcgcgtatt tcgtctcgct caggcgcaat      5400
cacgaatgaa taacggtttg gttgatgcga gtgattttga tgacgagcgt aatggctggc      5460
ctgttgaaca agtctggaaa gaaatgcata aacttttgcc attctcaccg gattcagtcg      5520
tcactcatgg tgatttctca cttgataacc ttattttga cgaggggaaa ttaataggtt       5580
gtattgatgt tggacgagtc ggaatcgcag accgatacca ggatcttgcc atcctatgga      5640
actgcctcgg tgagttttct ccttcattac agaaacggct ttttcaaaaa tatggtattg      5700
ataatcctga tatgaataaa ttgcagtttc atttgatgct cgatgagttt ttctaagaat      5760
taattcatga gcggatacat atttgaatgt atttagaaaa ataaacaaat aggggttccg      5820
cgcacatttc cccgaaaagt gccacctgaa attgtaaacg ttaatatttt gttaaaattc      5880
gcgttaaatt tttgttaaat cagctcattt tttaaccaat aggccgaaat cggcaaaatc      5940
ccttataaat caaagaata gaccgagata ggttgagtg ttgttccagt ttggaacaag        6000
agtccactat taaagaacgt ggactccaac gtcaaagggc gaaaaaccgt ctatcagggc      6060
gatggcccac tacgtgaacc atcaccctaa tcaagttttt tggggtcgag gtgccgtaaa      6120
gcactaaatc ggaaccctaa agggagcccc cgatttagag cttgacgggg aaagccggcg      6180
aacgtggcga aaaggaagg gaagaaagcg aaaggagcgg cgctagggc gctggcaagt        6240 gtagcggtca cgctgcgcgt aaccaccaca cccgccgcgc ttaatgcgcc gctacagggc      6300
gcgtcccatt cgcca                                                      6315

<210> SEQ ID NO 44
<211> LENGTH: 6318
<212> TYPE: DNA
<213> ORGANISM: Artificial Sequence
<220> FEATURE:
<223> OTHER INFORMATION: Synthetic: plasmid

<400> SEQUENCE: 44
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacttatta cggtttcagc ggcgggtctt tcaggttaaa ctcacggaac tgaacgtaca     240
tggtaacacg gatgttgtag tcctggtcgt atttagagtt ttcgaacgcg gtacccagac     300
caacgtggtc aacgttcgca gaggtctgca gacgcagcca gatctggtta cgtttagagt     360
tcggctggaa gtagtcgatg gtagagtcca gaaccggttt cggggtgaag taacgagagt     420
ggtaagagaa cggctgcggg atggtgtgac gagaagagta gttaacgtac gggtcgtagg     480
tcagcgcggt cgctttggta acgaagttgt cgtccaggat aaccgcggta gaaccaacac     540
cacggtcacc ctgggtgatc ggagagcacg gccaaaactc aactttaact ttacggatac     600
ggtagtattc gaacgggata gagattttgt tggtaccacc acccggcgga acgaagtcgt     660
tgatgttgaa acgcatcatg tcaaccgccc aagacgggt acgaacggta gacgctttaa     720
cggtgtaacc gaaggtacga gacagacggg tgttgaagat accgttttta cgacgccaac    780
ggtaacggtg acgcgggtga accagccacg gacgacgacg caggatctga cccaggtgag     840
aacgcggacg gtgacgacga cgacggaaac gacgacgcgg gtaggtcatg gatccaccac    900
caatctgttc tctgtgagcc tcaataatat cgttatcctc catgtccaaa tcttcagggg    960
```

-continued

```
tctgatcagc ttgaattcta ataccgtcgt acaagaatct taaggagtcc atttccttac    1020 cctgtcttt  agcgaacgct tccatcagcc ttcttaaagg agtggtcttt ttgatcttaa    1080
agaagatttc tgaagatcca tcggacacct ttaaattgat gtgagtctca ggcttgactt    1140
ctggcttgac ctctggctta gcttcttgat tgacttctga gtccgacatg gtaccaccac    1200
cgctgtgatg gtgatggtga tgcgatacga atttttttt  catatgtata tctccttctt    1260
aaagttaaac aaaattattt ctagagggga attgttatcc gctcacaatt ccctatagt     1320 gagtcgtatt aatttcgcgg gatcgagatc gatctcgatc tctacgccg  gacgcatcgt    1380 ggccggcatc accggcgcca caggtgcggt tgctggcgcc tatatcgccg acatcaccga    1440
tggggaagat cgggctcgcc acttcgggct catgagcgct tgtttcggcg tgggtatggt    1500
ggcaggcccc gtggccgggg gactgttggg cgccatctcc ttgcatgcac cattccttgc    1560
ggcggcggtg ctcaacggcc tcaacctact actgggctgc ttcctaatgc aggagtcgca    1620
taagggagag cgtcgagatc ccggacacca tcgaatggcg caaaaccttt cgcggtatgg    1680
catgatagcg cccggaagag agtcaattca gggtggtgaa tgtgaaacca gtaacgttat    1740
acgatgtcgc agagtatgcc ggtgtctctt atcagaccgt ttcccgcgtg gtgaaccagg    1800
ccagccacgt ttctgcgaaa acgcgggaaa aagtggaagc ggcgatggcg gagctgaatt    1860
acattcccaa ccgcgtggca caacaactgg cgggcaaaca gtcgttgctg attggcgttg    1920
ccacctccag tctggccctg cacgcgccgt cgcaaattgt cgcggcgatt aaatctcgcg    1980
ccgatcaact gggtgccagc gtggtggtgt cgatggtaga acgaagcggc gtcgaagcct    2040
gtaaagcggc ggtgcacaat cttctcgcgc aacgcgtcag tgggctgatc attaactatc    2100
cgctggatga ccaggatgcc attgctgtgg aagctgcctg cactaatgtt ccggcgttat    2160
ttcttgatgt ctctgaccag acacccatca acagtattat tttctcccat gaagacggta    2220
cgcgactggg cgtggagcat ctggtcgcat tgggtcacca gcaaatcgcg ctgttagcgg    2280
gcccattaag ttctgtctcg gcgcgtctgc gtctggctgg ctggcataaa tatctcactc    2340
gcaatcaaat tcagccgata gcggaacggg aaggcgactg gagtgccatg tccggttttc    2400
aacaaaccat gcaaatgctg aatgagggca tcgttcccac tgcgatgctg gttgccaacg    2460
atcagatggc gctgggcgca atgcgcgcca ttaccgagtc cgggctgcgc gttggtgcgg    2520
acatctcggt agtgggatac gacgataccg aagacagctc atgttatatc ccgccgttaa    2580
ccaccatcaa acaggatttt cgcctgctgg ggcaaaccag cgtggaccgc ttgctgcaac    2640
tctctcaggg ccaggcggtg aagggcaatc agctgttgcc cgtctcactg gtgaaaagaa    2700
aaaccaccct ggcgcccaat acgcaaaccg cctctccccg cgcgttggcc gattcattaa    2760
tgcagctggc acgacaggtt tcccgactgg aaagcgggca gtgagcgcaa cgcaattaat    2820
gtaagttagc tcactcatta ggcaccggga tctcgaccga tgcccttgag agccttcaac    2880
ccagtcagct ccttccggtg ggcgcgggc  atgactatcg tcgccgcact tatgactgtc    2940
ttctttatca tgcaactcgt aggacaggtg ccggcagcgc tctgggtcat tttcggcgag    3000
gaccgctttc gctggagcgc gacgatgatc ggcctgtcgc ttgcggtatt cggaatcttg    3060
cacgccctcg ctcaagcctt cgtcactggt cccgccacca aacgtttcgg cgagaagcag    3120
gccattatcg ccggcatggc ggccccacgg gtgcgcatga tcgtgctcct gtcgttgagg    3180
acccggctag gctggcgggg ttgccttact ggttagcaga atgaatcacc gatacgcgag    3240
cgaacgtgaa gcgactgctg ctgcaaaacg tctgcgacct gagcaacaac atgaatggtc    3300
ttcggtttcc gtgtttcgta aagtctggaa acgcggaagt cagcgccctg caccattatg    3360
```

-continued

```
ttccggatct gcatcgcagg atgctgctgg ctaccctgtg gaacacctac atctgtatta    3420
acgaagcgct ggcattgacc ctgagtgatt tttctctggt cccgccgcat ccataccgcc    3480
agttgtttac cctcacaacg ttccagtaac cgggcatgtt catcatcagt aacccgtatc    3540
gtgagcatcc tctctcgttt catcggtatc attaccccca tgaacagaaa tcccccttac    3600
acggaggcat cagtgaccaa acaggaaaaa accgccctta acatggcccg ctttatcaga    3660
agccagacat taacgcttct ggagaaactc aacgagctgg acgcggatga acaggcagac    3720
atctgtgaat cgcttcacga ccacgctgat gagctttacc gcagctgcct cgcgcgtttc    3780
ggtgatgacg gtgaaaacct ctgacacatg cagctcccgg agacggtcac agcttgtctg    3840
taagcggatg ccgggagcag acaagcccgt cagggcgcgt cagcgggtgt tggcgggtgt    3900
cggggcgcag ccatgaccca gtcacgtagc gatagcggag tgtatactgg cttaactatg    3960
cggcatcaga gcagattgta ctgagagtgc accatatatg cggtgtgaaa taccgcacag    4020
atgcgtaagg agaaaatacc gcatcaggcg ctcttccgct tcctcgctca ctgactcgct    4080
gcgctcggtc gttcggctgc ggcgagcggt atcagctcac tcaaaggcgg taatacggtt    4140
atccacagaa tcaggggata acgcaggaaa gaacatgtga gcaaaaggcc agcaaaaggc    4200
caggaaccgt aaaaaggccg cgttgctggc gtttttccat aggctccgcc cccctgacga    4260
gcatcacaaa aatcgacgct caagtcagag gtggcgaaac ccgacaggac tataaagata    4320
ccaggcgttt ccccctggaa gctccctcgt gcgctctcct gttccgaccc tgccgcttac    4380
cggatacctg tccgcctttc tcccttcggg aagcgtggcg ctttctcata gctcacgctg    4440
taggtatctc agttcggtgt aggtcgttcg ctccaagctg ggctgtgtgc acgaaccccc    4500
cgttcagccc gaccgctgcg ccttatccgg taactatcgt cttgagtcca acccggtaag    4560
acacgactta tcgccactgg cagcagccac tggtaacagg attagcagag cgaggtatgt    4620
aggcggtgct acagagttct tgaagtggtg gcctaactac ggctacacta aggacagt     4680 atttggtatc tgcgctctgc tgaagccagt taccttcgga aaaagagttg gtagctcttg    4740
atccggcaaa caaaccaccg ctggtagcgg tggtttttttt gtttgcaagc agcagattac    4800
gcgcagaaaa aaaggatctc aagaagatcc tttgatcttt tctacggggt ctgacgctca    4860
gtggaacgaa aactcacgtt aagggatttt ggtcatgaac aataaaactg tctgcttaca    4920
taaacagtaa tacaagggt gttatgagcc atattcaacg ggaaacgtct tgctctaggc    4980
cgcgattaaa ttccaacatg gatgctgatt tatatgggta taaatgggct cgcgataatg    5040
tcgggcaatc aggtgcgaca atctatcgat tgtatgggaa gcccgatgcg ccagagttgt    5100
ttctgaaaca tggcaaaggt agcgttgcca atgatgttac agatgagatg gtcagactaa    5160
actggctgac ggaatttatg cctcttccga ccatcaagca ttttatccgt actcctgatg    5220
atgcatggtt actcaccact gcgatccccg ggaaaacagc attccaggta ttagaagaat    5280
atcctgattc aggtgaaaat attgttgatg cgctggcagt gttcctgcgc cggttgcatt    5340
cgattcctgt ttgtaattgt ccttttaaca gcgatcgcgt atttcgtctc gctcaggcgc    5400
aatcacgaat gaataacggt ttggttgatg cgagtgattt tgatgacgag cgtaatggct    5460
ggcctgttga acaagtctgg aaagaaatgc ataaactttt gccattctca ccggattcag    5520
tcgtcactca tggtgatttc tcacttgata accttatttt tgacgagggg aaattaatag    5580
gttgtattga tgttggacga gtcggaatcg cagaccgata ccaggatctt gccatcctat    5640
ggaactgcct cggtgagttt tctccttcat tacagaaacg gcttttttcaa aaatatggta    5700
```

| | |
|---|---|
| ttgataatcc tgatatgaat aaattgcagt tcatttgat gctcgatgag ttttcctaag | 5760 |
| aattaattca tgagcggata catatttgaa tgtatttaga aaaataaaca aatagggggtt | 5820 |
| ccgcgcacat ttccccgaaa agtgccacct gaaattgtaa acgttaatat tttgttaaaa | 5880 |
| ttcgcgttaa attttttgtta aatcagctca tttttttaacc aataggccga aatcggcaaa | 5940 |
| atcccttata aatcaaaaga atagaccgag atagggttga gtgttgttcc agtttggaac | 6000 |
| aagagtccac tattaaagaa cgtggactcc aacgtcaaag ggcgaaaaac cgtctatcag | 6060 |
| ggcgatggcc cactacgtga accatcaccc taatcaagtt ttttgggggtc gaggtgccgt | 6120 |
| aaagcactaa atcggaaccc taaagggagc ccccgattta gagcttgacg gggaaagccg | 6180 |
| gcgaacgtgg cgagaaagga agggaagaaa gcgaaaggag cgggcgctag ggcgctggca | 6240 |
| agtgtagcgg tcacgctgcg cgtaaccacc acacccgccg cgcttaatgc gccgctacag | 6300 |
| ggcgcgtccc attcgcca | 6318 |

<210> SEQ ID NO 45
<211> LENGTH: 6318
<212> TYPE: DNA
<213> ORGANISM: Artificial Sequence
<220> FEATURE:
<223> OTHER INFORMATION: Synthetic: plasmid

<400> SEQUENCE: 45

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgacttatta cggtttcagc ggcgggtctt tcaggttaaa ctcacggaac tgaacgtaca | 240 |
| tggtaacacg gatgttgtag tcctggtcgt atttagagtt ttcgaacgcg gtacccagac | 300 |
| caacgtggtc aacgttcgca gaggtctgca gacgcagcca gatctggtta cgtttagagt | 360 |
| tcggctggaa gtagtcgatg gtagagtcca gaaccggttt cggggtgaag taacgagagt | 420 |
| ggtaagagaa cggctgcggg atggtgtgac gagaagagta gttaacgtac gggtcgtagg | 480 |
| tcagcgcggt cgctttggta acgaagttgt cgtccaggat aaccgcggta gaaccaacac | 540 |
| cacggtcacc ctgggtgatc ggagagcacg gccaaaactc aactttaact ttacggatac | 600 |
| ggtagtattc gaacgggata gagattttgt tggtaccacc acccggcgga acgaagtcgt | 660 |
| tgatgttgaa acgcatcatg tcaaccgccc aagacggggt acgaacggta gacgctttaa | 720 |
| cggtgtaacc gaaggtacga gacagacggg tgttgaagat accgttttta cgacgccaac | 780 |
| ggtaacggtg acgcgggtga accagccacg gacgacgacg caggatctga cccaggtgag | 840 |
| aacgcggacg gtgacgacga cgacggaaac gacgacgcgg gtaggtcatg gatccgccgc | 900 |
| cgatttgttc acggtgtgct tcgataatgt cgttgtcttc catgtccagg tcttccgggg | 960 |
| tttgatccgc ctggatgcga ataccgtcat acaggaaacg cagactatcc atttccttgc | 1020 |
| cctgacgttt ggcaaacgct tccatcaggc gacgcagcgg cgtggtcttt ttgatcttaa | 1080 |
| agaaaatttc agagctgccg tcactaactt tcaggttgat gtgggtttcc ggtttcactt | 1140 |
| ccggtttcac ttccgggtttc gcttcttggt tcacttcgct atcgctcatg gtaccaccac | 1200 |
| cgctgtgatg gtgatggtga tgcgatacga attttttttt catatgtata tctccttctt | 1260 |
| aaagttaaac aaaattattt ctagagggga attgttatcc gctcacaatt cccctatagt | 1320 |
| gagtcgtatt aatttcgcgg gatcgagatc gatctcgatc ctctacgccg gacgcatcgt | 1380 |
| ggccggcatc accggcgcca caggtgcggt tgctggcgcc tatatcgccg acatcaccga | 1440 |

```
tggggaagat cgggctcgcc acttcgggct catgagcgct tgtttcggcg tgggtatggt    1500
ggcaggcccc gtggccgggg gactgttggg cgccatctcc ttgcatgcac cattccttgc    1560
ggcggcggtg ctcaacggcc tcaacctact actgggctgc ttcctaatgc aggagtcgca    1620
taagggagag cgtcgagatc ccggacacca tcgaatggcg caaaaccttt cgcggtatgg    1680
catgatagcg cccggaagag agtcaattca gggtggtgaa tgtgaaacca gtaacgttat    1740
acgatgtcgc agagtatgcc ggtgtctctt atcagaccgt ttcccgcgtg gtgaaccagg    1800
ccagccacgt ttctgcgaaa acgcgggaaa aagtggaagc ggcgatggcg gagctgaatt    1860
acattcccaa ccgcgtggca caacaactgg cgggcaaaca gtcgttgctg attggcgttg    1920
ccacctccag tctggccctg cacgcgccgt cgcaaattgt cgcggcgatt aaatctcgcg    1980
ccgatcaact gggtgccagc gtggtggtgt cgatggtaga acgaagcggc gtcgaagcct    2040
gtaaagcggc ggtgcacaat cttctcgcgc aacgcgtcag tgggctgatc attaactatc    2100
cgctggatga ccaggatgcc attgctgtgg aagctgcctg cactaatgtt ccggcgttat    2160
ttcttgatgt ctctgaccag acacccatca acagtattat tttctcccat gaagacggta    2220
cgcgactggg cgtggagcat ctggtcgcat tgggtcacca gcaaatcgcg ctgttagcgg    2280
gcccattaag ttctgtctcg gcgcgtctgc gtctggctgg ctggcataaa tatctcactc    2340
gcaatcaaat tcagccgata gcggaacggg aaggcgactg gagtgccatg tccggttttc    2400
aacaaaccat gcaaatgctg aatgagggca tcgttcccac tgcgatgctg gttgccaacg    2460
atcagatggc gctgggcgca atgcgcgcca ttaccgagtc cgggctgcgc gttggtgcgg    2520
acatctcggt agtgggatac gacgataccg aagacagctc atgttatatc cgccgttaa    2580 ccaccatcaa acaggatttt cgcctgctgg ggcaaaccag cgtggaccgc ttgctgcaac    2640
tctctcaggg ccaggcggtg aagggcaatc agctgttgcc cgtctcactg gtgaaaagaa    2700
aaaccaccct ggcgcccaat acgcaaaccg cctctccccg cgcgttggcc gattcattaa    2760
tgcagctggc acgacaggtt tcccgactgg aaagcgggca gtgagcgcaa cgcaattaat    2820
gtaagttagc tcactcatta ggcaccggga tctcgaccga tgcccttgag agccttcaac    2880
ccagtcagct ccttccggtg ggcgcggggc atgactatcg tcgccgcact tatgactgtc    2940
ttctttatca tgcaactcgt aggacaggtg ccggcagcgc tctgggtcat tttcggcgag    3000
gaccgctttc gctggagcgc gacgatgatc ggcctgtcgc ttgcggtatt cggaatcttg    3060
cacgccctcg ctcaagcctt cgtcactggt cccgccacca acgtttcgg cgagaagcag    3120 gccattatcg ccggcatggc ggccccacgg gtgcgcatga tcgtgctcct gtcgttgagg    3180
acccggctag gctggcgggg ttgccttact ggttagcaga atgaatcacc gatacgcgag    3240
cgaacgtgaa gcgactgctg ctgcaaaacg tctgcgacct gagcaacaac atgaatggtc    3300
ttcggtttcc gtgtttcgta aagtctggaa acgcggaagt cagcgccctg caccattatg    3360
ttccggatct gcatcgcagg atgctgctgg ctaccctgtg aacacctac atctgtatta    3420 acgaagcgct ggcattgacc ctgagtgatt tttctctggt cccgccgcat ccataccgcc    3480
agttgtttac cctcacaacg ttccagtaac cgggcatgtt catcatcagt aacccgtatc    3540
gtgagcatcc tctctcgttt catcggtatc attaccccca tgaacagaaa tcccccttac    3600
acggaggcat cagtgaccaa acaggaaaaa accgccctta acatgcccg ctttatcaga    3660 agccagacat taacgcttct ggagaaactc aacgagctgg acgcggatga acaggcagac    3720
atctgtgaat cgcttcacga ccacgctgat gagctttacc gcagctgcct cgcgcgtttc    3780
```

```
ggtgatgacg gtgaaaacct ctgacacatg cagctcccgg agacggtcac agcttgtctg    3840
taagcggatg ccgggagcag acaagcccgt cagggcgcgt cagcgggtgt tggcgggtgt    3900
cggggcgcag ccatgaccca gtcacgtagc gatagcggag tgtatactgg cttaactatg    3960
cggcatcaga gcagattgta ctgagagtgc accatatatg cggtgtgaaa taccgcacag    4020
atgcgtaagg agaaaatacc gcatcaggcg ctcttccgct tcctcgctca ctgactcgct    4080
gcgctcggtc gttcggctgc ggcgagcggt atcagctcac tcaaaggcgg taatacggtt    4140
atccacagaa tcagggggata cgcaggaaa gaacatgtga gcaaaaggcc agcaaaaggc    4200
caggaaccgt aaaaaggccg cgttgctggc gtttttccat aggctccgcc ccctgacga    4260
gcatcacaaa aatcgacgct caagtcagag gtggcgaaac ccgacaggac tataaagata    4320
ccaggcgttt cccctggaa gctccctcgt gcgctctcct gttccgaccc tgccgcttac    4380
cggatacctg tccgcctttc tcccttcggg aagcgtggcg ctttctcata gctcacgctg    4440
taggtatctc agttcggtgt aggtcgttcg ctccaagctg ggctgtgtgc acgaaccccc    4500
cgttcagccc gaccgctgcg ccttatccgg taactatcgt cttgagtcca acccggtaag    4560
acacgactta tcgccactgg cagcagccac tggtaacagg attagcagag cgaggtatgt    4620
aggcggtgct acagagttct tgaagtggtg gcctaactac ggctacacta aggacagt     4680
atttggtatc tgcgctctgc tgaagccagt taccttcgga aaaagagttg gtagctcttg    4740
atccggcaaa caaccaccg ctggtagcgg tggttttttt gtttgcaagc agcagattac    4800
gcgcagaaaa aaaggatctc aagaagatcc tttgatcttt tctacggggt ctgacgctca    4860
gtggaacgaa aactcacgtt aagggatttt ggtcatgaac aataaaactg tctgcttaca    4920
taaacagtaa tacaaggggt gttatgagcc atattcaacg ggaaacgtct gctctaggc    4980
cgcgattaaa ttccaacatg gatgctgatt tatatgggta aaatgggct cgcgataatg    5040
tcgggcaatc aggtgcgaca atctatcgat tgtatgggaa gcccgatgcg ccagagttgt    5100
ttctgaaaca tggcaaaggt agcgttgcca atgatgttac agatgagatg gtcagactaa    5160
actggctgac ggaatttatg cctcttccga ccatcaagca ttttatccgt actcctgatg    5220
atgcatggtt actcaccact gcgatccccg ggaaaacagc attccaggta ttagaagaat    5280
atcctgattc aggtgaaaat attgttgatg cgctggcagt gttcctgcgc cggttgcatt    5340
cgattcctgt ttgtaattgt ccttttaaca gcgatcgcgt atttcgtctc gctcaggcgc    5400
aatcacgaat gaataacggt ttggttgatg cgagtgattt tgatgacgag cgtaatggct    5460
ggcctgttga acaagtctgg aaagaaatgc ataaacttt gccattctca ccggattcag    5520
tcgtcactca tggtgatttc tcacttgata accttatttt tgacgagggg aaattaatag    5580
gttgtattga tgttggacga gtcggaatcg cagaccgata ccaggatctt gccatcctat    5640
ggaactgcct cggtgagttt tctccttcat tacagaaacg ctttttcaa aaatatggta    5700
ttgataatcc tgatatgaat aaattgcagt ttcatttgat gctcgatgag ttttctaag    5760
aattaattca tgagcggata catatttgaa tgtatttaga aaaataaaca aatagggggtt    5820
ccgcgcacat ttccccgaaa agtgccacct gaaattgtaa acgttaatat tttgttaaaa    5880
ttcgcgttaa attttgtta aatcagctca ttttttaacc aataggccga atcggcaaa    5940
atcccttata aatcaaaaga atagaccgag atagggttga gtgttgttcc agtttggaac    6000
aagagtccac tattaaagaa cgtggactcc aacgtcaaag ggcgaaaaac cgtctatcag    6060
ggcgatggcc cactacgtga accatcaccc taatcaagtt ttttggggtc gaggtgccgt    6120
aaagcactaa atcggaaccc taaagggagc ccccgattta gagcttgacg gggaaagccg    6180
```

```
gcgaacgtgg cgagaaagga agggaagaaa gcgaaaggag cgggcgctag ggcgctggca    6240
agtgtagcgg tcacgctgcg cgtaaccacc acacccgccg cgcttaatgc gccgctacag    6300
ggcgcgtccc attcgcca                                                  6318

<210> SEQ ID NO 46
<211> LENGTH: 4688
<212> TYPE: DNA
<213> ORGANISM: Artificial Sequence
<220> FEATURE:
<223> OTHER INFORMATION: Synthetic: plasmid

<400> SEQUENCE: 46
ggtaccaaag catgcaatga gctcagtaac ccgtatcgtg agcatcctct ctcgtttcat      60
cggtatcatt accccccatga acagaaatcc cccttacacg gaggcatcag tgaccaaaca    120
ggaaaaaacc gcccttaaca tggcccgctt tatcagaagc cagacattaa cgcttctgga    180
gaaactcaac gagctggacg cggatgaaca ggcagacatc tgtgaatcgc ttcacgacca    240
cgctgatgag ctttaccgca gctgcctcgc gcgtttcggt gatgacggtg aaaacctctg    300
acacatgcag ctcccggaga cggtcacagc ttgtctgtaa gcggatgccg ggagcagaca    360
agcccgtcag ggcgcgtcag cgggtgttgg cgggtgtcgg ggcgcagcca tgacccagtc    420
acgtagcgat agcggagtgt atactggctt aactatgcgg catcagagca gattgtactg    480
agagtgcacc attgcggtgt gaaataccgc acagatgcgt aaggagaaaa taccgcatca    540
ggcgctcttc cgcttcctcg ctcactgact cgctgcgctc ggtcgttcgg ctgcggcgag    600
cggtatcagc tcactcaaag gcggtaatac ggttatccac agaatcaggg gataacgcag    660
gaaagaacat gtgagcaaaa ggccagcaaa aggccaggaa ccgtaaaaag gccgcgttgc    720
tggcgttttt ccataggctc cgcccccctg acgagcatca caaaaatcga cgctcaagtc    780
agaggtggcg aaacccgaca ggactataaa gataccaggc gtttccccct ggaagctccc    840
tcgtgcgctc tcctgttccg accctgccgc ttaccggata cctgtccgcc tttctccctt    900
cgggaagcgt ggcgctttct catagctcac gctgtaggta tctcagttcg gtgtaggtcg    960
ttcgctccaa gctgggctgt gtgcacgaac cccccgttca gcccgaccgc tgcgccttat   1020
ccggtaacta tcgtcttgag tccaacccgg taagacacga cttatcgcca ctggcagcag   1080
ccactggtaa caggattagc agagcgaggt atgtaggcgg tgctacagag ttcttgaagt   1140
ggtggcctaa ctacggctac actagaagga cagtatttgg tatctgcgct ctgctgaagc   1200
cagttacctt cggaaaaaga gttggtagct cttgatccgg caaacaaacc accgctggta   1260
gcggtggttt ttttgtttgc aagcagcaga ttacgcgcag aaaaaaagga tctcaagaag   1320
atcctttgat cttttctacg gggtctgacg ctcagtggaa cgaaaactca cgttaaggga   1380
ttttggtcat gaacaataaa actgtctgct tacataaaca gtaatacaag gggtgttatg   1440
agccatatca cgggaaacg ctcgagtacg tatctagagc aaagcttatc gtcgacttat   1500
tacggtttca gcggcgggtc tttcaggtta aactcacgga actgaacgta catggtaaca   1560
cggatgttgt agtcctggtc gtatttagag ttttcgaacg cggtacccag accaacgtgg   1620
tcaacgttcg cagaggtctg cagacgcagc cagatctggt tacgtttaga gttcggctgg   1680
aagtagtcga tggtagagtc cagaaccggt ttcggggtga agtaacgaga gtggtaagag   1740
aacggctgcg ggatggtgtg acgagaagag tagttaacgt acgggtcgta ggtcagcgcg   1800
gtcgctttgg taacgaagtt gtcgtccagg ataaccgcgg tagaaccaac accacggtca   1860
```

```
ccctgggtga tcggagagca cggccaaaac tcaactttaa ctttacggat acggtagtat    1920
tcgaacggga tagagatttt gttggtacca ccacccggcg gaacgaagtc gttgatgttg    1980
aaacgcatca tgtcaaccgc caagacgggg gtacgaacgg tagacgcttt aacggtgtaa    2040
ccgaaggtac gagacagacg ggtgttgaag ataccgtttt tacgacgcca acggtaacgg    2100
tgacgcgggt gaaccagcca cggacgacga cgcaggatct gacccaggtg agaacgcgga    2160
cggtgacgac gacgacggaa acgacgcgcg gggtaggtca tggatccgcc gccgatttgt    2220
tcacggtgtg cttcgataat gtcgttgtct tccatgtcca ggtcttccgg ggtttgatcc    2280
gcctggatgc gaataccgtc atacaggaaa cgcagactat ccatttcctt gccctgacgt    2340
ttggcaaacg cttccatcag gcgacgcagc ggcgtggtct ttttgatctt aaagaaaatt    2400
tcagagctgc cgtcactaac tttcaggttg atgtgggttt ccggtttcac ttccggtttc    2460
acttccggtt tcgcttcttg gttcacttcg ctatcgctca tggtaccacc accgctgtga    2520
tggtgatggt gatgcgatac gaatttttt ttcatatgta ttcctccttc ttaaagttaa    2580
acaaaaaaac gggtatggag aaacagtagc aagttgcgat aaaaagcgtc aggtaggatc    2640
cgctaatctt atggataaaa atgctatggc atagcaaagt gtgacgccgt gcaaataatc    2700
aatgtggact tttctgccgt gattatagac acttttgtta cgcgttttg tcatggcttt    2760 ggtcccgctt tgttacagaa tgcttttaat aagcggggtt accggtttgg ttagcgagaa    2820
gagccagtaa aagacgcagt gacggcaatg tctgatgcaa tatggacaat tggtttcttc    2880
tctgaatggc gggagtatga aaagtatggc tgaagcgcaa aatgatcccc tgctgccggg    2940
atactcgttt aatgcccatc tggtggcggg tttaacgccg attgaggcca acggttatct    3000
cgattttttt atcgaccgac cgctgggaat gaaaggttat attctcaatc tcaccattcg    3060
cggtcagggg gtggtgaaaa atcagggacg agaatttgtt tgccgaccgg gtgatatttt    3120
gctgttcccg ccaggagaga ttcatcacta cggtcgtcat ccggaggctc gcgaatggta    3180
tcaccagtgg gtttactttc gtccgcgcgc ctactggcat gaatggctta actgccgtc    3240 aatatttgcc aatacggggt tctttcgccc ggatgaagcg caccagccgc atttcagcga    3300
cctgtttggg caaatcatta acgccgggca aggggaaggg cgctattcgg agctgctggc    3360
gataaatctg cttgagcaat tgttactgcg gcgcatggaa gcgattaacg agtcgctcca    3420
tccaccgatg gataatcggg tacgcgaggc ttgtcagtac atcagcgatc acctggcaga    3480
cagcaatttt gatatcgcca gcgtcgcaca gcatgtttgc ttgtcgccgt cgcgtctgtc    3540
acatcttttc cgccagcagt tagggattag cgtcttaagc tggcgcgagg accaacgtat    3600
cagccaggcg aagctgcttt tgagcaccac ccggatgcct atcgccaccg tcggtcgcaa    3660
tgttggtttt gacgatcaac tctatttctc gcgggtattt aaaaaatgca ccggggccag    3720
cccgagcgag ttccgtgccg gttgtgaaga aaaagtgaat gatgtagccg tcaagttgtc    3780
ataattggta acgaatcaga caattgacgg cttgacggag tagcataggg tttgcagaat    3840
ccctgcttcg tccatttgac aggcacatta tgcgaattcg ctagcagatc ttagtgacat    3900
tagaaaaccg actgtaaaaa gtacagtcgg cattatctca tattataaaa gccagtcatt    3960
aggcctatct gacaattcct gaatagagtt cataaacaat cctgcatgat aaccatcaca    4020
aacagaatga tgtacctgta agatagcgg taaatatatt gaattacctt tattaatgaa    4080
ttttcctgct gtaataatgg gtagaaggta attactatta ttattgatat ttaagttaaa    4140
cccagtaaat gaagtccatg gaataataga aagagaaaaa gcattttcag gtataggtgt    4200
tttgggaaac aatttccccg aaccattata tttctctaca tcagaaaggt ataaatcata    4260
```

```
aaactctttg aagtcattct ttacaggagt ccaaataccz gagaatgttt tagatacacc    4320
atcaaaaatt gtataaagtg gctctaactt atcccaataa cctaactctc cgtcgctatt    4380
gtaaccagtt ctaaaagctg tatttgagtt tatcacccct gtcactaaga aaataaatgc    4440
agggtaaaat ttatatcctt cttgttttat gtttcggtat aaaacactaa tatcaatttc    4500
tgtggttata ctaaaagtcg tttgttggtt caaataatga ttaaatatct cttttctctt    4560
ccaattgtct aaatcaattt tattaaagtt catttgatat gcctcctaaa ttttttatcta   4620 aagtgaattt aggaggctta cttgtctgct ttcttcatta gaatcaatcc ttttttaaaa    4680
gtcaatcc                                                            4688
```

<210> SEQ ID NO 47
<211> LENGTH: 40
<212> TYPE: DNA
<213> ORGANISM: Artificial Sequence
<220> FEATURE:
<223> OTHER INFORMATION: Synthetic: primer

<400> SEQUENCE: 47

```
caatatggat cccttgttcc tgaattaaat gaaaaagacg                            40
```

<210> SEQ ID NO 48
<211> LENGTH: 75
<212> TYPE: DNA
<213> ORGANISM: Artificial Sequence
<220> FEATURE:
<223> OTHER INFORMATION: Synthetic: primer

<400> SEQUENCE: 48

```
gatatactcg agttagtgat ggtgatggtg atgaccactg ccgctacctt ttaaagcgtc     60
ggttaaaatc aaatg                                                      75
```

<210> SEQ ID NO 49
<211> LENGTH: 6051
<212> TYPE: DNA
<213> ORGANISM: Artificial Sequence
<220> FEATURE:
<223> OTHER INFORMATION: Synthetic: plasmid

<400> SEQUENCE: 49

```
atccggatat agttcctcct ttcagcaaaa aacccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgagttagtg atggtgatgg tgatgaccac tgccgctacc ttttaaagcg tcggttaaaa    240
tcaaatgggc aataaatctt ctcatcctaa tcgcatcttt ataatcaaaa tccaatggcg    300
catctgcact tccatagaga gtattcatac aaacatatat tccgcagtcg tagccatttg    360
gttgctgcgg acaatctaaa tgaatcaaat caaagtcttc tcctattgta tgcttacttt    420
cctccataac atattttttgc aagtcagtca gtatagcgaa actcatagca tttggaccat    480
tcgataatga atctacgtaa cctatagttt tcttttttaa atcaattatg cccaacgccc    540
agtgggattg gttcaaattt attggtgtaa agattttatc aagtttatca atttgtgtct    600
tctttctctt catccaccte cggacgcctt gataacccct ttctgataaa ttggtataga    660
aaaacgaatt aaacgccact gtattagggg tagatttttc aatgtatttc ataaaaaact    720
caatgatagt gtcatttagc catcttcgtg gtgccaaggt cttaaaatca cgtactgtta    780
```

```
tctctatatt atctctattc attaactgag tattttctct agatgccaaa gcttttttgta    840
cttggtcatc gtcttttttca tttaattcag gaacaaggga tccgatatca gccatggaac    900
cgcgtggcac cagggtaccc agatctgggc tgtccatgtg ctggcgttcg aatttagcag    960
cagcggtttc tttcatatgt atatctcctt cttaaagtta aacaaaatta tttctagagg   1020
ggaattgtta tccgctcaca attccccctat agtgagtcgt attaatttcg cgggatcgag   1080
atcgatctcg atcctctacg ccggacgcat cgtggccggc atcaccgcg ccacaggtgc    1140
ggttgctggc gcctatatcg ccgacatcac cgatgggaa gatcgggctc gccacttcgg   1200
gctcatgagc gcttgtttcg gcgtgggtat ggtggcaggc cccgtggccg gggactgtt    1260
gggcgccatc tccttgcatg caccattcct tgcggcggcg gtgctcaacg gcctcaacct   1320
actactgggc tgcttcctaa tgcaggagtc gcataaggga gagcgtcgag atcccggaca   1380
ccatcgaatg gcgcaaaacc tttcgcggta tggcatgata gcgcccggaa gagagtcaat   1440
tcagggtggt gaatgtgaaa ccagtaacgt tatacgatgt cgcagagtat gccggtgtct   1500
cttatcagac cgtttcccgc gtggtgaacc aggccagcca cgtttctgcg aaaacgcggg   1560
aaaaagtgga agcggcgatg gcggagctga attacattcc caaccgcgtg gcacaacaac   1620
tggcgggcaa acagtcgttg ctgattggcg ttgccacctc cagtctggcc ctgcacgcgc   1680
cgtcgcaaat tgtcgcggcg attaaatctc gcgccgatca actgggtgcc agcgtggtgg   1740
tgtcgatggt agaacgaagc ggcgtcgaag cctgtaaagc ggcggtgcac aatcttctcg   1800
cgcaacgcgt cagtgggctg atcattaact atccgctgga tgaccaggat gccattgctg   1860
tggaagctgc ctgcactaat gttccggcgt tatttcttga tgtctctgac cagacaccca   1920
tcaacagtat tattttctcc catgaagacg gtacgcgact gggcgtggag catctggtcg   1980
cattgggtca ccagcaaatc gcgctgttag cgggcccatt aagttctgtc tcggcgcgtc   2040
tgcgtctggc tggctggcat aaatatctca ctcgcaatca aattcagccg atagcggaac   2100
gggaaggcga ctggagtgcc atgtccggtt ttcaacaaac catgcaaatg ctgaatgagg   2160
gcatcgttcc cactgcgatg ctggttgcca acgatcagat ggcgctgggc gcaatgcgcg   2220
ccattaccga gtccgggctg cgcgttggtg cggacatctc ggtagtggga tacgacgata   2280
ccgaagacag ctcatgttat atcccgccgt taaccaccat caaacaggat tttcgcctgc   2340
tggggcaaac cagcgtggac cgcttgctgc aactctctca gggccaggcg gtgaagggca   2400
atcagctgtt gcccgtctca ctggtgaaaa gaaaaaccac cctggcgccc aatacgcaaa   2460
ccgcctctcc ccgcgcgttg gccgattcat taatgcagct ggcacgacag gtttcccgac   2520
tggaaagcgg gcagtgagcg caacgcaatt aatgtaagtt agctcactca ttaggcaccg   2580
ggatctcgac cgatgccctt gagagccttc aacccagtca gctccttccg gtgggcgcgg   2640
ggcatgacta tcgtcgccgc acttatgact gtcttcttta tcatgcaact cgtaggacag   2700
gtgccggcag cgctctgggt catttttcgg gaggaccgct ttcgctggag cgcgacgatg   2760
atcggcctgt cgcttgcggt attcggaatc ttgcacgccc tcgctcaagc cttcgtcact   2820
ggtcccgcca ccaaacgttt cggcgagaag caggccatta tcgccggcat ggcggcccca   2880
cgggtgcgca tgatcgtgct cctgtcgttg aggacccggc taggctggcg gggttgcctt   2940
actggttagc agaatgaatc accgatacgc gagcgaacgt gaagcgactg ctgctgcaaa   3000
acgtctgcga cctgagcaac aacatgaatg tcttcggtt ccgtgttttc gtaaagtctg   3060
gaaacgcgga agtcagcgcc ctgcaccatt atgttccgga tctgcatcgc aggatgctgc   3120
tggctaccct gtggaacacc tacatctgta ttaacgaagc gctggcattg accctgagtg   3180
```

```
atttttctct ggtcccgccg catccatacc gccagttgtt taccctcaca acgttccagt    3240
aaccgggcat gttcatcatc agtaacccgt atcgtgagca tcctctctcg tttcatcggt    3300
atcattaccc ccatgaacag aaatccccct tacacggagg catcagtgac caaacaggaa    3360
aaaaccgccc ttaacatggc ccgctttatc agaagccaga cattaacgct tctggagaaa    3420
ctcaacgagc tggacgcgga tgaacaggca gacatctgtg aatcgcttca cgaccacgct    3480
gatgagcttt accgcagctg cctcgcgcgt ttcggtgatg acggtgaaaa cctctgacac    3540
atgcagctcc cggagacggt cacagcttgt ctgtaagcgg atgccgggag cagacaagcc    3600
cgtcagggcg cgtcagcggg tgttggcggg tgtcggggcg cagccatgac ccagtcacgt    3660
agcgatagcg gagtgtatac tggcttaact atgcggcatc agagcagatt gtactgagag    3720
tgcaccatat atgcggtgtg aaataccgca cagatgcgta aggagaaaat accgcatcag    3780
gcgctcttcc gcttcctcgc tcactgactc gctgcgctcg gtcgttcggc tgcggcgagc    3840
ggtatcagct cactcaaagg cggtaatacg gttatccaca gaatcagggg ataacgcagg    3900
aaagaacatg tgagcaaaag gccagcaaaa ggccaggaac cgtaaaaagg ccgcgttgct    3960
ggcgtttttc cataggctcc gcccccctga cgagcatcac aaaaatcgac gctcaagtca    4020
gaggtggcga aacccgacag gactataaag ataccaggcg tttccccctg gaagctccct    4080
cgtgcgctct cctgttccga ccctgccgct taccggatac ctgtccgcct ttctcccttc    4140
gggaagcgtg gcgctttctc atagctcacg ctgtaggtat ctcagttcgg tgtaggtcgt    4200
tcgctccaag ctgggctgtg tgcacgaacc ccccgttcag cccgaccgct gcgccttatc    4260
cggtaactat cgtcttgagt ccaacccggt aagacacgac ttatcgccac tggcagcagc    4320
cactggtaac aggattagca gagcgaggta tgtaggcggt gctacagagt tcttgaagtg    4380
gtggcctaac tacggctaca ctagaaggac agtatttggt atctgcgctc tgctgaagcc    4440
agttaccttc ggaaaaagag ttggtagctc ttgatccggc aaacaaacca ccgctggtag    4500
cggtggtttt tttgtttgca agcagcagat tacgcgcaga aaaaaaggat ctcaagaaga    4560
tcctttgatc ttttctacgg ggtctgacgc tcagtggaac gaaaactcac gttaagggat    4620
tttggtcatg aacaataaaa ctgtctgctt acataaacag taatacaagg ggtgttatga    4680
gccatattca acgggaaacg tcttgctcta ggccgcgatt aaattccaac atggatgctg    4740
atttatatgg gtataaatgg gctcgcgata atgtcgggca atcaggtgcg acaatctatc    4800
gattgtatgg gaagcccgat gcgccagagt tgtttctgaa acatggcaaa ggtagcgttg    4860
ccaatgatgt tacagatgag atggtcagac taaactggct gacggaattt atgcctcttc    4920
cgaccatcaa gcattttatc cgtactcctg atgatgcatg gttactcacc actgcgatcc    4980
ccgggaaaac agcattccag gtattagaag aatatcctga ttcaggtgaa atattgttg     5040 atgcgctggc agtgttcctg cgccggttgc attcgattcc tgtttgtaat tgtccttta     5100 acagcgatcg cgtatttcgt ctcgctcagg cgcaatcacg aatgaataac ggtttggttg    5160
atgcgagtga ttttgatgac gagcgtaatg gctggcctgt gaacaagtc tggaaagaaa     5220 tgcataaact tttgccattc tcaccggatt cagtcgtcac tcatggtgat ttctcacttg    5280
ataaccttat ttttgacgag gggaaattaa taggttgtat tgatgttgga cgagtcggaa    5340
tcgcagaccg ataccaggat cttgccatcc tatggaactg cctcggtgag ttttctcctt    5400
cattacagaa acggcttttt caaaaatatg gtattgataa tcctgatatg aataaattgc    5460
agtttcattt gatgctcgat gagttttct aagaattaat tcatgagcgg atacatattt     5520
```

| | |
|---|---|
| gaatgtattt agaaaaataa acaaataggg gttccgcgca catttccccg aaaagtgcca | 5580 |
| cctgaaattg taaacgttaa tattttgtta aaattcgcgt taaattttg ttaaatcagc | 5640 |
| tcatttttta accaataggc cgaaatcggc aaaatcccctt ataaatcaaa agaatagacc | 5700 |
| gagatagggt tgagtgttgt tccagtttgg aacaagagtc cactattaaa gaacgtggac | 5760 |
| tccaacgtca aagggcgaaa aaccgtctat cagggcgatg gcccactacg tgaaccatca | 5820 |
| ccctaatcaa gttttttggg gtcgaggtgc cgtaaagcac taaatcggaa ccctaaaggg | 5880 |
| agcccccgat ttagagcttg acggggaaag ccggcgaacg tggcgagaaa ggaagggaag | 5940 |
| aaagcgaaag gagcgggcgc tagggcgctg gcaagtgtag cggtcacgct gcgcgtaacc | 6000 |
| accacacccg ccgcgcttaa tgccgccgcta cagggcgcgt cccattcgcc a | 6051 |

<210> SEQ ID NO 50
<211> LENGTH: 36
<212> TYPE: DNA
<213> ORGANISM: Artificial Sequence
<220> FEATURE:
<223> OTHER INFORMATION: Synthetic: primer

<400> SEQUENCE: 50

| | |
|---|---|
| gatataggta ccatgacgag caaagaaacc tttacc | 36 |

<210> SEQ ID NO 51
<211> LENGTH: 32
<212> TYPE: DNA
<213> ORGANISM: Artificial Sequence
<220> FEATURE:
<223> OTHER INFORMATION: Synthetic: primer

<400> SEQUENCE: 51

| | |
|---|---|
| caatatggat ccaacgatgc tgattgccgt tc | 32 |

<210> SEQ ID NO 52
<211> LENGTH: 6351
<212> TYPE: DNA
<213> ORGANISM: Artificial Sequence
<220> FEATURE:
<223> OTHER INFORMATION: Synthetic: plasmid

<400> SEQUENCE: 52

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgagttagtg atggtgatgg tgatgaccac tgccgctacc ttttaaagcg tcggttaaaa | 240 |
| tcaaatgggc aataaatctt ctcatcctaa tcgcatcttt ataatcaaaa tccaatggcg | 300 |
| catctgcact tccatagaga gtattcatac aaacatatat tccgcagtcg tagccatttg | 360 |
| gttgctgcgg acaatctaaa tgaatcaaat caaagtcttc tcctattgta tgcttacttt | 420 |
| cctccataac atattttgc aagtcagtca gtatagcgaa actcatagca tttgaccat | 480 |
| tcgataatga atctacgtaa cctatagttt tcttttttaa atcaattatg cccaacgccc | 540 |
| agtgggattg gttcaaattt attggtgtaa agatttatc aagttatca atttgtgtct | 600 |
| tctttctctt catccacctc cggacgcctt gataacccct ttctgataaa ttggtataga | 660 |
| aaaacgaatt aaacgccact gtattagggg tagattttc aatgtatttc ataaaaaact | 720 |
| caatgatagt gtcatttagc catcttcgtg gtgccaaggt cttaaaatca cgtactgtta | 780 |
| tctctatatt atctctattc attaactgag tattttctct agatgccaaa gcttttgta | 840 |

```
cttggtcatc gtcttttca tttaattcag gaacaaggga tccaacgatg ctgattgccg      900
ttccggcaaa cgcggtccgt tttttcgtct cgtcgctggc agcctccggc cagagcacat      960
cctcataacg gaacgtgccg gacttgtaga acgtcagcgt ggtgctggtc tggtcagcag     1020
caaccgcaag aatgccaacg gcagcaccgt cggtggtgcc atcccacgca accagcttac     1080
ggctggaggt gtccagcatc agcggggtca ttgcaggcgc tttcgcactc aatccgccgg     1140
gcgcggttgc ggtatgagcc gggtcactgt tgccctgcgg ctggtaatgg gtaaaggttt     1200
ctttgctcgt catggtaccc agatctgggc tgtccatgtg ctggcgttcg aatttagcag     1260
cagcggtttc tttcatatgt atatctcctt cttaaagtta aacaaaatta tttctagagg     1320
ggaattgtta tccgctcaca attccctat agtgagtcgt attaatttcg cgggatcgag      1380
atcgatctcg atcctctacg ccggacgcat cgtggccggc atcaccggcg ccacaggtgc     1440
ggttgctggc gcctatatcg ccgacatcac cgatgggaa gatcgggctc gccacttcgg      1500
gctcatgagc gcttgtttcg gcgtgggtat ggtggcaggc cccgtggccg ggggactgtt     1560
gggcgccatc tccttgcatg caccattcct tgcggcggcg gtgctcaacg gcctcaacct     1620
actactgggc tgcttcctaa tgcaggagtc gcataaggga gagcgtcgag atcccggaca     1680
ccatcgaatg gcgcaaaacc tttcgcggta tggcatgata gcgcccggaa gagagtcaat     1740
tcagggtggt gaatgtgaaa ccagtaacgt tatacgatgt cgcagagtat gccggtgtct     1800
cttatcagac cgtttcccgc gtggtgaacc aggccagcca cgtttctgcg aaaacgcggg     1860
aaaaagtgga agcggcgatg gcggagctga attacattcc caaccgcgtg gcacaacaac     1920
tggcgggcaa acagtcgttg ctgattggcg ttgccacctc cagtctggcc ctgcacgcgc     1980
cgtcgcaaat tgtcgcggcg attaaatctc gcgccgatca actgggtgcc agcgtggtgg     2040
tgtcgatggt agaacgaagc ggcgtcgaag cctgtaaagc ggcggtgcac aatcttctcg     2100
cgcaacgcgt cagtgggctg atcattaact atccgctgga tgaccaggat gccattgctg     2160
tggaagctgc ctgcactaat gttccggcgt tatttcttga tgtctctgac cagacaccca     2220
tcaacagtat tattttctcc catgaagacg gtacgcgact gggcgtggag catctggtcg     2280
cattgggtca ccagcaaatc gcgctgttag cgggcccatt aagttctgtc tcggcgcgtc     2340
tgcgtctggc tggctggcat aaatatctca ctcgcaatca aattcagccg atagcggaac     2400
gggaaggcga ctggagtgcc atgtccggtt ttcaacaaac catgcaaatg ctgaatgagg     2460
gcatcgttcc cactgcgatg ctggttgcca acgatcagat ggcgctgggc gcaatgcgcg     2520
ccattaccga gtccgggctg cgcgttggtg cggacatctc ggtagtggga tacgacgata     2580
ccgaagacag ctcatgttat atcccgccgt taaccaccat caaacaggat tttcgcctgc     2640
tggggcaaac cagcgtggac cgcttgctgc aactctctca gggccaggcg gtgaagggca     2700
atcagctgtt gcccgtctca ctggtgaaaa gaaaaccac cctggcgccc aatacgcaaa     2760
ccgcctctcc ccgcgcgttg gccgattcat taatgcagct ggcacgacag gtttcccgac     2820
tggaaagcgg gcagtgagcg caacgcaatt aatgtaagtt agctcactca ttaggcaccg     2880
ggatctcgac cgatgccctt gagagccttc aacccagtca gctccttccg gtgggcgcgg     2940
ggcatgacta tcgtcgccgc acttatgact gtcttcttta tcatgcaact cgtaggacag     3000
gtgccggcag cgctctgggt cattttcggc gaggaccgct ttcgctggag cgcgacgatg     3060 atcgcctgt cgcttgcggt attcggaatc ttgcacgccc tcgctcaagc cttcgtcact     3120
ggtcccgcca ccaaacgttt cggcgagaag caggccatta tcgccggcat ggcggcccca     3180
```

```
cgggtgcgca tgatcgtgct cctgtcgttg aggacccggc taggctggcg gggttgcctt    3240
actggttagc agaatgaatc accgatacgc gagcgaacgt gaagcgactg ctgctgcaaa    3300
acgtctgcga cctgagcaac aacatgaatg gtcttcggtt tccgtgtttc gtaaagtctg    3360
gaaacgcgga agtcagcgcc ctgcaccatt atgttccgga tctgcatcgc aggatgctgc    3420
tggctaccct gtggaacacc tacatctgta ttaacgaagc gctggcattg accctgagtg    3480 attttttctct ggtcccgccg catccatacc gccagttgtt taccctcaca acgttccagt    3540
aaccgggcat gttcatcatc agtaacccgt atcgtgagca tcctctctcg tttcatcggt    3600
atcattaccc ccatgaacag aaatccccct tacacggagg catcagtgac caaacaggaa    3660
aaaaccgccc ttaacatggc ccgctttatc agaagccaga cattaacgct tctggagaaa    3720
ctcaacgagc tggacgcgga tgaacaggca gacatctgtg aatcgcttca cgaccacgct    3780
gatgagcttt accgcagctg cctcgcgcgt ttcggtgatg acggtgaaaa cctctgacac    3840
atgcagctcc cggagacggt cacagcttgt ctgtaagcgg atgccgggag cagacaagcc    3900
cgtcagggcg cgtcagcggg tgttggcggg tgtcggggcg cagccatgac ccagtcacgt    3960
agcgatagcg gagtgtatac tggcttaact atgcggcatc agagcagatt gtactgagag    4020
tgcaccatat atgcggtgtg aaataccgca cagatgcgta aggagaaaat accgcatcag    4080
gcgctcttcc gcttcctcgc tcactgactc gctgcgctcg gtcgttcggc tgcggcgagc    4140
ggtatcagct cactcaaagg cggtaatacg gttatccaca gaatcagggg ataacgcagg    4200
aaagaacatg tgagcaaaag gccagcaaaa ggccaggaac cgtaaaaagg ccgcgttgct    4260
ggcgtttttc cataggctcc gcccccctga cgagcatcac aaaaatcgac gctcaagtca    4320
gaggtggcga aacccgacag gactataaag ataccaggcg tttccccctg gaagctccct    4380
cgtgcgctct cctgttccga ccctgccgct taccggatac ctgtccgcct ttctcccttc    4440
gggaagcgtg gcgctttctc atagctcacg ctgtaggtat ctcagttcgg tgtaggtcgt    4500
tcgctccaag ctgggctgtg tgcacgaacc ccccgttcag cccgaccgct gcgccttatc    4560
cggtaactat cgtcttgagt ccaacccggt aagacacgac ttatcgccac tggcagcagc    4620
cactggtaac aggattagca gagcgaggta tgtaggcggt gctacagagt tcttgaagtg    4680
gtggcctaac tacggctaca ctagaaggac agtatttggt atctgcgctc tgctgaagcc    4740
agttaccttc ggaaaaagag ttggtagctc ttgatccggc aaacaaacca ccgctggtag    4800
cggtggtttt tttgtttgca agcagcagat tacgcgcaga aaaaaaggat ctcaagaaga    4860
tcctttgatc ttttctacgg ggtctgacgc tcagtggaac gaaaactcac gttaagggat    4920
tttggtcatg aacaataaaa ctgtctgctt acataaacag taatacaagg ggtgttatga    4980
gccatattca acgggaaacg tcttgctcta ggccgcgatt aaattccaac atggatgctg    5040
atttatatgg gtataaatgg gctcgcgata atgtcgggca atcaggtgcg acaatctatc    5100
gattgtatgg gaagcccgat gcgccagagt tgtttctgaa acatggcaaa ggtagcgttg    5160
ccaatgatgt tacagatgag atggtcagac taaactggct gacggaattt atgcctcttc    5220
cgaccatcaa gcattttatc cgtactcctg atgatgcatg gttactcacc actgcgatcc    5280
ccgggaaaac agcattccag gtattagaag aatatcctga ttcaggtgaa atattgttg    5340 atgcgctggc agtgttcctg cgccggttgc attcgattcc tgtttgtaat gtccttttta    5400
acagcgatcg cgtatttcgt ctcgctcagg cgcaatcacg aatgaataac ggtttggttg    5460
atgcgagtga ttttgatgac gagcgtaatg gctggcctgt tgaacaagtc tggaaagaaa    5520
tgcataaact tttgccattc tcaccggatt cagtcgtcac tcatggtgat ttctcacttg    5580
```

```
ataaccttat ttttgacgag gggaaattaa taggttgtat tgatgttgga cgagtcggaa    5640
tcgcagaccg ataccaggat cttgccatcc tatggaactg cctcggtgag ttttctcctt    5700
cattacagaa acggcttttt caaaaatatg gtattgataa tcctgatatg aataaattgc    5760
agtttcattt gatgctcgat gagttttttct aagaattaat tcatgagcgg atacatattt   5820
gaatgtattt agaaaaataa acaaataggg gttccgcgca catttccccg aaaagtgcca    5880
cctgaaattg taaacgttaa tattttgtta aaattcgcgt taaattttttg ttaaatcagc   5940 tcattttttta accaataggc cgaaatcggc aaaatccctt ataaatcaaa agaatagacc    6000
gagatagggt tgagtgttgt tccagtttgg aacaagagtc cactattaaa gaacgtggac    6060
tccaacgtca aagggcgaaa aaccgtctat cagggcgatg gcccactacg tgaaccatca    6120
ccctaatcaa gttttttggg gtcgaggtgc cgtaaagcac taaatcggaa ccctaaaggg    6180
agcccccgat ttagagcttg acggggaaag ccggcgaacg tggcgagaaa ggaagggaag    6240
aaagcgaaag gagcgggcgc tagggcgctg gcaagtgtag cggtcacgct gcgcgtaacc    6300
accacacccg ccgcgcttaa tgcgccgcta cagggcgcgt cccattcgcc a             6351
```

<210> SEQ ID NO 53
<211> LENGTH: 64
<212> TYPE: DNA
<213> ORGANISM: Artificial Sequence
<220> FEATURE:
<223> OTHER INFORMATION: Synthetic: primer

<400> SEQUENCE: 53

```
tgcgatctgc cgcaaaccca cagtctggct cacacccgtg ccctgcgtct gctggcccaa    60
atgc                                                                 64
```

<210> SEQ ID NO 54
<211> LENGTH: 79
<212> TYPE: DNA
<213> ORGANISM: Artificial Sequence
<220> FEATURE:
<223> OTHER INFORMATION: Synthetic: primer

<400> SEQUENCE: 54

```
cttcgtgcgg agagccaaag tcgcgacgat gatccagaca actgaacggg gagatacgac    60
gcatttgggc cagcagacg                                                 79
```

<210> SEQ ID NO 55
<211> LENGTH: 67
<212> TYPE: DNA
<213> ORGANISM: Artificial Sequence
<220> FEATURE:
<223> OTHER INFORMATION: Synthetic: primer

<400> SEQUENCE: 55

```
actttggctc tccgcacgaa gcattcggcg gtaaccaggt gcaaaaagct caggcgatgg    60
ccctggt                                                              67
```

<210> SEQ ID NO 56
<211> LENGTH: 93
<212> TYPE: DNA
<213> ORGANISM: Artificial Sequence
<220> FEATURE:
<223> OTHER INFORMATION: Synthetic: primer

<400> SEQUENCE: 56

```
gcagtgattc atcccatgcg gccgcggagc cttccgtact gaacagttga aaggtttgct    60
gcagcatttc atgaaccagg gccatcgcct gag                                 93
```

<210> SEQ ID NO 57
<211> LENGTH: 81
<212> TYPE: DNA
<213> ORGANISM: Artificial Sequence
<220> FEATURE:
<223> OTHER INFORMATION: Synthetic: primer

<400> SEQUENCE: 57

```
ccgcatggga tgaatcactg ctgcaccagt tttgcaccgg tctggatcag caactgcgtg    60
acctggaagc atgtgtcatg c                                              81
```

<210> SEQ ID NO 58
<211> LENGTH: 83
<212> TYPE: DNA
<213> ORGANISM: Artificial Sequence
<220> FEATURE:
<223> OTHER INFORMATION: Synthetic: primer

<400> SEQUENCE: 58

```
tacgcaccgc cagaatcgaa tcttcttcca gcagcggggt gccttccagg ccagcttcct    60
gcatgacaca tgcttccagg tca                                            83
```

<210> SEQ ID NO 59
<211> LENGTH: 90
<212> TYPE: DNA
<213> ORGANISM: Artificial Sequence
<220> FEATURE:
<223> OTHER INFORMATION: Synthetic: primer

<400> SEQUENCE: 59

```
attcgattct ggcggtgcgt aaatatttcc atcgcctgac gctgtatctg caggaaaaga    60
gctactctcc gtgcgcgtgg gaaatcgttc                                     90
```

<210> SEQ ID NO 60
<211> LENGTH: 85
<212> TYPE: DNA
<213> ORGANISM: Artificial Sequence
<220> FEATURE:
<223> OTHER INFORMATION: Synthetic: primer

<400> SEQUENCE: 60

```
ttcctttta cgcaggcggt cttgcagatt acggcttgac gagaacgaac gcatcacttc     60
ggcgcgaacg atttcccacg cgcac                                          85
```

<210> SEQ ID NO 61
<211> LENGTH: 18
<212> TYPE: DNA
<213> ORGANISM: Artificial Sequence
<220> FEATURE:
<223> OTHER INFORMATION: Synthetic: primer

<400> SEQUENCE: 61

```
tgcgatctgc cgcaaacc                                                  18
```

<210> SEQ ID NO 62
<211> LENGTH: 21
<212> TYPE: DNA
<213> ORGANISM: Artificial Sequence
<220> FEATURE:
<223> OTHER INFORMATION: Synthetic: primer

<400> SEQUENCE: 62
ttccttttta cgcaggcggt c                                              21

<210> SEQ ID NO 63
<211> LENGTH: 3472
<212> TYPE: DNA
<213> ORGANISM: Artificial Sequence
<220> FEATURE:
<223> OTHER INFORMATION: Synthetic: plasmid

<400> SEQUENCE: 63

| | | | | | |
|---|---|---|---|---|---|
| gcccctgcag | ccgaattata | ttattttgc | caaataattt | ttaacaaaag | ctctgaagtc | 60 |
| ttcttcattt | aaattcttag | atgatacttc | atctggaaaa | ttgtcccaat | tagtagcatc | 120 |
| acgctgtgag | taagttctaa | accatttttt | tattgttgta | ttatctctaa | tcttactact | 180 |
| cgatgagttt | tcggtattat | ctctattttt | aacttggagc | aggttccatt | cattgttttt | 240 |
| ttcatcatag | tgaataaaat | caactgcttt | aacacttgtg | cctgaacacc | atatccatcc | 300 |
| ggcgtaatac | gactcactat | agggagagcg | gccgccagat | cttccggatg | gctcgagttt | 360 |
| ttcagcaaga | tttccttttt | acgcaggcgg | tcttgcagat | tacggcttga | cgagaacgaa | 420 |
| cgcatcactt | cggcgcgaac | gatttcccac | gcgcacggag | agtagctctt | ttcctgcaga | 480 |
| tacagcgtca | ggcgatggaa | atatttacgc | accgccagaa | tcgaatcttc | ttccagcagc | 540 |
| ggggtgcctt | ccaggccagc | ttcctgcatg | acacatgctt | ccaggtcacg | cagttgctga | 600 |
| tccagaccgg | tgcaaaactg | gtgcagcagt | gattcatccc | atgcggccgc | ggagccttcc | 660 |
| gtactgaaca | gttgaaaggt | ttgctgcagc | atttcatgaa | ccagggccat | cgcctgagct | 720 |
| ttttgcacct | ggttaccgcc | gaatgcttcg | tgcggagagc | caaagtcgcg | acgatgatcc | 780 |
| agacaactga | acggggagat | acgacgcatt | tgggccagca | gacgcagggc | acgggtgtga | 840 |
| gccagactgt | gggtttgcgg | cagatcgcaa | tctttctaga | agatctccta | caatattctc | 900 |
| agctgccatg | gaaaatcgat | gttcttcttt | tattctctca | agattttcag | gctgtatatt | 960 |
| aaaacttata | ttaagaacta | tgctaaccac | ctcatcagga | accgttgtag | gtggcgtggg | 1020 |
| ttttcttggc | aatcgactct | catgaaaact | acgagctaaa | tattcaatat | gttcctcttg | 1080 |
| accaacttta | ttctgcatt | ttttgaacg | aggtttagag | caagcttcag | gaaactgaga | 1140 |
| caggaatttt | attaaaaatt | taaattttga | agaaagttca | gggttaatag | catccatttt | 1200 |
| ttgctttgca | agttcctcag | cattcttaac | aaaagacgtc | tcttttgaca | tgtttaaagt | 1260 |
| ttaaacctcc | tgtgtgaaat | tattatccgc | tcataattcc | acacattata | cgagccggaa | 1320 |
| gcataaagtg | taaagcctgg | ggtgcctaat | gagtgagcta | actcacatta | attgcgttgc | 1380 |
| gctcactgcc | aattgctttc | cagtcgggaa | acctgtcgtg | ccagctgcat | taatgaatcg | 1440 |
| gccaacgcgc | ggggagaggc | ggtttgcgta | ttgggcgctc | ttccgcttcc | tcgctcactg | 1500 |
| actcgctgcg | ctcggtcgtt | cggctgcggc | gagcggtatc | agctcactca | aaggcggtaa | 1560 |
| tacggttatc | cacagaatca | ggggataacg | caggaaagaa | catgtgagca | aaaggccagc | 1620 |
| aaaaggccag | gaaccgtaaa | aaggccgcgt | tgctggcgtt | tttccatagg | ctccgccccc | 1680 |
| ctgacgagca | tcacaaaaat | cgacgctcaa | gtcagaggtg | gcgaaacccg | acaggactat | 1740 |
| aaagatacca | ggcgtttccc | cctggaagct | ccctcgtgcg | ctctcctgtt | ccgaccctgc | 1800 |
| cgcttaccgg | atacctgtcc | gcctttctcc | cttcgggaag | cgtggcgctt | tctcatagct | 1860 |
| cacgctgtag | gtatctcagt | tcggtgtagg | tcgttcgctc | caagctgggc | tgtgtgcacg | 1920 |

```
aacccccgt tcagcccgac cgctgcgcct tatccggtaa ctatcgtctt gagtccaacc    1980
cggtaagaca cgacttatcg ccactggcag cagccactgg taacaggatt agcagagcga    2040
ggtatgtagg cggtgctaca gagttcttga agtggtggcc taactacggc tacactagaa    2100
ggacagtatt tggtatctgc gctctgctga agccagttac cttcggaaaa agagttggta    2160
gctcttgatc cggcaaacaa accaccgctg gtagcggtgg ttttttttgtt tgcaagcagc    2220 agattacgcg cagaaaaaaa ggatctcaag aagatccttt gatcttttct acggggtctg    2280
acgctcagtg gaacgaaaac tcacgttaag ggattttggt catgagatta tcaaaaagga    2340
tcttcaccta gatcctttta aattaaaaat gaagttttaa atcaatctaa agtatatatg    2400
agtaaacttg gtctgacagt taccaatgct taatcagtga ggcacctatc tcagcgatct    2460
gtctatttcg ttcatccata gttgcctgac tccccgtcgt gtagataact acgatacggg    2520
agggcttacc atctggcccc agtgctgcaa tgataccgcg agacccacgc tcaccggctc    2580
cagatttatc agcaataaac cagccagccg gaagggccga gcgcagaagt ggtcctgcaa    2640
ctttatccgc ctccatccag tctattaatt gttgccggga agctagagta agtagttcgc    2700
cagttaatag tttgcgcaac gttgttgcca ttgctacagg catcgtggtg tcacgctcgt    2760
cgtttggtat ggcttcattc agctccggtt cccaacgatc aaggcgagtt acatgatccc    2820
ccatgttgtg caaaaaagcg gttagctcct tcggtcctcc gatcgttgtc agaagtaagt    2880
tggccgcagt gttatcactc atggttatgg cagcactgca taattctctt actgtcatgc    2940
catccgtaag atgcttttct gtgactggtg agtactcaac caagtcattc tgagaatagt    3000
gtatgcggcg accgagttgc tcttgcccgg cgtcaatacg ggataatacc gcgccacata    3060
gcagaacttt aaaagtgctc atcattggaa aacgttcttc ggggcgaaaa ctctcaagga    3120
tcttaccgct gttgagatcc agttcgatgt aacccactcg tgcacccaac tgatcttcag    3180
catcttttac tttcaccagc gtttctgggt gagcaaaaac aggaaggcaa aatgccgcaa    3240
aaaagggaat aagggcgaca cggaaatgtt gaatactcat actcttcctt tttcaatatt    3300
attgaagcat ttatcagggt tattgtctca tgagcggata catatttgaa tgtatttaga    3360
aaaataaaca aataggggtt ccgcgcacat ttccccgaaa agtgccacct gacgtctaag    3420
aaaccattat tatcatgaca ttaacctata aaaataggcg tatcacgagg cc            3472
```

<210> SEQ ID NO 64
<211> LENGTH: 498
<212> TYPE: DNA
<213> ORGANISM: Artificial Sequence
<220> FEATURE:
<223> OTHER INFORMATION: IFN-#\ GENE

<400> SEQUENCE: 64

```
tgcgatctgc cgcaaaccca cagtctggct cacacccgtg ccctgcgtct gctggcccaa     60
atgcgtcgta tctccccgtt cagttgtctg gatcatcgtc gcgactttgg ctctccgcac    120
gaagcattcg gcggtaacca ggtgcaaaaa gctcaggcga tggccctggt tcatgaaatg    180
ctgcagcaaa cctttcaact gttcagtacg gaaggctccg cggccgcatg ggatgaatca    240
ctgctgcacc agttttgcac cggtctggat cagcaactgc gtgacctgga agcatgtgtc    300
atgcaggaag ctggcctgga aggcacccg ctgctggaag aagattcgat tctggcggtg    360
cgtaaatatt tccatcgcct gacgctgtat ctgcaggaaa agagctactc tccgtgcgcg    420
tgggaaatcg ttcgcgccga agtgatgcgt tcgttctcgt caagccgtaa tctgcaagac    480
cgcctgcgta aaaaggaa                                                  498
```

<210> SEQ ID NO 65
<211> LENGTH: 66
<212> TYPE: DNA
<213> ORGANISM: Artificial Sequence
<220> FEATURE:
<223> OTHER INFORMATION: Synthetic: primer

<400> SEQUENCE: 65
caagccccgt ttttcaaaga aatcacgatc ctgaaagact acttcaatgc gtcaacctcc    60
gatgtc                                                              66

<210> SEQ ID NO 66
<211> LENGTH: 78
<212> TYPE: DNA
<213> ORGANISM: Artificial Sequence
<220> FEATURE:
<223> OTHER INFORMATION: Synthetic: primer

<400> SEQUENCE: 66
tcgctttctt ctttccagtt tttcaggatt tccaggaaca gcggaccacc attcgggaca    60
tcggaggttg acgcattg                                                 78

<210> SEQ ID NO 67
<211> LENGTH: 76
<212> TYPE: DNA
<213> ORGANISM: Artificial Sequence
<220> FEATURE:
<223> OTHER INFORMATION: Synthetic: primer

<400> SEQUENCE: 67
ctgaaaaact ggaaagaaga aagcgataag aaaattatcc agagtcaaat cgtctccttc    60
tacttcaaat ttttcg                                                   76

<210> SEQ ID NO 68
<211> LENGTH: 86
<212> TYPE: DNA
<213> ORGANISM: Artificial Sequence
<220> FEATURE:
<223> OTHER INFORMATION: Synthetic: primer

<400> SEQUENCE: 68
catgtcctgt ttaataacat ccatactacg ttggatcgcc tgattgtctt tgaagatttc    60 gaaaatttg aagtagaagg agacga                                         86

<210> SEQ ID NO 69
<211> LENGTH: 94
<212> TYPE: DNA
<213> ORGANISM: Artificial Sequence
<220> FEATURE:
<223> OTHER INFORMATION: Synthetic: primer

<400> SEQUENCE: 69
acgtagtatg gatgttatta aacaggacat gtttcagcgc ttcctgaacg gcagctctgg    60
taaactgaac gatttcgaaa aactgatcaa aatc                               94

<210> SEQ ID NO 70
<211> LENGTH: 73
<212> TYPE: DNA
<213> ORGANISM: Artificial Sequence
<220> FEATURE:
<223> OTHER INFORMATION: Synthetic: primer

```
<400> SEQUENCE: 70
cagttctgag atggctttac gttggatctg caggttgtcc accgggattt tgatcagttt    60
ttcgaaatcg ttc                                                       73

<210> SEQ ID NO 71
<211> LENGTH: 72
<212> TYPE: DNA
<213> ORGANISM: Artificial Sequence
<220> FEATURE:
<223> OTHER INFORMATION: Synthetic: primer

<400> SEQUENCE: 71
ccaacgtaaa gccatctcag aactgatcaa agttatgaac gatctgtcgc cgcgctccaa    60
tctgcgtaaa cg                                                        72

<210> SEQ ID NO 72
<211> LENGTH: 64
<212> TYPE: DNA
<213> ORGANISM: Artificial Sequence
<220> FEATURE:
<223> OTHER INFORMATION: Synthetic: primer

<400> SEQUENCE: 72
tttgctggca cgctgaccct ggaacatcgt ttgactacgt ttacgtttac gcagattgga    60
gcgc                                                                 64

<210> SEQ ID NO 73
<211> LENGTH: 21
<212> TYPE: DNA
<213> ORGANISM: Artificial Sequence
<220> FEATURE:
<223> OTHER INFORMATION: Synthetic: primer

<400> SEQUENCE: 73
caagccccgt ttttcaaaga a                                              21

<210> SEQ ID NO 74
<211> LENGTH: 18
<212> TYPE: DNA
<213> ORGANISM: Artificial Sequence
<220> FEATURE:
<223> OTHER INFORMATION: Synthetic: primer

<400> SEQUENCE: 74
tttgctggca cgctgacc                                                  18

<210> SEQ ID NO 75
<211> LENGTH: 3403
<212> TYPE: DNA
<213> ORGANISM: Artificial Sequence
<220> FEATURE:
<223> OTHER INFORMATION: Synthetic: plasmid

<400> SEQUENCE: 75
gcccctgcag ccgaattata ttattttgc caaataattt ttaacaaaag ctctgaagtc     60
ttcttcattt aaattcttag atgatacttc atctggaaaa ttgtcccaat tagtagcatc   120
acgctgtgag taagttctaa accattttt tattgttgta ttatctctaa tcttactact    180
cgatgagttt tcggtattat ctctattttt aacttggagc aggttccatt cattgttttt   240
ttcatcatag tgaataaaat caactgcttt aacacttgtg cctgaacacc atatccatcc   300
ggcgtaatac gactcactat agggagagcg gccgccagat cttccggatg gctcgagttt   360
```

```
ttcagcaaga ttttgctggc acgctgaccc tggaacatcg tttgactacg tttacgttta      420
cgcagattgg agcgcggcga cagatcgttc ataactttga tcagttctga gatggcttta      480
cgttggatct gcaggttgtc caccgggatt ttgatcagtt tttcgaaatc gttcagttta      540
ccagagctgc cgttcaggaa gcgctgaaac atgtcctgtt taataacatc catactacgt      600
tggatcgcct gattgtcttt gaagatttcg aaaaatttga agtagaagga gacgatttga      660
ctctggataa ttttcttatc gctttcttct ttccagtttt tcaggatttc caggaacagc      720
ggaccaccat tcgggacatc ggaggttgac gcattgaagt agtctttcag gatcgtgatt      780
tctttgaaaa acgggcttg atcttctag aagatctcct acaatattct cagctgccat       840
ggaaaatcga tgttcttctt ttattctctc aagattttca ggctgtatat taaaacttat      900
attaagaact atgctaacca cctcatcagg aaccgttgta ggtggcgtgg gttttcttgg      960
caatcgactc tcatgaaaac tacgagctaa atattcaata tgttcctctt gaccaacttt     1020
attctgcatt tttttgaac gaggtttaga gcaagcttca ggaaactgag acaggaattt      1080
tattaaaaat ttaaattttg aagaaagttc agggttaata gcatccattt tttgctttgc     1140
aagttcctca gcattcttaa caaaagacgt ctcttttgac atgtttaaag tttaaacctc     1200
ctgtgtgaaa ttattatccg ctcataattc cacacattat acgagccgga agcataaagt     1260
gtaaagcctg gggtgcctaa tgagtgagct aactcacatt aattgcgttg cgctcactgc     1320
caattgcttt ccagtcggga aacctgtcgt gccagctgca ttaatgaatc ggccaacgcg     1380
cggggagagg cggtttgcgt attgggcgct cttccgcttc ctcgctcact gactcgctgc     1440
gctcggtcgt tcggctgcgg cgagcggtat cagctcactc aaaggcggta atacggttat     1500
ccacagaatc aggggataac gcaggaaaga acatgtgagc aaaaggccag caaaaggcca     1560
ggaaccgtaa aaaggccgcg ttgctggcgt ttttccatag gctccgcccc cctgacgagc     1620
atcacaaaaa tcgacgctca agtcagaggt ggcgaaaccc gacaggacta taaagatacc     1680
aggcgtttcc ccctggaagc tccctcgtgc gctctcctgt tccgaccctg ccgcttaccg     1740
gatacctgtc cgcctttctc ccttcgggaa gcgtggcgct ttctcatagc tcacgctgta     1800
ggtatctcag ttcggtgtag tcgttcgct ccaagctggg ctgtgtgcac gaaccccccg      1860
ttcagcccga ccgctgcgcc ttatccggta actatcgtct tgagtccaac ccggtaagac     1920
acgacttatc gccactggca gcagccactg gtaacaggat tagcagagcg aggtatgtag     1980
gcggtgctac agagttcttg aagtggtggc ctaactacgg ctacactaga aggacagtat     2040
ttggtatctg cgctctgctg aagccagtta ccttcggaaa aagagttggt agctcttgat     2100
ccggcaaaca aaccaccgct ggtagcggtg gtttttttgt ttgcaagcag cagattacgc     2160
gcagaaaaaa aggatctcaa gaagatcctt tgatctttc tacggggtct gacgctcagt      2220
ggaacgaaaa ctcacgttaa gggattttgg tcatgagatt atcaaaaagg atcttcacct     2280
agatcctttt aaattaaaaa tgaagtttta aatcaatcta agtatatat gagtaaactt      2340 ggtctgacag ttaccaatgc ttaatcagtg aggcacctat ctcagcgatc tgtctatttc     2400
gttcatccat agttgcctga ctccccgtcg tgtagataac tacgatacgg agggcttac      2460 catctggccc cagtgctgca atgataccgc gagacccacg ctcaccggct ccagatttat     2520
cagcaataaa ccagccagcc ggaagggccg agcgcagaag tggtcctgca actttatccg     2580
cctccatcca gtctattaat tgttgccggg aagctagagt aagtagttcg ccagttaata     2640
gtttgcgcaa cgttgttgcc attgctacag gcatcgtggt gtcacgctcg tcgtttggta     2700
```

| | |
|---|---|
| tggcttcatt cagctccggt tcccaacgat caaggcgagt tacatgatcc cccatgttgt | 2760 |
| gcaaaaaagc ggttagctcc ttcggtcctc cgatcgttgt cagaagtaag ttggccgcag | 2820 |
| tgttatcact catggttatg gcagcactgc ataattctct tactgtcatg ccatccgtaa | 2880 |
| gatgcttttc tgtgactggt gagtactcaa ccaagtcatt ctgagaatag tgtatgcggc | 2940 |
| gaccgagttg ctcttgcccg cgtcaatac gggataatac cgcgccacat agcagaactt | 3000 |
| taaaagtgct catcattgga aaacgttctt cggggcgaaa actctcaagg atcttaccgc | 3060 |
| tgttgagatc cagttcgatg taacccactc gtgcacccaa ctgatcttca gcatctttta | 3120 |
| ctttcaccag cgtttctggg tgagcaaaaa caggaaggca aaatgccgca aaaaagggaa | 3180 |
| taagggcgac acggaaatgt tgaatactca tactcttcct ttttcaatat tattgaagca | 3240 |
| tttatcaggg ttattgtctc atgagcggat acatatttga atgtatttag aaaaataaac | 3300 |
| aaataggggt tccgcgcaca tttccccgaa aagtgccacc tgacgtctaa gaaaccatta | 3360 |
| ttatcatgac attaacctat aaaaataggc gtatcacgag gcc | 3403 |

<210> SEQ ID NO 76
<211> LENGTH: 429
<212> TYPE: DNA
<213> ORGANISM: Artificial Sequence
<220> FEATURE:
<223> OTHER INFORMATION: IFN-GENE

<400> SEQUENCE: 76

| | |
|---|---|
| caagccccgt ttttcaaaga aatcacgatc ctgaaagact acttcaatgc gtcaacctcc | 60 |
| gatgtcccga atggtggtcc gctgttcctg gaaatcctga aaaactggaa agaagaaagc | 120 |
| gataagaaaa ttatccagag tcaaatcgtc tccttctact tcaaattttt cgaaatcttc | 180 |
| aaagacaatc aggcgatcca acgtagtatg gatgttatta acaggacat gtttcagcgc | 240 |
| ttcctgaacg gcagctctgg taaactgaac gatttcgaaa aactgatcaa aatcccggtg | 300 |
| gacaacctgc agatccaacg taaagccatc tcagaactga tcaaagttat gaacgatctg | 360 |
| tcgccgcgct ccaatctgcg taaacgtaaa cgtagtcaaa cgatgttcca gggtcagcgt | 420 |
| gccagcaaa | 429 |

<210> SEQ ID NO 77
<211> LENGTH: 30
<212> TYPE: DNA
<213> ORGANISM: Artificial Sequence
<220> FEATURE:
<223> OTHER INFORMATION: Synthetic: primer

<400> SEQUENCE: 77

| | |
|---|---|
| caatatcata tgtgcgatct gccgcaaacc | 30 |

<210> SEQ ID NO 78
<211> LENGTH: 57
<212> TYPE: DNA
<213> ORGANISM: Artificial Sequence
<220> FEATURE:
<223> OTHER INFORMATION: Synthetic: primer

<400> SEQUENCE: 78

| | |
|---|---|
| gatatagtcg acttattagt gatggtgatg gtgatgttcc tttttacgca ggcggtc | 57 |

<210> SEQ ID NO 79
<211> LENGTH: 5784
<212> TYPE: DNA
<213> ORGANISM: Artificial Sequence
<220> FEATURE:
<223> OTHER INFORMATION: Synthetic: plasmid

<400> SEQUENCE: 79

```
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacttatta gtgatggtga tggtgatgtt ccttttttacg caggcggtct tgcagattac    240
ggcttgacga gaacgaacgc atcacttcgg cgcgaacgat ttcccacgcg cacggagagt     300
agctcttttc ctgcagatac agcgtcaggc gatggaaata tttacgcacc gccagaatcg    360
aatcttcttc cagcagcggg gtgccttcca ggccagcttc ctgcatgaca catgcttcca    420
ggtcacgcag ttgctgatcc agaccggtgc aaaactggtg cagcagtgat tcatcccatg    480
cggccgcgga gccttccgta ctgaacagtt gaaaggtttg ctgcagcatt tcatgaacca    540
gggccatcgc ctgagctttt tgcacctggt taccgccgaa tgcttcgtgc ggagagccaa    600
agtcgcgacg atgatccaga caactgaacg gggagatacg acgcatttgg ccagcagac    660
gcagggcacg ggtgtgagcc agactgtggg tttgcggcag atcgcacata tgtatatctc    720
cttcttaaag ttaaacaaaa ttatttctag aggggaattg ttatccgctc acaattcccc    780
tatagtgagt cgtattaatt tcgcgggatc gagatcgatc tcgatcctct acgccggacg    840
catcgtggcc ggcatcaccg cgccacaggt gcggttgct ggcgcctata tcgccgacat    900
caccgatggg gaagatcggg ctcgccactt cgggctcatg agcgcttgtt tcggcgtggg    960
tatggtggca ggccccgtgg ccgggggact gttgggcgcc atctccttgc atgcaccatt   1020
ccttgcggcg gcggtgctca acggcctcaa cctactactg ggctgcttcc taatgcagga   1080
gtcgcataag ggagagcgtc gagatcccgg acaccatcga atggcgcaaa acctttcgcg   1140
gtatggcatg atagcgcccg gaagagagtc aattcagggt ggtgaatgtg aaaccagtaa   1200
cgttatacga tgtcgcagag tatgccggtg tctcttatca gaccgtttcc cgcgtggtga   1260
accaggccag ccacgtttct gcgaaaacgc gggaaaaagt ggaagcggcg atggcggagc   1320
tgaattacat tcccaaccgc gtggcacaac aactggcggg caaacagtcg ttgctgattg   1380
gcgttgccac ctccagtctg gccctgcacg cgccgtcgca aattgtcgcg gcgattaaat   1440
ctcgcgccga tcaactgggt gccagcgtgg tggtgtcgat ggtagaacga agcggcgtcg   1500
aagcctgtaa agcggcggtg cacaatcttc tcgcgcaacg cgtcagtggg ctgatcatta   1560
actatccgct ggatgaccag gatgccattg ctgtggaagc tgcctgcact aatgttccgg   1620
cgttatttct tgatgtctct gaccagacac ccatcaacag tattattttc tcccatgaag   1680
acggtacgcg actgggcgtg gagcatctgg tcgcattggg tcaccagcaa atcgcgctgt   1740
tagcgggccc attaagttct gtctcggcgc gtctgcgtct ggctggctgg cataaatatc   1800
tcactcgcaa tcaaattcag ccgatagcgg aacgggaagg cgactggagt gccatgtccg   1860
gttttcaaca aaccatgcaa atgctgaatg agggcatcgt tcccactgcg atgctggttg   1920
ccaacgatca gatggcgctg ggcgcaatgc gcgccattac cgagtccggg ctgcgcgttg   1980
gtgcggacat ctcggtagtg ggatacgacg ataccgaaga cagctcatgt tatatcccgc   2040
cgttaaccac catcaaacag gattttcgcc tgctgggca aaccagcgtg gaccgcttgc    2100
tgcaactctc tcagggccag gcggtgaagg gcaatcagct gttgcccgtc tcactggtga   2160
aaagaaaaac cacccctggcg cccaatacgc aaaccgcctc tccccgcgcg ttggccgatt   2220
```

-continued

```
cattaatgca gctggcacga caggtttccc gactggaaag cgggcagtga gcgcaacgca    2280
attaatgtaa gttagctcac tcattaggca ccgggatctc gaccgatgcc cttgagagcc    2340
ttcaacccag tcagctcctt ccggtgggcg cggggcatga ctatcgtcgc cgcacttatg    2400
actgtcttct ttatcatgca actcgtagga caggtgccgg cagcgctctg ggtcattttc    2460
ggcgaggacc gctttcgctg gagcgcgacg atgatcggcc tgtcgcttgc ggtattcgga    2520
atcttgcacg ccctcgctca agccttcgtc actggtcccg ccaccaaacg tttcggcgag    2580
aagcaggcca ttatcgccgg catggcggcc ccacgggtgc gcatgatcgt gctcctgtcg    2640
ttgaggaccc ggctaggctg gcggggttgc cttactggtt agcagaatga atcaccgata    2700
cgcgagcgaa cgtgaagcga ctgctgctgc aaaacgtctg cgacctgagc aacaacatga    2760
atggtcttcg gtttccgtgt ttcgtaaagt ctggaaacgc ggaagtcagc gccctgcacc    2820
attatgttcc ggatctgcat cgcaggatgc tgctggctac cctgtggaac acctacatct    2880
gtattaacga agcgctggca ttgaccctga gtgattttc tctggtcccg ccgcatccat    2940
accgccagtt gtttaccctc acaacgttcc agtaaccggg catgttcatc atcagtaacc    3000
cgtatcgtga gcatcctctc tcgtttcatc ggtatcatta cccccatgaa cagaaatccc    3060
ccttacacgg aggcatcagt gaccaaacag gaaaaaaccg cccttaacat ggcccgcttt    3120
atcagaagcc agacattaac gcttctggag aaactcaacg agctggacgc ggatgaacag    3180
gcagacatct gtgaatcgct tcacgaccac gctgatgagc tttaccgcag ctgcctcgcg    3240
cgtttcggtg atgacggtga aaacctctga cacatgcagc tcccggagac ggtcacagct    3300
tgtctgtaag cggatgccgg gagcagacaa gcccgtcagg gcgcgtcagc gggtgttggc    3360
gggtgtcggg gcgcagccat gacccagtca cgtagcgata gcggagtgta tactggctta    3420
actatgcgga tcagagcag attgtactga gagtgcacca tatatgcggt gtgaaatacc    3480
gcacagatgc gtaaggagaa ataccgcat caggcgctct ccgcttcct cgctcactga    3540 ctcgctgcgc tcggtcgttc ggctgcggcg agcggtatca gctcactcaa aggcggtaat    3600
acggttatcc acagaatcag gggataacgc aggaaagaac atgtgagcaa aaggccagca    3660
aaaggccagg aaccgtaaaa aggccgcgtt gctggcgttt ttccataggc tccgcccccc    3720
tgacgagcat cacaaaaatc gacgctcaag tcagaggtgg cgaaacccga caggactata    3780
aagataccag gcgtttcccc ctggaagctc cctcgtgcgc tctcctgttc cgaccctgcc    3840
gcttaccgga tacctgtccg cctttctccc ttcgggaagc gtggcgcttt ctcatagctc    3900
acgctgtagg tatctcagtt cggtgtaggt cgttcgctcc aagctgggct gtgtgcacga    3960 acccccgtt cagcccgacc gctgcgcctt atccggtaac tatcgtcttg agtccaaccc    4020
ggtaagacac gacttatcgc cactggcagc agccactggt aacaggatta gcagagcgag    4080
gtatgtaggc ggtgctacag agttcttgaa gtggtggcct aactacggct acactagaag    4140
gacagtattt ggtatctgcg ctctgctgaa gccagttacc ttcggaaaaa gagttggtag    4200
ctcttgatcc ggcaaacaaa ccaccgctgg tagcggtggt ttttttgttt gcaagcagca    4260
gattacgcgc agaaaaaaag gatctcaaga agatcctttg atcttttcta cggggtctga    4320
cgctcagtgg aacgaaaact cacgttaagg gattttggtc atgaacaata aaactgtctg    4380
cttacataaa cagtaataca aggggtgtta tgagccatat tcaacgggaa acgtcttgct    4440
ctaggccgcg attaaattcc aacatggatg ctgatttata tgggtataaa tgggctcgcg    4500
ataatgtcgg gcaatcaggt gcgacaatct atcgattgta tgggaagccc gatgcgccag    4560
agttgtttct gaaacatggc aaaggtagcg ttgccaatga tgttacagat gagatggtca    4620
```

```
gactaaactg gctgacggaa tttatgcctc ttccgaccat caagcatttt atccgtactc    4680
ctgatgatgc atggttactc accactgcga tccccgggaa aacagcattc caggtattag    4740
aagaatatcc tgattcaggt gaaaatattg ttgatgcgct ggcagtgttc ctgcgccggt    4800
tgcattcgat tcctgtttgt aattgtcctt ttaacagcga tcgcgtattt cgtctcgctc    4860
aggcgcaatc acgaatgaat aacggtttgg ttgatgcgag tgattttgat gacgagcgta    4920
atggctggct gttgaacaa gtctggaaag aaatgcataa acttttgcca ttctcaccgg     4980
attcagtcgt cactcatggt gatttctcac ttgataacct tattttgac gagggaaat      5040 taataggttg tattgatgtt ggacgagtcg gaatcgcaga ccgataccag gatcttgcca    5100
tcctatggaa ctgcctcggt gagttttctc cttcattaca gaaacggctt tttcaaaaat    5160
atggtattga taatcctgat atgaataaat tgcagtttca tttgatgctc gatgagtttt    5220
tctaagaatt aattcatgag cggatacata tttgaatgta tttagaaaaa taaacaaata    5280
ggggttccgc gcacatttcc ccgaaaagtg ccacctgaaa ttgtaaacgt taatattttg    5340
ttaaaattcg cgttaaattt ttgttaaatc agctcatttt ttaaccaata ggccgaaatc    5400
ggcaaaatcc cttataaatc aaaagaatag accgagatag ggttgagtgt tgttccagtt    5460
tggaacaaga gtccactatt aaagaacgtg gactccaacg tcaaagggcg aaaaaccgtc    5520
tatcagggcg atggcccact acgtgaacca tcaccctaat caagtttttt ggggtcgagg    5580
tgccgtaaag cactaaatcg gaaccctaaa gggagccccc gatttagagc ttgacgggga    5640
aagccggcga acgtggcgag aaaggaaggg aagaaagcga aaggagcggg cgctagggcg    5700
ctggcaagtg tagcggtcac gctgcgcgta accaccacac ccgccgcgct taatgcgccg    5760
ctacagggcg cgtcccattc gcca                                           5784
```

<210> SEQ ID NO 80
<211> LENGTH: 4154
<212> TYPE: DNA
<213> ORGANISM: Artificial Sequence
<220> FEATURE:
<223> OTHER INFORMATION: Synthetic: plasmid

<400> SEQUENCE: 80

```
ggtaccaaag catgcaatga gctcagtaac ccgtatcgtg agcatcctct ctcgtttcat      60
cggtatcatt accccccatga acagaaatcc cccttacacg gaggcatcag tgaccaaaca     120
ggaaaaaacc gcccttaaca tggcccgctt tatcagaagc cagacattaa cgcttctgga     180
gaaactcaac gagctggacg cggatgaaca ggcagacatc tgtgaatcgc ttcacgacca     240
cgctgatgag ctttaccgca gctgcctcgc gcgtttcggt gatgacggtg aaaacctctg     300
acacatgcag ctcccggaga cggtcacagc ttgtctgtaa gcggatgccg ggagcagaca     360
agcccgtcag ggcgcgtcag cgggtgttgg cgggtgtcgg ggcgcagcca tgacccagtc     420
acgtagcgat agcggagtgt atactggctt aactatgcgg catcagagca gattgtactg     480
agagtgcacc attcgcggtgt gaaataccgc acagatgcgt aaggagaaaa taccgcatca     540
ggcgctcttc cgcttcctcg ctcactgact cgctgcgctc ggtcgttcgg ctgcggcgag     600
cggtatcagc tcactcaaag gcggtaatac ggttatccac agaatcaggg gataacgcag     660
gaaagaacat gtgagcaaaa ggccagcaaa aggccaggaa ccgtaaaaag gccgcgttgc     720
tggcgttttt ccataggctc cgcccccctg acgagcatca caaaaatcga cgctcaagtc     780
agaggtggcg aaacccgaca ggactataaa gataccaggc gtttccccct ggaagctccc     840
```

```
tcgtgcgctc tcctgttccg acccctgccgc ttaccggata cctgtccgcc tttctccctt    900
cgggaagcgt ggcgctttct catagctcac gctgtaggta tctcagttcg gtgtaggtcg    960
ttcgctccaa gctgggctgt gtgcacgaac cccccgttca gcccgaccgc tgcgccttat   1020
ccggtaacta tcgtcttgag tccaacccgg taagacacga cttatcgcca ctggcagcag   1080
ccactggtaa caggattagc agagcgaggt atgtaggcgg tgctacagag ttcttgaagt   1140
ggtggcctaa ctacggctac actagaagga cagtatttgg tatctgcgct ctgctgaagc   1200
cagttacctt cggaaaaaga gttggtagct cttgatccgg caaacaaacc accgctggta   1260
gcggtggttt ttttgtttgc aagcagcaga ttacgcgcag aaaaaaagga tctcaagaag   1320
atcctttgat cttttctacg gggtctgacg ctcagtggaa cgaaaactca cgttaaggga   1380
ttttggtcat gaacaataaa actgtctgct tacataaaca gtaatacaag gggtgttatg   1440
agccatatca acgggaaacg ctcgagtacg tatctagagc aaagcttatc gtcgacttat   1500
tagtgatggt gatggtgatg ttcctttta cgcaggcggt cttgcagatt acggcttgac   1560
gagaacgaac gcatcacttc ggcgcgaacg atttcccacg cgcacggaga gtagctcttt   1620
tcctgcagat acagcgtcag gcgatggaaa tatttacgca ccgccagaat cgaatcttct   1680
tccagcagcg gggtgccttc caggccagct tcctgcatga cacatgcttc caggtcacgc   1740
agttgctgat ccagaccggt gcaaaactgg tgcagcagtg attcatccca tgcggccgcg   1800
gagccttccg tactgaacag ttgaaaggtt tgctgcagca tttcatgaac cagggccatc   1860
gcctgagctt tttgcacctg gttaccgccg aatgcttcgt gcggagagcc aaagtcgcga   1920
cgatgatcca gacaactgaa cggggagata cgacgcattt gggccagcag acgcagggca   1980
cgggtgtgag ccagactgtg ggtttgcggc agatcgcaca tatgtattcc tccttcttaa   2040
agttaaacaa aaaaacgggt atggagaaac agtagcaagt tgcgataaaa agcgtcaggt   2100
aggatccgct aatcttatgg ataaaaatgc tatggcatag caaagtgtga cgccgtgcaa   2160
ataatcaatg tggacttttc tgccgtgatt atagacactt tgttacgcg tttttgtcat   2220
ggctttggtc ccgctttgtt acagaatgct tttaataagc ggggttaccg gtttggttag   2280
cgagaagagc cagtaaaaga cgcagtgacg gcaatgtctg atgcaatatg gacaattggt   2340
ttcttctctg aatggcggga gtatgaaaag tatggctgaa gcgcaaaatg atcccctgct   2400
gccgggatac tcgtttaatg cccatctggt ggcgggttta acgccgattg aggccaacgg   2460
ttatctcgat ttttttatcg accgaccgct gggaatgaaa ggttatattc tcaatctcac   2520
cattcgcgt caggggggtgg tgaaaaatca gggacgagaa tttgtttgcc gaccgggtga   2580
tatttgctg ttcccgccag gagagattca tcactacggt cgtcatccgg aggctcgcga   2640
atggtatcac cagtgggttt actttcgtcc gcgcgcctac tggcatgaat ggcttaactg   2700
gccgtcaata tttgccaata cggggttctt tcgcccggat gaagcgcacc agccgcattt   2760
cagcgacctg tttgggcaaa tcattaacgc cgggcaaggg gaagggcgct attcggagct   2820
gctggcgata aatctgcttg agcaattgtt actgcgcgc atggaagcga ttaacgagtc   2880
gctccatcca ccgatggata atcgggtacg cgaggcttgt cagtacatca gcgatcacct   2940
ggcagacagc aattttgata tcgccagcgt cgcacagcat gtttgcttgt cgccgtcgcg   3000
tctgtcacat cttttccgcc agcagttagg gattagcgtc ttaagctggc gcgaggacca   3060
acgtatcagc caggcgaagc tgcttttgag caccacccgg atgcctatcg ccaccgtcgg   3120
tcgcaatgtt ggttttgacg atcaactcta tttctcgcgg gtatttaaaa aatgcaccgg   3180
ggccagcccg agcgagttcc gtgccggttg tgaagaaaaa gtgaatgatg tagccgtcaa   3240
```

```
gttgtcataa ttggtaacga atcagacaat tgacggcttg acggagtagc atagggtttg    3300
cagaatccct gcttcgtcca tttgacaggc acattatgcg aattcgctag cagatcttag    3360
tgacattaga aaaccgactg taaaaagtac agtcggcatt atctcatatt ataaaagcca    3420
gtcattaggc ctatctgaca attcctgaat agagttcata acaatcctg catgataacc     3480 atcacaaaca gaatgatgta cctgtaaaga tagcggtaaa tatattgaat tacctttatt    3540
aatgaatttt cctgctgtaa taatgggtag aaggtaatta ctattattat tgatatttaa    3600
gttaaaccca gtaaatgaag tccatggaat aatagaaaga gaaaaagcat tttcaggtat    3660
aggtgttttg ggaaacaatt tccccgaacc attatatttc tctacatcag aaaggtataa    3720
atcataaaac tctttgaagt cattctttac aggagtccaa ataccagaga atgttttaga    3780
tacaccatca aaaattgtat aaagtggctc taacttatcc caataaccta actctccgtc    3840
gctattgtaa ccagttctaa aagctgtatt tgagtttatc accctggtca ctaagaaaat    3900
aaatgcaggg taaaatttat atccttcttg ttttatgttt cggtataaaa cactaatatc    3960
aatttctgtg gttatactaa aagtcgtttg ttggttcaaa taatgattaa atatctcttt    4020
tctcttccaa ttgtctaaat caattttatt aaagttcatt tgatatgcct cctaaatttt    4080
tatctaaagt gaatttagga ggcttacttg tctgctttct tcattagaat caatccttt     4140 ttaaaagtca atcc                                                      4154

<210> SEQ ID NO 81
<211> LENGTH: 24
<212> TYPE: DNA
<213> ORGANISM: Artificial Sequence
<220> FEATURE:
<223> OTHER INFORMATION: Synthetic: primer

<400> SEQUENCE: 81
accaccaatc tgttctctgt gagc                                           24

<210> SEQ ID NO 82
<211> LENGTH: 42
<212> TYPE: DNA
<213> ORGANISM: Artificial Sequence
<220> FEATURE:
<223> OTHER INFORMATION: Synthetic: primer

<400> SEQUENCE: 82
gctcacagag aacagattgg tggttgcgat ctgccgcaaa cc                       42

<210> SEQ ID NO 83
<211> LENGTH: 6138
<212> TYPE: DNA
<213> ORGANISM: Artificial Sequence
<220> FEATURE:
<223> OTHER INFORMATION: Synthetic: plasmid

<400> SEQUENCE: 83
atccggatat agttcctcct ttcagcaaaa aacccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttatta gtgatggtga tggtgatgtt cctttttacg caggcggtct tgcagattac    240
ggcttgacga gaacgaacgc atcacttcgg cgcgaacgat tcccacgcg cacggagagt     300 agctcttttc ctgcagatac agcgtcaggc gatggaaata tttacgcacc gccagaatcg    360
```

```
aatcttcttc cagcagcggg gtgccttcca ggccagcttc ctgcatgaca catgcttcca    420
ggtcacgcag ttgctgatcc agaccggtgc aaaactggtg cagcagtgat tcatcccatg    480
cggccgcgga gccttccgta ctgaacagtt gaaaggtttg ctgcagcatt tcatgaacca    540
gggccatcgc ctgagctttt tgcacctggt taccgccgaa tgcttcgtgc ggagagccaa    600
agtcgcgacg atgatccaga caactgaacg gggagatacg acgcatttgg ccagcagac    660 gcagggcacg ggtgtgagcc agactgtggg tttgcggcag atcgcaacca ccaatctgtt    720
ctctgtgagc ctcaataata tcgttatcct ccatgtccaa atcttcaggg gtctgatcag    780
cttgaattct aataccgtcg tacaagaatc ttaaggagtc catttcctta ccctgtcttt    840
tagcgaacgc ttccatcagc cttcttaaag gagtggtctt tttgatctta aagaagattt    900
ctgaagatcc atcggacacc tttaaattga tgtgagtctc aggcttgact tctggcttga    960
cctctggctt agcttcttga ttgacttctg agtccgacat ggtacccaga tctgggctgt   1020
ccatgtgctg gcgttcgaat ttagcagcag cggtttcttt catatgtata tctccttctt   1080
aaagttaaac aaaattattt ctagagggga attgttatcc gctcacaatt ccctatagt    1140 gagtcgtatt aatttcgcgg gatcgagatc gatctcgatc ctctacgccg gacgcatcgt   1200
ggccggcatc accggcgcca caggtgcggt tgctggcgcc tatatcgccg acatcaccga   1260
tggggaagat cgggctcgcc acttcgggct catgagcgct tgtttcggcg tgggtatggt   1320
ggcaggcccc gtggccgggg gactgttggg cgccatctcc ttgcatgcac cattccttgc   1380
ggcggcggtg ctcaacggcc tcaacctact actgggctgc ttcctaatgc aggagtcgca   1440
taagggagag cgtcgagatc ccggacacca tcgaatggcg caaaaccttt cgcggtatgg   1500
catgatagcg cccggaagag agtcaattca gggtggtgaa tgtgaaacca gtaacgttat   1560
acgatgtcgc agagtatgcc ggtgtctctt atcagaccgt ttcccgcgtg gtgaaccagg   1620
ccagccacgt ttctgcgaaa acgcgggaaa aagtggaagc ggcgatggcg gagctgaatt   1680
acattcccaa ccgcgtggca caacaactgg cgggcaaaca gtcgttgctg attggcgttg   1740
ccacctccag tctggccctg cacgcgccgt cgcaaattgt cgcggcgatt aaatctcgcg   1800
ccgatcaact gggtgccagc gtggtggtgt cgatggtaga acgaagcggc gtcgaagcct   1860
gtaaagcggc ggtgcacaat cttctcgcgc aacgcgtcag tgggctgatc attaactatc   1920
cgctggatga ccaggatgcc attgctgtgg aagctgcctg cactaatgtt ccggcgttat   1980
ttcttgatgt ctctgaccag acacccatca acagtattat tttctcccat gaagacggta   2040
cgcgactggg cgtggagcat ctggtcgcat gggtcacca gcaaatcgcg ctgttagcgg   2100
gcccattaag ttctgtctcg gcgcgtctgc gtctggctgg ctggcataaa tatctcactc   2160
gcaatcaaat tcagccgata gcggaacggg aaggcgactg gagtgccatg tccggttttc   2220
aacaaaccat gcaaatgctg aatgagggca tcgttcccac tgcgatgctg gttgccaacg   2280 atcgatggc gctgggcgca atgcgcgcca ttaccgagtc cgggctgcgc gttggtgcgg   2340
acatctcggt agtgggatac gacgataccg aagacagctc atgttatatc ccgccgttaa   2400
ccaccatcaa acaggatttt cgcctgctgg ggcaaaccag cgtggaccgc ttgctgcaac   2460
tctctcaggg ccaggcggtg aagggcaatc agctgttgcc cgtctcactg gtgaaaagaa   2520
aaaccaccct ggcgcccaat acgcaaaccg cctctcccg cgcgttggcc gattcattaa   2580
tgcagctggc acgacaggtt tcccgactgg aaagcgggca gtgagcgcaa cgcaattaat   2640
gtaagttagc tcactcatta ggcaccggga tctcgaccga tgcccttgag agccttcaac   2700
ccagtcagct ccttccggtg ggcgcggggc atgactatcg tcgccgcact tatgactgtc   2760
```

```
ttctttatca tgcaactcgt aggacaggtg ccggcagcgc tctgggtcat tttcggcgag    2820
gaccgctttc gctggagcgc gacgatgatc ggcctgtcgc ttgcggtatt cggaatcttg    2880
cacgccctcg ctcaagcctt cgtcactggt cccgccacca aacgtttcgg cgagaagcag    2940
gccattatcg ccggcatggc ggccccacgg gtgcgcatga tcgtgctcct gtcgttgagg    3000
acccggctag gctggcgggg ttgccttact ggttagcaga atgaatcacc gatacgcgag    3060
cgaacgtgaa gcgactgctg ctgcaaaacg tctgcgacct gagcaacaac atgaatggtc    3120
ttcggtttcc gtgtttcgta aagtctggaa acgcggaagt cagcgccctg caccattatg    3180
ttccggatct gcatcgcagg atgctgctgg ctaccctgtg gaacacctac atctgtatta    3240
acgaagcgct ggcattgacc ctgagtgatt tttctctggt cccgccgcat ccataccgcc    3300
agttgtttac cctcacaacg ttccagtaac cgggcatgtt catcatcagt aacccgtatc    3360
gtgagcatcc tctctcgttt catcggtatc attaccccca tgaacagaaa tccccttac    3420
acggaggcat cagtgaccaa acaggaaaaa accgcccta acatggcccg ctttatcaga    3480
agccagacat taacgcttct ggagaaactc aacgagctgg acgcggatga acaggcagac    3540
atctgtgaat cgcttcacga ccacgctgat gagctttacc gcagctgcct cgcgcgtttc    3600
ggtgatgacg gtgaaaacct ctgacacatg cagctcccgg agacggtcac agcttgtctg    3660
taagcggatg ccgggagcag acaagcccgt caggggcgcgt cagcgggtgt tggcgggtgt    3720
cggggcgcag ccatgaccca gtcacgtagc gatagcggag tgtatactgg cttaactatg    3780
cggcatcaga gcagattgta ctgagagtgc accatatatg cggtgtgaaa taccgcacag    3840
atgcgtaagg agaaaatacc gcatcaggcg ctcttccgct tcctcgctca ctgactcgct    3900
gcgctcggtc gttcggctgc ggcgagcgg atcagctcac tcaaaggcgg taatacggtt    3960
atccacagaa tcaggggata acgcaggaaa gaacatgtga gcaaaaggcc agcaaaaggc    4020
caggaaccgt aaaaaggccg cgttgctggc gtttttccat aggctccgcc ccctgacga    4080
gcatcacaaa aatcgacgct caagtcagag gtggcgaaac ccgacaggac tataaagata    4140
ccaggcgttt ccccctggaa gctccctcgt gcgctctcct gttccgaccc tgccgcttac    4200
cggatacctg tccgcctttc tcccttcggg aagcgtggcg ctttctcata gctcacgctg    4260
taggtatctc agttcggtgt aggtcgttcg ctccaagctg ggctgtgtgc acgaaccccc    4320
cgttcagccc gaccgctgcg ccttatccgg taactatcgt cttgagtcca acccggtaag    4380
acacgactta tcgccactgg cagcagccac tggtaacagg attagcagag cgaggtatgt    4440
aggcggtgct acagagttct tgaagtggtg gcctaactac ggctacacta aggacagt    4500
atttggtatc tgcgctctgc tgaagccagt taccttcgga aaaagagttg gtagctcttg    4560
atccggcaaa caaccaccg ctggtagcgg tggtttttt gtttgcaagc agcagattac    4620
gcgcagaaaa aaaggatctc aagaagatcc tttgatcttt tctacggggt ctgacgctca    4680
gtggaacgaa aactcacgtt aagggatttt ggtcatgaac aataaaactg tctgcttaca    4740
taaacagtaa tacaagggt gttatgagcc atattcaacg ggaaacgtct gctctaggc    4800
cgcgattaaa ttccaacatg gatgctgatt tatatgggta aaatgggct cgcgataatg    4860
tcgggcaatc aggtgcgaca atctatcgat tgtatgggaa gcccgatgcg ccagagttgt    4920
ttctgaaaca tggcaaaggt agcgttgcca atgatgttac agatgagatg gtcagactaa    4980
actggctgac ggaattttatg cctcttccga ccatcaagca ttttatccgt actcctgatg    5040
atgcatggtt actcaccact gcgatccccg ggaaaacagc attccaggta ttagaagaat    5100
```

```
atcctgattc aggtgaaaat attgttgatg cgctggcagt gttcctgcgc cggttgcatt    5160
cgattcctgt ttgtaattgt ccttttaaca gcgatcgcgt atttcgtctc gctcaggcgc    5220
aatcacgaat gaataacggt ttggttgatg cgagtgattt tgatgacgag cgtaatggct    5280
ggcctgttga acaagtctgg aaagaaatgc ataaactttt gccattctca ccggattcag    5340
tcgtcactca tggtgatttc tcacttgata accttatttt tgacgagggg aaattaatag    5400
gttgtattga tgttggacga gtcggaatcg cagaccgata ccaggatctt gccatccctat   5460 ggaactgcct cggtgagttt tctccttcat tacagaaacg gcttttcaa aaatatggta    5520 ttgataatcc tgatatgaat aaattgcagt ttcatttgat gctcgatgag tttttctaag    5580
aattaattca tgagcggata catatttgaa tgtatttaga aaaataaaca aataggggtt    5640
ccgcgcacat ttccccgaaa agtgccacct gaaattgtaa acgttaatat tttgttaaaa    5700
ttcgcgttaa attttgtta atcagctca ttttttaacc aataggccga aatcggcaaa     5760
atcccttata aatcaaaaga atagaccgag atagggttga gtgttgttcc agtttggaac    5820
aagagtccac tattaaagaa cgtggactcc aacgtcaaag ggcgaaaaac cgtctatcag    5880
ggcgatggcc cactacgtga accatcaccc taatcaagtt ttttggggtc gaggtgccgt    5940
aaagcactaa atcggaaccc taaagggagc ccccgattta gagcttgacg gggaaagccg    6000
gcgaacgtgg cgagaaagga agggaagaaa gcgaaaggag cgggcgctag ggcgctggca    6060
agtgtagcgg tcacgctgcg cgtaaccacc acccgccg cgcttaatgc gccgctacag     6120
ggcgcgtccc attcgcca                                                 6138
```

<210> SEQ ID NO 84
<211> LENGTH: 19
<212> TYPE: DNA
<213> ORGANISM: Artificial Sequence
<220> FEATURE:
<223> OTHER INFORMATION: Synthetic: primer

<400> SEQUENCE: 84

```
gccgccgatt tgttcacgg                                                  19
```

<210> SEQ ID NO 85
<211> LENGTH: 37
<212> TYPE: DNA
<213> ORGANISM: Artificial Sequence
<220> FEATURE:
<223> OTHER INFORMATION: Synthetic: primer

<400> SEQUENCE: 85

```
ccgtgaacaa atcggcggct gcgatctgcc gcaaacc                              37
```

<210> SEQ ID NO 86
<211> LENGTH: 6138
<212> TYPE: DNA
<213> ORGANISM: Artificial Sequence
<220> FEATURE:
<223> OTHER INFORMATION: Synthetic: plasmid

<400> SEQUENCE: 86

```
atccggatat agttcctcct ttcagcaaaa aaccccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttatta gtgatggtga tggtgatgtt ccttttacg caggcggtct tgcagattac     240
ggcttgacga gaacgaacgc atcacttcgg cgcgaacgat ttcccacgcg cacggagagt    300
```

```
agctcttttc ctgcagatac agcgtcaggc gatggaaata tttacgcacc gccagaatcg    360
aatcttcttc cagcagcggg gtgccttcca ggccagcttc ctgcatgaca catgcttcca    420
ggtcacgcag ttgctgatcc agaccggtgc aaaactggtg cagcagtgat tcatcccatg    480
cggccgcgga gccttccgta ctgaacagtt gaaaggtttg ctgcagcatt tcatgaacca    540
gggccatcgc ctgagctttt tgcacctggt taccgccgaa tgcttcgtgc ggagagccaa    600
agtcgcgacg atgatccaga caactgaacg gggagatacg acgcatttgg gccagcagac    660
gcagggcacg ggtgtgagcc agactgtggg tttgcggcag atcgcagccg ccgatttgtt    720
cacggtgtgt tcgataatg tcgttgtctt ccatgtccag gtcttccggg gtttgatccg    780
cctggatgcg aataccgtca tacaggaaac gcagactatc catttccttg ccctgacgtt    840
tggcaaacgc ttccatcagg cgacgcagcg gcgtggtctt tttgatctta agaaaatttt    900
cagagctgcc gtcactaact ttcaggttga tgtgggtttc cggtttcact tccggtttca    960
cttccggttt cgcttcttgg ttcacttcgc tatcgctcat ggtacccaga tctgggctgt   1020
ccatgtgctg gcgttcgaat ttagcagcag cggtttcttt catatgtata tctccttctt   1080
aaagttaaac aaaattattt ctagagggga attgttatcc gctcacaatt ccctatagt    1140 gagtcgtatt aatttcgcgg gatcgagatc gatctcgatc ctctacgccg gacgcatcgt   1200
ggccggcatc accggcgcca caggtgcggt tgctggcgcc tatatcgccg acatcaccga   1260
tggggaagat cgggctcgcc acttcgggct catgagcgct tgtttcggcg tgggtatggt   1320
ggcaggcccc gtggccgggg gactgttggg cgccatctcc ttgcatgcac cattccttgc   1380
ggcggcggtg ctcaacggcc tcaacctact actgggctgc ttcctaatgc aggagtcgca   1440
taagggagag cgtcgagatc ccggacacca tcgaatggcg caaaaccttt cgcggtatgg   1500
catgatagcg cccggaagag agtcaattca gggtggtgaa tgtgaaacca gtaacgttat   1560
acgatgtcgc agagtatgcc ggtgtctctt atcagaccgt ttcccgcgtg gtgaaccagg   1620
ccagccacgt ttctgcgaaa acgcgggaaa aagtggaagc ggcgatggcg gagctgaatt   1680
acattcccaa ccgcgtggca caacaactgg cgggcaaaca gtcgttgctg attggcgttg   1740
ccacctccag tctggccctg cacgcgccgt cgcaaattgt cgcggcgatt aaatctcgcg   1800
ccgatcaact gggtgccagc gtggtggtgt cgatggtaga acgaagcggc gtcgaagcct   1860
gtaaagcggc ggtgcacaat cttctcgcgc aacgcgtcag tgggctgatc attaactatc   1920
cgctggatga ccaggatgcc attgctgtgg aagctgcctg cactaatgtt ccggcgttat   1980
ttcttgatgt ctctgaccag acacccatca acagtattat tttctcccat gaagacggta   2040
cgcgactggg cgtggagcat ctggtcgcat tgggtcacca gcaaatcgcg ctgttagcgg   2100
gcccattaag ttctgtctcg gcgcgtctgc gtctggctgg ctggcataaa tatctcactc   2160
gcaatcaaat tcagccgata gcggaacggg aaggcgactg gagtgccatg tccggttttc   2220
aacaaaccat gcaaatgctg aatgagggca tcgttcccac tgcgatgctg gttgccaacg   2280
atcagatggc gctgggcgca atgcgcgcca ttaccgagtc cgggctgcgc gttggtgcgg   2340
acatctcggt agtgggatac gacgataccg aagacagctc atgttatatc ccgccgttaa   2400
ccaccatcaa acaggatttt cgcctgctgg ggcaaaccag cgtggaccgc ttgctgcaac   2460
tctctcaggg ccaggcggtg aagggcaatc agctgttgcc cgtctcactg gtgaaaagaa   2520
aaaccaccct ggcgcccaat acgcaaaccg cctctccccg cgcgttggcc gattcattaa   2580
tgcagctggc acgacaggtt tcccgactgg aaagcgggca gtgagcgcaa cgcaattaat   2640
```

```
gtaagttagc tcactcatta ggcaccggga tctcgaccga tgcccttgag agccttcaac   2700
ccagtcagct ccttccggtg ggcgcggggc atgactatcg tcgccgcact tatgactgtc   2760
ttctttatca tgcaactcgt aggacaggtg ccggcagcgc tctgggtcat tttcggcgag   2820
gaccgctttc gctggagcgc gacgatgatc ggcctgtcgc ttgcggtatt cggaatcttg   2880
cacgccctcg ctcaagcctt cgtcactggt cccgccacca aacgtttcgg cgagaagcag   2940
gccattatcg ccggcatggc ggccccacgg gtgcgcatga tcgtgctcct gtcgttgagg   3000
acccggctag gctggcgggg ttgccttact ggttagcaga atgaatcacc gatacgcgag   3060
cgaacgtgaa gcgactgctg ctgcaaaacg tctgcgacct gagcaacaac atgaatggtc   3120
ttcggtttcc gtgtttcgta aagtctggaa acgcggaagt cagcgccctg caccattatg   3180
ttccggatct gcatcgcagg atgctgctgg ctaccctgtg gaacacctac atctgtatta   3240
acgaagcgct ggcattgacc ctgagtgatt tttctctggt cccgccgcat ccataccgcc   3300
agttgtttac cctcacaacg ttccagtaac cgggcatgtt catcatcagt aacccgtatc   3360
gtgagcatcc tctctcgttt catcggtatc attacccccca tgaacagaaa tcccccttac   3420
acggaggcat cagtgaccaa acaggaaaaa accgccctta acatggcccg ctttatcaga   3480
agccagacat taacgcttct ggagaaactc aacgagctgg acgcggatga acaggcagac   3540
atctgtgaat cgcttcacga ccacgctgat gagctttacc gcagctgcct cgcgcgtttc   3600
ggtgatgacg gtgaaaacct ctgacacatg cagctcccgg agacggtcac agcttgtctg   3660
taagcggatg ccgggagcag acaagcccgt cagggcgcgt cagcgggtgt tggcgggtgt   3720
cggggcgcag ccatgaccca gtcacgtagc gatagcggag tgtatactgg cttaactatg   3780
cggcatcaga gcagattgta ctgagagtgc accatatatg cggtgtgaaa taccgcacag   3840
atgcgtaagg agaaaatacc gcatcaggcg ctcttccgct tcctcgctca ctgactcgct   3900
gcgctcggtc gttcggctgc ggcgagcggt atcagctcac tcaaaggcgg taatacggtt   3960
atccacagaa tcaggggata acgcaggaaa gaacatgtga gcaaaaggcc agcaaaaggc   4020
caggaaccgt aaaaaggccg cgttgctggc gtttttccat aggctccgcc cccctgacga   4080
gcatcacaaa aatcgacgct caagtcagag gtggcgaaac ccgacaggac tataaagata   4140
ccaggcgttt ccccctggaa gctccctcgt gcgctctcct gttccgaccc tgccgcttac   4200
cggatacctg tccgcctttc tcccttcggg aagcgtggcg ctttctcata gctcacgctg   4260
taggtatctc agttcggtgt aggtcgttcg ctccaagctg ggctgtgtgc acgaaccccc   4320
cgttcagccc gaccgctgcg ccttatccgg taactatcgt cttgagtcca acccggtaag   4380
acacgactta tcgccactgg cagcagccac tggtaacagg attagcagag cgaggtatgt   4440
aggcggtgct acagagttct tgaagtggtg gcctaactac ggctacacta aaggacagt    4500 atttggtatc tgcgctctgc tgaagccagt taccttcgga aaaagagttg gtagctcttg   4560
atccggcaaa caaaccaccg ctggtagcgg tggttttttt gtttgcaagc agcagattac   4620
gcgcagaaaa aaaggatctc aagaagatcc tttgatcttt tctacggggt ctgacgctca   4680
gtggaacgaa aactcacgtt aagggatttt ggtcatgaac aataaaactg tctgcttaca   4740
taaacagtaa tacaaggggt gttatgagcc atattcaacg ggaaacgtct tgctctaggc   4800
cgcgattaaa ttccaacatg gatgctgatt tatatgggta taaatgggct cgcgataatg   4860
tcgggcaatc aggtgcgaca atctatcgat tgtatgggaa gcccgatgcg ccagagttgt   4920
ttctgaaaca tggcaaaggt agcgttgcca atgatgttac agatgagatg gtcagactaa   4980
actggctgac ggaatttatg cctcttccga ccatcaagca ttttatccgt actcctgatg   5040
```

| | | |
|---|---|---|
| atgcatggtt actcaccact gcgatccccg ggaaaacagc attccaggta ttagaagaat | 5100 |
| atcctgattc aggtgaaaat attgttgatg cgctggcagt gttcctgcgc cggttgcatt | 5160 |
| cgattcctgt ttgtaattgt ccttttaaca gcgatcgcgt atttcgtctc gctcaggcgc | 5220 |
| aatcacgaat gaataacggt ttggttgatg cgagtgattt tgatgacgag cgtaatggct | 5280 |
| ggcctgttga acaagtctgg aaagaaatgc ataaactttt gccattctca ccggattcag | 5340 |
| tcgtcactca tggtgatttc tcacttgata accttatttt tgacgagggg aaattaatag | 5400 |
| gttgtattga tgttggacga gtcggaatcg cagaccgata ccaggatctt gccatcctat | 5460 |
| ggaactgcct cggtgagttt tctccttcat tacagaaacg ctttttcaa aaatatggta | 5520 |
| ttgataatcc tgatatgaat aaattgcagt tcatttgat gctcgatgag ttttttctaag | 5580 |
| aattaattca tgagcggata catatttgaa tgtatttaga aaaataaaca aatagggggtt | 5640 |
| ccgcgcacat ttccccgaaa agtgccacct gaaattgtaa acgttaatat tttgttaaaa | 5700 |
| ttcgcgttaa attttgtta aatcagctca ttttttaacc aataggccga aatcggcaaa | 5760 |
| atcccttata aatcaaaaga atagaccgag atagggttga gtgttgttcc agtttggaac | 5820 |
| aagagtccac tattaaagaa cgtggactcc aacgtcaaag ggcgaaaaac cgtctatcag | 5880 |
| ggcgatggcc cactacgtga accatcaccc taatcaagtt ttttgggggtc gaggtgccgt | 5940 |
| aaagcactaa atcggaaccc taagggagc ccccgattta gagcttgacg gggaaagccg | 6000 |
| gcgaacgtgg cgagaaagga agggaagaaa gcgaaaggag cgggcgctag ggcgctggca | 6060 |
| agtgtagcgg tcacgctgcg cgtaaccacc acacccgccg cgcttaatgc gccgctacag | 6120 |
| ggcgcgtccc attcgcca | 6138 |

<210> SEQ ID NO 87
<211> LENGTH: 4508
<212> TYPE: DNA
<213> ORGANISM: Artificial Sequence
<220> FEATURE:
<223> OTHER INFORMATION: Synthetic: plasmid

<400> SEQUENCE: 87

| | | |
|---|---|---|
| ggtaccaaag catgcaatga gctcagtaac ccgtatcgtg agcatcctct ctcgtttcat | 60 |
| cggtatcatt accccccatga acagaaatcc cccttacacg gaggcatcag tgaccaaaca | 120 |
| ggaaaaaacc gcccttaaca tggcccgctt tatcagaagc cagacattaa cgcttctgga | 180 |
| gaaactcaac gagctggacg cggatgaaca ggcagacatc tgtgaatcgc ttcacgacca | 240 |
| cgctgatgag ctttaccgca gctgcctcgc gcgtttcggt gatgacggtg aaaacctctg | 300 |
| acacatgcag ctcccggaga cggtcacagc ttgtctgtaa gcggatgccg ggagcagaca | 360 |
| agcccgtcag ggcgcgtcag cgggtgttgg cgggtgtcgg ggcgcagcca tgacccagtc | 420 |
| acgtagcgat agcggagtgt atactggctt aactatgcgg catcagagca gattgtactg | 480 |
| agagtgcacc attgcggtgt gaaataccgc acagatgcgt aaggagaaaa taccgcatca | 540 |
| ggcgctcttc cgcttcctcg ctcactgact cgctgcgctc ggtcgttcgg ctgcggcgag | 600 |
| cggtatcagc tcactcaaag gcggtaatac ggttatccac agaatcaggg gataacgcag | 660 |
| gaaagaacat gtgagcaaaa ggccagcaaa aggccaggaa ccgtaaaaag gccgcgttgc | 720 |
| tggcgttttt ccataggctc cgcccccctg acgagcatca caaaaatcga cgctcaagtc | 780 |
| agaggtggcg aaacccgaca ggactataaa gataccaggc gtttccccct ggaagctccc | 840 |
| tcgtgcgctc tcctgttccg accctgccgc ttaccggata cctgtccgcc tttctccctt | 900 |

```
cgggaagcgt ggcgctttct catagctcac gctgtaggta tctcagttcg gtgtaggtcg    960
ttcgctccaa gctgggctgt gtgcacgaac ccccgttca gcccgaccgc tgcgccttat    1020
ccggtaacta tcgtcttgag tccaacccgg taagacacga cttatcgcca ctggcagcag    1080
ccactggtaa caggattagc agagcgaggt atgtaggcgg tgctacagag ttcttgaagt    1140
ggtggcctaa ctacggctac actagaagga cagtatttgg tatctgcgct ctgctgaagc    1200
cagttacctt cggaaaaaga gttggtagct cttgatccgg caaacaaacc accgctggta    1260
gcggtggttt ttttgtttgc aagcagcaga ttacgcgcag aaaaaaagga tctcaagaag    1320
atcctttgat cttttctacg gggtctgacg ctcagtggaa cgaaaactca cgttaaggga    1380
ttttggtcat gaacaataaa actgtctgct tacataaaca gtaatacaag gggtgttatg    1440
agccatatca acgggaaacg ctcgagtacg tatctagagc aaagcttatc gtcgacttat    1500
tagtgatggt gatggtgatg ttccttttta cgcaggcggt cttgcagatt acggcttgac    1560
gagaacgaac gcatcacttc ggcgcgaacg atttcccacg cgcacggaga gtagctcttt    1620
tcctgcagat acagcgtcag gcgatggaaa tatttacgca ccgccagaat cgaatcttct    1680
tccagcagcg gggtgccttc caggccagct cctgcatga cacatgcttc caggtcacgc    1740
agttgctgat ccagaccggt gcaaaactgg tgcagcagtg attcatccca tgcggccgcg    1800
gagccttccg tactgaacag ttgaaaggtt tgctgcagca tttcatgaac cagggccatc    1860
gcctgagctt tttgcacctg gttaccgccg aatgcttcgt gcgagagcc aaagtcgcga    1920 cgatgatcca gacaactgaa cggggagata cgacgcattt gggccagcag acgcagggca    1980
cgggtgtgag ccagactgtg ggtttgcggc agatcgcagc cgccgatttg ttcacggtgt    2040
gcttcgataa tgtcgttgtc ttccatgtcc aggtcttccg gggtttgatc cgcctggatg    2100
cgaataccgt catacaggaa acgcagacta tccatttcct tgccctgacg tttggcaaac    2160
gcttccatca ggcgacgcag cggcgtggtc ttttgatct taaagaaaat ttcagagctg    2220
ccgtcactaa ctttcaggtt gatgtgggtt tccggtttca cttccggttt cacttccggt    2280
ttcgcttctt ggttcacttc gctatcgctc atggtaccca gatctgggct gtccatgtgc    2340
tggcgttcga atttagcagc agcggttttct ttcatatgta ttcctccttc ttaaagttaa    2400
acaaaaaaac gggtatggag aaacagtagc aagttgcgat aaaaagcgtc aggtaggatc    2460
cgctaatctt atggataaaa atgctatggc atagcaaagt gtgacgccgt gcaaataatc    2520
aatgtggact tttctgccgt gattatagac acttttgtta cgcgttttg tcatggcttt    2580 ggtcccgctt tgttacagaa tgcttttaat aagcggggtt accggtttgg ttagcgagaa    2640
gagccagtaa aagacgcagt gacggcaatg tctgatgcaa tatggacaat tggtttcttc    2700
tctgaatggc gggagtatga aaagtatggc tgaagcgcaa aatgatcccc tgctgccggg    2760
atactcgttt aatgcccatc tggtggcggg tttaacgccg attgaggcca acggttatct    2820 cgatttttt atcgaccgac cgctgggaat gaaaggttat attctcaatc tcaccattcg    2880
cggtcagggg gtggtgaaaa atcagggacg agaatttgtt tgccgaccgg gtgatatttt    2940
gctgttcccg ccaggagaga ttcatcacta cggtcgtcat ccggaggctc gcgaatggta    3000
tcaccagtgg gttactttc gtccgcgcgc ctactggcat gaatggctta actggccgtc    3060
aatatttgcc aatacggggt tctttcgccc ggatgaagcg caccagccgc atttcagcga    3120
cctgtttggg caaatcatta acgcggggca aggggaaggg cgctattcgg agctgctggc    3180
gataaatctg cttgagcaat tgttactgcg gcgcatggaa gcgattaacg agtcgctcca    3240
tccaccgatg gataatcggg tacgcgaggc ttgtcagtac atcagcgatc acctggcaga    3300
```

```
cagcaatttt gatatcgcca gcgtcgcaca gcatgtttgc ttgtcgccgt cgcgtctgtc    3360
acatcttttc cgccagcagt tagggattag cgtcttaagc tggcgcgagg accaacgtat    3420
cagccaggcg aagctgcttt tgagcaccac ccggatgcct atcgccaccg tcggtcgcaa    3480
tgttggtttt gacgatcaac tctatttctc gcgggtattt aaaaaatgca ccggggccag    3540
cccgagcgag ttccgtgccg gttgtgaaga aaaagtgaat gatgtagccg tcaagttgtc    3600
ataattggta acgaatcaga caattgacgg cttgacggag tagcataggg tttgcagaat    3660
ccctgcttcg tccatttgac aggcacatta tgcgaattcg ctagcagatc ttagtgacat    3720
tagaaaaccg actgtaaaaa gtacagtcgg cattatctca tattataaaa gccagtcatt    3780
aggcctatct gacaattcct gaatagagtt cataaacaat cctgcatgat aaccatcaca    3840
aacagaatga tgtacctgta aagatagcgg taaatatatt gaattacctt tattaatgaa    3900
ttttcctgct gtaataatgg gtagaaggta attactatta ttattgatat ttaagttaaa    3960
cccagtaaat gaagtccatg gaataataga aagagaaaaa gcattttcag gtataggtgt    4020
tttgggaaac aatttccccg aaccattata tttctctaca tcagaaaggt ataaatcata    4080
aaactctttg aagtcattct ttacaggagt ccaaatacca gagaatgttt tagatacacc    4140
atcaaaaatt gtataaagtg gctctaactt atcccaataa cctaactctc cgtcgctatt    4200
gtaaccagtt ctaaaagctg tatttgagtt tatcacccct tgtcactaaga aaataaatgc    4260 agggtaaaat ttatatcctt cttgttttat gtttcggtat aaaacactaa tatcaatttc    4320
tgtggttata ctaaaagtcg tttgttggtt caaataatga ttaaatatct cttttctctt    4380
ccaattgtct aaatcaattt tattaaagtt catttgatat gcctcctaaa ttttttatcta    4440 aagtgaattt aggaggctta cttgtctgct ttcttcatta gaatcaatcc ttttttaaaa    4500
gtcaatcc                                                            4508

<210> SEQ ID NO 88
<211> LENGTH: 33
<212> TYPE: DNA
<213> ORGANISM: Artificial Sequence
<220> FEATURE:
<223> OTHER INFORMATION: Synthetic: primer

<400> SEQUENCE: 88
caatatcata tgcaagcccc gttttttcaaa gaa                                 33

<210> SEQ ID NO 89
<211> LENGTH: 54
<212> TYPE: DNA
<213> ORGANISM: Artificial Sequence
<220> FEATURE:
<223> OTHER INFORMATION: Synthetic: primer

<400> SEQUENCE: 89
gatatagtcg acttattagt gatggtgatg gtgatgtttg ctggcacgct gacc          54

<210> SEQ ID NO 90
<211> LENGTH: 5715
<212> TYPE: DNA
<213> ORGANISM: Artificial Sequence
<220> FEATURE:
<223> OTHER INFORMATION: Synthetic: plasmid

<400> SEQUENCE: 90
atccggatat agttcctcct ttcagcaaaa aaccccctcaa gacccgttta gaggccccaa    60
```

-continued

```
ggggttatgc tagttattgc tcagcgtgg cagcagccaa ctcagcttcc tttcgggctt      120
tgttagcagc cggatctcag tggtggtggt ggtggtgctc gagtgcggcc gcaagcttgt     180
cgacttatta gtgatggtga tggtgatgtt tgctggcacg ctgaccctgg aacatcgttt     240
gactacgttt acgtttacgc agattggagc gcggcgacag atcgttcata actttgatca    300
gttctgagat ggctttacgt tggatctgca ggttgtccac cgggattttg atcagttttt    360
cgaaatcgtt cagtttacca gagctgccgt tcaggaagcg ctgaaacatg tcctgtttaa    420
taacatccat actacgttgg atcgcctgat tgtctttgaa gatttcgaaa aatttgaagt    480
agaaggagac gatttgactc tggataattt tcttatcgct ttcttctttc cagttttca    540 ggatttccag gaacagcgga ccaccattcg ggacatcgga ggttgacgca ttgaagtagt    600
ctttcaggat cgtgatttct ttgaaaaacg gggcttgcat atgtatatct ccttcttaaa    660
gttaaacaaa attatttcta gaggggaatt gttatccgct cacaattccc ctatagtgag    720
tcgtattaat ttcgcgggat cgagatcgat ctcgatcctc tacgccggac gcatcgtggc    780
cggcatcacc ggcgccacag gtgcggttgc tggcgcctat atcgccgaca tcaccgatgg    840
ggaagatcgg gctcgccact tcgggctcat gagcgcttgt ttcggcgtgg gtatggtggc    900
aggccccgtg gccgggggac tgttgggcgc catctccttg catgcaccat tccttgcggc    960
ggcggtgctc aacggcctca acctactact gggctgcttc ctaatgcagg agtcgcataa   1020
gggagagcgt cgagatcccg gacaccatcg aatggcgcaa aacctttcgc ggtatggcat   1080
gatagcgccc ggaagagagt caattcaggg tggtgaatgt gaaaccagta acgttatacg   1140
atgtcgcaga gtatgccggt gtctcttatc agaccgtttc ccgcgtggtg aaccaggcca   1200
gccacgtttc tgcgaaaacg cgggaaaaag tggaagcggc gatggcggag ctgaattaca   1260
ttcccaaccg cgtggcacaa caactggcgg caaacagtc gttgctgatt ggcgttgcca    1320
cctccagtct ggccctgcac gcgccgtcgc aaattgtcgc ggcgattaaa tctcgcgccg   1380
atcaactggg tgccagcgtg gtggtgtcga tggtagaacg aagcggcgtc gaagcctgta   1440
aagcggcggt gcacaatctt ctcgcgcaac gcgtcagtgg gctgatcatt aactatccgc   1500
tggatgacca ggatgccatt gctgtggaag ctgcctgcac taatgttccg gcgttatttc   1560
ttgatgtctc tgaccagaca cccatcaaca gtattatttt ctcccatgaa gacggtacgc   1620
gactgggcgt ggagcatctg gtcgcattgg gtcaccagca atcgcgctg ttagcgggcc    1680 cattaagttc tgtctcggcg cgtctgcgtc tggctggctg gcataaatat ctcactcgca   1740
atcaaattca gccgatagcg gaacgggaag gcgactggag tgccatgtcc ggttttcaac   1800
aaaccatgca aatgctgaat gagggcatcg ttcccactgc gatgctggtt gccaacgatc   1860
agatggcgct gggcgcaatg cgcgccatta ccgagtccgg gctgcgcgtt ggtgcggaca   1920
tctcggtagt gggatacgac gataccgaag acagctcatg ttatatcccg ccgttaacca   1980
ccatcaaaca ggattttcgc ctgctggggc aaaccagcgt ggaccgcttg ctgcaactct   2040
ctcagggcca ggcggtgaag gcaatcagc tgttgcccgt ctcactggtg aaaagaaaaa    2100
ccaccctggc gcccaatacg caaaccgcct ctccccgcgc gttggccgat tcattaatgc   2160
agctggcacg acaggtttcc cgactggaaa gcgggcagtg agcgcaacgc aattaatgta   2220
agttagctca ctcattaggc accgggatct cgaccgatgc ccttgagagc cttcaaccca   2280
gtcagctcct tccggtgggc gcggggcatg actatcgtcg ccgcacttat gactgtcttc   2340
tttatcatgc aactcgtagg acaggtgccg gcagcgctct gggtcatttt cggcgaggac   2400
cgctttcgct ggagcgcgac gatgatcggc ctgtcgcttg cggtattcgg aatcttgcac   2460
```

```
gccctcgctc aagccttcgt cactggtccc gccaccaaac gtttcggcga gaagcaggcc      2520
attatcgccg gcatggcggc cccacggtg cgcatgatcg tgctcctgtc gttgaggacc        2580
cggctaggct ggcggggttg ccttactggt tagcagaatg aatcaccgat acgcgagcga      2640
acgtgaagcg actgctgctg caaaacgtct gcgacctgag caacaacatg aatggtcttc      2700
ggtttccgtg tttcgtaaag tctggaaacg cggaagtcag cgccctgcac cattatgttc      2760
cggatctgca tcgcaggatg ctgctggcta ccctgtggaa cacctacatc tgtattaacg      2820
aagcgctggc attgaccctg agtgattttt ctctggtccc gccgcatcca taccgccagt      2880
tgtttaccct cacaacgttc cagtaaccgg gcatgttcat catcagtaac ccgtatcgtg      2940
agcatcctct ctcgtttcat cggtatcatt acccccatga acagaaatcc cccttacacg      3000
gaggcatcag tgaccaaaca ggaaaaaacc gcccttaaca tgcccgctt tatcagaagc       3060 cagacattaa cgcttctgga gaaactcaac gagctggacg cggatgaaca ggcagacatc      3120
tgtgaatcgc ttcacgacca cgctgatgag ctttaccgca gctgcctcgc gcgtttcggt      3180
gatgacggtg aaaacctctg acacatgcag ctcccggaga cggtcacagc ttgtctgtaa      3240
gcggatgccg ggagcagaca agcccgtcag ggcgcgtcag cgggtgttgg cgggtgtcgg      3300
ggcgcagcca tgacccagtc acgtagcgat agcggagtgt atactggctt aactatgcgg      3360
catcagagca gattgtactg agagtgcacc atatatgcgg tgtgaaatac cgcacagatg      3420
cgtaaggaga aaataccgca tcaggcgctc ttccgcttcc tcgctcactg actcgctgcg      3480
ctcggtcgtt cggctgcggc gagcggtatc agctcactca aaggcggtaa tacggttatc      3540
cacagaatca ggggataacg caggaaagaa catgtgagca aaaggccagc aaaaggccag      3600
gaaccgtaaa aaggccgcgt tgctggcgtt tttccatagg ctccgccccc ctgacgagca      3660
tcacaaaaat cgacgctcaa gtcagaggtg gcgaaacccg acaggactat aaagatacca      3720
ggcgtttccc cctggaagct ccctcgtgcg ctctcctgtt ccgaccctgc cgcttaccgg      3780
atacctgtcc gcctttctcc cttcgggaag cgtggcgctt tctcatagct cacgctgtag      3840
gtatctcagt tcggtgtagg tcgttcgctc caagctgggc tgtgtgcacg aaccccccgt      3900
tcagcccgac cgctgcgcct tatccggtaa ctatcgtctt gagtccaacc cggtaagaca      3960
cgacttatcg ccactggcag cagccactgg taacaggatt agcagagcga ggtatgtagg      4020
cggtgctaca gagttcttga agtggtggcc taactacggc tacactagaa ggacagtatt      4080
tggtatctgc gctctgctga agccagttac cttcggaaaa agagttggta gctcttgatc      4140
cggcaaacaa accaccgctg gtagcggtgg tttttttgtt tgcaagcagc agattacgcg      4200
cagaaaaaaa ggatctcaag aagatccttt gatcttttct acggggtctg acgctcagtg      4260
gaacgaaaac tcacgttaag ggattttggt catgaacaat aaaactgtct gcttacataa      4320
acagtaatac aagggggtgtt atgagccata ttcaacggga acgtcttgc tctaggccgc      4380 gattaaattc caacatggat gctgatttat atgggtataa atgggctcgc gataatgtcg      4440
ggcaatcagg tgcgacaatc tatcgattgt atgggaagcc cgatgcgcca gagttgtttc      4500
tgaaacatgg caaaggtagc gttgccaatg atgttacaga tgagatggtc agactaaact      4560
ggctgacgga atttatgcct cttccgacca tcaagcattt tatccgtact cctgatgatg      4620
catggttact caccactgcg atccccggga aaacagcatt ccaggtatta gaagaatatc      4680
ctgattcagt gaaaatatt gttgatgcgc tggcagtgtt cctgcgccgg ttgcattcga      4740
ttcctgtttg taattgtcct tttaacagcg atcgcgtatt tcgtctcgct caggcgcaat      4800
```

```
cacgaatgaa taacggtttg gttgatgcga gtgattttga tgacgagcgt aatggctggc    4860
ctgttgaaca agtctggaaa gaaatgcata aacttttgcc attctcaccg gattcagtcg    4920
tcactcatgg tgatttctca cttgataacc ttattttga cgaggggaaa ttaataggtt     4980
gtattgatgt tggacgagtc ggaatcgcag accgatacca ggatcttgcc atcctatgga    5040
actgcctcgg tgagttttct ccttcattac agaaacggct ttttcaaaaa tatggtattg    5100
ataatcctga tatgaataaa ttgcagtttc atttgatgct cgatgagttt ttctaagaat    5160
taattcatga gcggatacat atttgaatgt atttagaaaa ataaacaaat aggggttccg    5220
cgcacatttc cccgaaaagt gccacctgaa attgtaaacg ttaatatttt gttaaaattc    5280
gcgttaaatt tttgttaaat cagctcattt tttaaccaat aggccgaaat cggcaaaatc    5340
ccttataaat caaagaata gaccgagata gggttgagtg ttgttccagt ttggaacaag     5400
agtccactat taagaacgt ggactccaac gtcaaagggc gaaaaaccgt ctatcagggc     5460
gatggcccac tacgtgaacc atcacccta tcaagttttt tggggtcgag gtgccgtaaa    5520
gcactaaatc ggaaccctaa agggagcccc cgatttagag cttgacgggg aaagccggcg    5580
aacgtggcga gaaaggaagg gaagaaagcg aaaggagcgg gcgctagggc gctggcaagt    5640
gtagcggtca cgctgcgcgt aaccaccaca cccgccgcgc ttaatgcgcc gctacagggc    5700
gcgtcccatt cgcca                                                    5715

<210> SEQ ID NO 91
<211> LENGTH: 45
<212> TYPE: DNA
<213> ORGANISM: Artificial Sequence
<220> FEATURE:
<223> OTHER INFORMATION: Synthetic: primer

<400> SEQUENCE: 91
gctcacagag aacagattgg tggtcaagcc ccgttttca aagaa                      45

<210> SEQ ID NO 92
<211> LENGTH: 6069
<212> TYPE: DNA
<213> ORGANISM: Artificial Sequence
<220> FEATURE:
<223> OTHER INFORMATION: Synthetic: plasmid

<400> SEQUENCE: 92
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt    180
cgacttatta gtgatggtga tggtgatgtt tgctggcacg ctgaccctgg aacatcgttt    240
gactacgttt acgtttacgc agattggagc gcggcgacag atcgttcata actttgatca    300
gttctgagat ggctttacgt tggatctgca ggttgtccac cgggattttg atcagttttt    360
cgaaatcgtt cagtttacca gagctgccgt tcaggaagcg ctgaaacatg tcctgtttaa    420
taacatccat actacgttgg atcgcctgat tgtctttgaa gatttcgaaa aatttgaagt    480
agaaggagac gatttgactc tggataattt tcttatcgct ttcttctttc cagtttttca    540 ggattccag gaacagcgga ccaccattcg ggacatcgga ggttgacgca ttgaagtagt      600 cttcaggat cgtgatttct ttgaaaaacg gggcttgacc accaatctgt tctctgtgag       660
cctcaataat atcgttatcc tccatgtcca aatcttcagg ggtctgatca gcttgaattc      720
taataccgtc gtacaagaat cttaaggagt ccatttcctt accctgtctt ttagcgaacg     780
```

```
cttccatcag ccttcttaaa ggagtggtct ttttgatctt aaagaagatt tctgaagatc      840
catcggacac ctttaaattg atgtgagtct caggcttgac ttctggcttg acctctggct      900
tagcttcttg attgacttct gagtccgaca tggtacccag atctgggctg tccatgtgct      960
ggcgttcgaa tttagcagca gcggtttctt tcatatgtat atctccttct taaagttaaa     1020
caaaattatt tctagagggg aattgttatc cgctcacaat tcccctatag tgagtcgtat     1080
taatttcgcg ggatcgagat cgatctcgat cctctacgcc ggacgcatcg tggccggcat     1140
caccggcgcc acaggtgcgg ttgctggcgc ctatatcgcc gacatcaccg atggggaaga     1200
tcgggctcgc cacttcgggc tcatgagcgc ttgtttcggc gtgggtatgg tggcaggccc     1260
cgtggccggg ggactgttgg gcgccatctc cttgcatgca ccattccttg cggcggcggt     1320
gctcaacggc ctcaacctac tactgggctg cttcctaatg caggagtcgc ataaggagag     1380
gcgtcgagat cccggacacc atcgaatggc gcaaaacctt cgcggtatg gcatgatagc      1440 gcccggaaga gagtcaattc agggtggtga atgtgaaacc agtaacgtta tacgatgtcg     1500
cagagtatgc cggtgtctct tatcagaccg tttcccgcgt ggtgaaccag gccagccacg     1560
tttctgcgaa aacgcgggaa aaagtggaag cggcgatggc ggagctgaat tacattccca     1620
accgcgtggc acaacaactg gcgggcaaac agtcgttgct gattggcgtt gccacctcca     1680
gtctggccct gcacgcgccg tcgcaaattg tcgcggcgat taaatctcgc gccgatcaac     1740
tgggtgccag cgtggtggtg tcgatggtag aacgaagcgg cgtcgaagcc tgtaaagcgg     1800
cggtgcacaa tcttctcgcg caacgcgtca gtgggctgat cattaactat ccgctggatg     1860
accaggatgc cattgctgtg gaagctgcct gcactaatgt tccggcgtta tttcttgatg     1920
tctctgacca gacacccatc aacagtatta ttttctccca tgaagacggt acgcgactgg     1980
gcgtggagca tctggtcgca ttgggtcacc agcaaatcgc gctgttagcg ggcccattaa     2040
gttctgtctc ggcgcgtctg cgtctggctg gctggcataa atatctcact cgcaatcaaa     2100
ttcagccgat agcggaacgg gaaggcgact ggagtgccat gtccggtttt caacaaacca     2160
tgcaaatgct gaatgagggc atcgttccca ctgcgatgct ggttgccaac gatcagatgg     2220
cgctgggcgc aatgcgcgcc attaccgagt ccgggctgcg cgttggtgcg gacatctcgg     2280
tagtgggata cgacgatacc gaagacagct catgttatat cccgccgtta accaccatca     2340
aacaggattt tcgcctgctg gggcaaacca gcgtggaccg cttgctgcaa ctctctcagg     2400
gccaggcggt gaagggcaat cagctgttgc ccgtctcact ggtgaaaaga aaaccaccc      2460 tggcgcccaa tacgcaaacc gcctctcccc gcgcgttggc cgattcatta atgcagctgg     2520
cacgacaggt ttcccgactg aaagcgggc agtgagcgca acgcaattaa tgtaagttag     2580
ctcactcatt aggcaccggg atctcgaccg atgcccttga gagccttcaa cccagtcagc     2640
tccttccggt gggcgcgggg catgactatc gtcgccgcac ttatgactgt cttctttatc     2700
atgcaactcg taggacaggt gccggcagcg ctctgggtca ttttcggcga ggaccgcttt     2760
cgctggagcg cgacgatgat cggcctgtcg cttgcggtat cggaatctt gcacgccctc      2820 gctcaagcct cgtcactgg tcccgccacc aaacgtttcg gcgagaagca ggccattatc      2880
gccggcatgg cggccccacg ggtgcgcatg atcgtgctcc tgtcgttgag gacccggcta     2940
ggctggcggg gttgccttac tggttagcag aatgaatcac cgatacgcga gcgaacgtga     3000
agcgactgct gctgcaaaac gtctgcgacc tgagcaacaa catgaatggt cttcggtttc     3060
cgtgtttcgt aaagtctgga aacgcggaag tcagcgccct gcaccattat gttccggatc     3120
```

```
tgcatcgcag gatgctgctg gctaccctgt ggaacaccta catctgtatt aacgaagcgc    3180
tggcattgac cctgagtgat ttttctctgg tcccgccgca tccataccgc cagttgttta    3240
ccctcacaac gttccagtaa ccgggcatgt tcatcatcag taacccgtat cgtgagcatc    3300
ctctctcgtt tcatcggtat cattacccce atgaacagaa atcccccta cacggaggca    3360 tcagtgacca aacaggaaaa aaccgcccctt aacatggccc gctttatcag aagccagaca    3420
ttaacgcttc tggagaaact caacgagctg gacgcggatg aacaggcaga catctgtgaa    3480
tcgcttcacg accacgctga tgagctttac cgcagctgcc tcgcgcgttt cggtgatgac    3540
ggtgaaaacc tctgacacat gcagctcccg gagacggtca cagcttgtct gtaagcggat    3600
gccgggagca gacaagcccg tcaggggcgcg tcagcgggtg ttggcgggtg tcggggcgca    3660
gccatgaccc agtcacgtag cgatagcgga gtgtatactg gcttaactat gcggcatcag    3720
agcagattgt actgagagtg caccatatat gcggtgtgaa ataccgcaca gatgcgtaag    3780
gagaaaatac cgcatcaggc gctcttccgc ttcctcgctc actgactcgc tgcgctcggt    3840
cgttcggctg cggcgagcgg tatcagctca ctcaaaggcg gtaatacggt tatccacaga    3900
atcaggggat aacgcaggaa agaacatgtg agcaaaaggc cagcaaaagg ccaggaaccg    3960
taaaaaggcc gcgttgctgg cgttttccca taggctccgc cccctgacg agcatcacaa    4020 aaatcgacgc tcaagtcaga ggtggcgaaa cccgacagga ctataaagat accaggcgtt    4080
tccccctgga agctccctcg tgcgctctcc tgttccgacc ctgccgctta ccggatacct    4140
gtccgccttt ctcccttcgg gaagcgtggc gctttctcat agctcacgct gtaggtatct    4200
cagttcggtg taggtcgttc gctccaagct gggctgtgtg cacgaacccc ccgttcagcc    4260
cgaccgctgc gccttatccg gtaactatcg tcttgagtcc aacccggtaa gacacgactt    4320
atcgccactg gcagcagcca ctggtaacag gattagcaga gcgaggtatg taggcggtgc    4380
tacagagttc ttgaagtggt ggcctaacta cggctacact agaaggacag tatttggtat    4440
ctgcgctctg ctgaagccag ttaccttcgg aaaaagagtt ggtagctctt gatccggcaa    4500
acaaaccacc gctggtagcg gtggtttttt tgtttgcaag cagcagatta cgcgcagaaa    4560
aaaaggatct caagaagatc ctttgatctt ttctacgggg tctgacgctc agtggaacga    4620
aaactcacgt taagggattt tggtcatgaa caataaaact gtctgcttac ataaacagta    4680
atacaagggg tgttatgagc catattcaac gggaaacgtc ttgctctagg ccgcgattaa    4740
attccaacat ggatgctgat ttatatgggt ataaatgggc tcgcgataat gtcgggcaat    4800
caggtgcgac aatctatcga ttgtatggga agcccgatgc gccagagttg tttctgaaac    4860
atggcaaagg tagcgttgcc aatgatgtta cagatgagat ggtcagacta aactggctga    4920
cggaatttat gcctcttccg accatcaagc attttatccg tactcctgat gatgcatggt    4980
tactcaccac tgcgatcccc gggaaaacag cattccaggt attagaagaa tatcctgatt    5040
caggtgaaaa tattgttgat gcgctggcag tgttcctgcg ccggttgcat tcgattcctg    5100
tttgtaattg tccttttaac agcgatcgcg tatttcgtct cgctcaggcg caatcacgaa    5160
tgaataacgg tttggttgat gcgagtgatt ttgatgacga gcgtaatggc tggcctgttg    5220
aacaagtctg gaaagaaatg cataaacttt tgccattctc accggattca gtcgtcactc    5280
atggtgattt ctcacttgat aaccttattt ttgacgaggg gaaattaata ggttgtattg    5340
atgttggacg agtcggaatc gcagaccgat accaggatct tgccatccta tggaactgcc    5400
tcggtgagtt ttctccttca ttacagaaac ggctttttca aaaatatggt attgataatc    5460
ctgatatgaa taaattgcag tttcatttga tgctcgatga gtttttctaa gaattaattc    5520
```

```
atgagcggat acatatttga atgtatttag aaaaataaac aaatagggt tccgcgcaca    5580 tttccccgaa aagtgccacc tgaaattgta acgttaata ttttgttaaa attcgcgtta    5640 aattttttgtt aaatcagctc attttttaac caataggccg aaatcggcaa aatcccttat  5700
aaatcaaaag aatagaccga gatagggttg agtgttgttc cagtttggaa caagagtcca   5760
ctattaaaga acgtggactc caacgtcaaa gggcgaaaaa ccgtctatca gggcgatggc   5820
ccactacgtg aaccatcacc ctaatcaagt tttttggggt cgaggtgccg taaagcacta   5880
aatcggaacc ctaaagggag cccccgattt agagcttgac ggggaaagcc ggcgaacgtg   5940
gcgagaaagg aagggaagaa agcgaaagga gcgggcgcta gggcgctggc aagtgtagcg   6000
gtcacgctgc gcgtaaccac cacacccgcc gcgcttaatg cgccgctaca gggcgcgtcc   6060
cattcgcca                                                           6069

<210> SEQ ID NO 93
<211> LENGTH: 43
<212> TYPE: DNA
<213> ORGANISM: Artificial Sequence
<220> FEATURE:
<223> OTHER INFORMATION: Synthetic: primer

<400> SEQUENCE: 93
ccgtgaacaa atcggcggcc aagccccgtt tttcaaagaa atc                     43

<210> SEQ ID NO 94
<211> LENGTH: 6069
<212> TYPE: DNA
<213> ORGANISM: Artificial Sequence
<220> FEATURE:
<223> OTHER INFORMATION: Synthetic: plasmid

<400> SEQUENCE: 94
atccggatat agttcctcct ttcagcaaaa aaccccctcaa gacccgttta gaggccccaa   60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttgt   180
cgacttatta gtgatggtga tggtgatgtt tgctggcacg ctgaccctgg aacatcgttt   240
gactacgttt acgttacgc agattggagc gcggcgacag atcgttcata actttgatca    300
gttctgagat ggctttacgt tggatctgca ggttgtccac cgggattttg atcagttttt   360
cgaaatcgtt cagtttacca gagctgccgt tcaggaagcg ctgaaacatg tcctgtttaa   420
taacatccat actacgttgg atcgcctgat tgtctttgaa gatttcgaaa aatttgaagt   480
agaaggagac gatttgactc tggataattt tcttatcgct ttcttctttc cagttttttca  540 ggatttccag gaacagcgga ccaccattcg ggacatcgga ggttgacgca ttgaagtagt    600
ctttcaggat cgtgatttct ttgaaaaacg gggcttggcc gccgatttgt tcacggtgtg    660
cttcgataat gtcgttgtct tccatgtcca ggtcttccgg ggtttgatcc gcctggatgc    720
gaataccgtc atacaggaaa cgcagactat ccatttcctt gccctgacgt ttggcaaacg    780
cttccatcag gcgacgcagc ggcgtggtct ttttgatctt aaagaaaatt tcagagctgc    840
cgtcactaac tttcaggttg atgtgggttt ccggtttcac ttccgtttc acttccggtt   900 tcgcttcttg gttcacttcg ctatcgctca tggtacccag atctgggctg tccatgtgct   960
ggcgttcgaa tttagcagca gcggtttctt tcatatgtat atctccttct taaagttaaa   1020
caaaattatt tctagagggg aattgttatc cgctcacaat tcccctatag tgagtcgtat   1080
```

```
taatttcgcg ggatcgagat cgatctcgat cctctacgcc ggacgcatcg tggccggcat    1140
caccggcgcc acaggtgcgg ttgctggcgc ctatatcgcc gacatcaccg atggggaaga    1200
tcgggctcgc cacttcgggc tcatgagcgc ttgtttcggc gtgggtatgg tggcaggccc    1260
cgtggccggg ggactgttgg gcgccatctc cttgcatgca ccattccttg cggcggcggt    1320
gctcaacggc ctcaacctac tactgggctg cttcctaatg caggagtcgc ataagggaga    1380
gcgtcgagat cccggacacc atcgaatggc gcaaaacctt tcgcggtatg gcatgatagc    1440
gcccggaaga gagtcaattc agggtggtga atgtgaaacc agtaacgtta tacgatgtcg    1500
cagagtatgc cggtgtctct tatcagaccg tttcccgcgt ggtgaaccag gccagccacg    1560
tttctgcgaa aacgcgggaa aaagtggaag cggcgatggc ggagctgaat tacattccca    1620
accgcgtggc acaacaactg gcgggcaaac agtcgttgct gattggcgtt gccacctcca    1680
gtctggccct gcacgcgccg tcgcaaattg tcgcggcgat taaatctcgc gccgatcaac    1740
tgggtgccag cgtggtggtg tcgatggtag aacgaagcgg cgtcgaagcc tgtaaagcgg    1800
cggtgcacaa tcttctcgcg caacgcgtca gtgggctgat cattaactat ccgctggatg    1860
accaggatgc cattgctgtg gaagctgcct gcactaatgt tccggcgtta tttcttgatg    1920
tctctgacca gacacccatc aacagtatta ttttctccca tgaagacggt acgcgactgg    1980
gcgtggagca tctggtcgca ttgggtcacc agcaaatcgc gctgttagcg ggcccattaa    2040
gttctgtctc ggcgcgtctg cgtctggctg gctggcataa atatctcact cgcaatcaaa    2100
ttcagccgat agcggaacgg gaaggcgact ggagtgccat gtccggtttt caacaaacca    2160
tgcaaatgct gaatgagggc atcgttccca ctgcgatgct ggttgccaac gatcagatgg    2220
cgctgggcgc aatgcgcgcc attaccgagt ccgggctgcg cgttggtgcg gacatctcgg    2280
tagtgggata cgacgatacc gaagacagct catgttatat cccgccgtta accaccatca    2340
aacaggattt tcgcctgctg gggcaaacca gcgtggaccg cttgctgcaa ctctctcagg    2400
gccaggcggt gaagggcaat cagctgttgc ccgtctcact ggtgaaaaga aaaaccaccc    2460
tggcgcccaa tacgcaaacc gcctctcccc gcgcgttggc cgattcatta atgcagctgg    2520
cacgacaggt ttcccgactg gaaagcgggc agtgagcgca acgcaattaa tgtaagttag    2580
ctcactcatt aggcaccggg atctcgaccg atgcccttga gagccttcaa cccagtcagc    2640
tccttccggt gggcgcgggg catgactatc gtcgccgcac ttatgactgt cttctttatc    2700
atgcaactcg taggacaggt gccggcagcg ctctgggtca ttttcggcga ggaccgcttt    2760
cgctggagcg cgacgatgat cggcctgtcg cttgcggtat tcggaatctt gcacgccctc    2820
gctcaagcct tcgtcactgg tcccgccacc aaacgtttcg gcgagaagca ggccattatc    2880
gccggcatgg cggccccacg ggtgcgcatg atcgtgctcc tgtcgttgag gacccggcta    2940
ggctggcggg gttgccttac tggttagcag aatgaatcac cgatacgcga gcgaacgtga    3000
agcgactgct gctgcaaaac gtctgcgacc tgagcaacaa catgaatggt cttcggtttc    3060
cgtgtttcgt aaagtctgga aacgcggaag tcagcgccct gcaccattat gttccggatc    3120
tgcatcgcag gatgctgctg gctaccctgt ggaacaccta catctgtatt aacgaagcgc    3180
tggcattgac cctgagtgat ttttctctgg tcccgccgca tccataccgc cagttgttta    3240
ccctcacaac gttccagtaa ccgggcatgt tcatcatcag taacccgtat cgtgagcatc    3300
ctctctcgtt tcatcggtat cattacccce atgaacagaa atccccctta cacggaggca    3360
tcagtgacca aacaggaaaa aaccgccctt aacatggccc gctttatcag aagccagaca    3420
ttaacgcttc tggagaaact caacgagctg gacgcggatg aacaggcaga catctgtgaa    3480
```

```
tcgcttcacg accacgctga tgagctttac cgcagctgcc tcgcgcgttt cggtgatgac   3540
ggtgaaaacc tctgacacat gcagctcccg gagacggtca cagcttgtct gtaagcggat   3600
gccgggagca gacaagcccg tcagggcgcg tcagcgggtg ttggcgggtg tcggggcgca   3660
gccatgaccc agtcacgtag cgatagcgga gtgtatactg gcttaactat gcggcatcag   3720
agcagattgt actgagagtg caccatatat gcggtgtgaa ataccgcaca gatgcgtaag   3780
gagaaaatac cgcatcaggc gctcttccgc ttcctcgctc actgactcgc tgcgctcggt   3840
cgttcggctg cggcgagcgg tatcagctca ctcaaaggcg gtaatacggt tatccacaga   3900
atcaggggat aacgcaggaa agaacatgtg agcaaaaggc cagcaaaagg ccaggaaccg   3960
taaaaaggcc gcgttgctgg cgttttccca taggctccgc cccctgacg agcatcacaa    4020
aaatcgacgc tcaagtcaga ggtggcgaaa cccgacagga ctataaagat accaggcgtt   4080
tcccctgga agctccctcg tgcgctctcc tgttccgacc ctgccgctta ccggatacct    4140
gtccgcttt ctcccttcgg gaagcgtggc gctttctcat agctcacgct gtaggtatct    4200
cagttcggtg taggtcgttc gctccaagct gggctgtgtg cacgaacccc ccgttcagcc   4260
cgaccgctgc gccttatccg gtaactatcg tcttgagtcc aacccggtaa gacacgactt   4320
atcgccactg gcagcagcca ctggtaacag gattagcaga gcgaggtatg taggcggtgc   4380
tacagagttc ttgaagtggt ggcctaacta cggctacact agaaggacag tatttggtat   4440
ctgcgctctg ctgaagccag ttaccttcgg aaaaagagtt ggtagctctt gatccggcaa   4500
acaaaccacc gctggtagcg gtggtttttt tgtttgcaag cagcagatta cgcgcagaaa   4560
aaaaggatct caagaagatc ctttgatctt ttctacgggg tctgacgctc agtggaacga   4620
aaactcacgt taagggattt tggtcatgaa caataaaact gtctgcttac ataaacagta   4680
atacaagggg tgttatgagc catattcaac gggaaacgtc ttgctctagg ccgcgattaa   4740
attccaacat ggatgctgat ttatatgggt ataaatgggc tcgcgataat gtcgggcaat   4800
caggtgcgac aatctatcga ttgtatggga agcccgatgc gccagagttg tttctgaaac   4860
atggcaaagg tagcgttgcc aatgatgtta cagatgagat ggtcagacta aactggctga   4920
cggaatttat gcctcttccg accatcaagc atttatccg tactcctgat gatgcatggt    4980
tactcaccac tgcgatcccc gggaaaacag cattccaggt attagaagaa tatcctgatt   5040
caggtgaaaa tattgttgat gcgctggcag tgttcctgcg ccggttgcat tcgattcctg   5100
tttgtaattg tccttttaac agcgatcgcg tatttcgtct cgctcaggcg caatcacgaa   5160
tgaataacgg tttggttgat gcgagtgatt ttgatgacga gcgtaatggc tggcctgttg   5220
aacaagtctg gaaagaaatg cataaacttt tgccattctc accggattca gtcgtcactc   5280
atggtgattt ctcacttgat aaccttattt ttgacgaggg gaaattaata ggttgtattg   5340
atgttggacg agtcggaatc gcagaccgat accaggatct tgccatccta tggaactgcc   5400
tcggtgagtt ttctccttca ttacagaaac ggcttttca aaaatatggt attgataatc    5460
ctgatatgaa taaattgcag tttcatttga tgctcgatga ttttttctaa gaattaattc   5520
atgagcggat acatatttga atgtatttag aaaaataaac aaataggggt tccgcgcaca   5580
tttccccgaa aagtgccacc tgaaattgta acgttaata ttttgttaaa attcgcgtta    5640
aattttttgtt aaatcagctc attttttaac caataggccg aaatcggcaa aatcccttat   5700
aaatcaaaag aatagaccga gatagggttg agtgttgttc cagtttggaa caagagtcca   5760
ctattaaaga acgtggactc caacgtcaaa gggcgaaaaa ccgtctatca gggcgatggc   5820
```

```
ccactacgtg aaccatcacc ctaatcaagt tttttggggt cgaggtgccg taaagcacta    5880
aatcggaacc ctaaagggag cccccgattt agagcttgac ggggaaagcc ggcgaacgtg    5940
gcgagaaagg aagggaagaa agcgaaagga gcgggcgcta gggcgctggc aagtgtagcg    6000
gtcacgctgc gcgtaaccac cacacccgcc gcgcttaatg cgccgctaca gggcgcgtcc    6060
cattcgcca                                                            6069

<210> SEQ ID NO 95
<211> LENGTH: 4439
<212> TYPE: DNA
<213> ORGANISM: Artificial Sequence
<220> FEATURE:
<223> OTHER INFORMATION: Synthetic: plasmid

<400> SEQUENCE: 95
ggtaccaaag catgcaatga gctcagtaac ccgtatcgtg agcatcctct ctcgtttcat      60
cggtatcatt accccatga acagaaatcc cccttacacg gaggcatcag tgaccaaaca     120
ggaaaaaacc gcccttaaca tggcccgctt tatcagaagc cagacattaa cgcttctgga     180
gaaactcaac gagctggacg cggatgaaca ggcagacatc tgtgaatcgc ttcacgacca     240
cgctgatgag ctttaccgca gctgcctcgc gcgtttcggt gatgacggtg aaaacctctg     300
acacatgcag ctcccggaga cggtcacagc ttgtctgtaa gcggatgccg ggagcagaca     360
agcccgtcag ggcgcgtcag cgggtgttgg cgggtgtcgg ggcgcagcca tgacccagtc     420
acgtagcgat agcggagtgt atactggctt aactatgcgg catcagagca gattgtactg     480
agagtgcacc attgcggtgt gaaataccgc acagatgcgt aaggagaaaa taccgcatca     540
ggcgctcttc cgcttcctcg ctcactgact cgctgcgctc ggtcgttcgg ctgcggcgag     600
cggtatcagc tcactcaaag gcggtaatac ggttatccac agaatcaggg gataacgcag     660
gaaagaacat gtgagcaaaa ggccagcaaa aggccaggaa ccgtaaaaag gccgcgttgc     720
tggcgttttt ccataggctc cgcccccctg acgagcatca caaaaatcga cgctcaagtc     780
agaggtggcg aaacccgaca ggactataaa gataccaggc gtttccccct ggaagctccc     840
tcgtgcgctc tcctgttccg accctgccgc ttaccggata cctgtccgcc tttctccctt     900
cgggaagcgt ggcgctttct catagctcac gctgtaggta tctcagttcg gtgtaggtcg     960
ttcgctccaa gctgggctgt gtgcacgaac cccccgttca gcccgaccgc tgcgccttat    1020
ccggtaacta tcgtcttgag tccaacccgg taagacacga cttatcgcca ctggcagcag    1080
ccactggtaa caggattagc agagcgaggt atgtaggcgg tgctacagag ttcttgaagt    1140
ggtggcctaa ctacggctac actagaagga cagtatttgg tatctgcgct ctgctgaagc    1200
cagttacctt cggaaaaaga gttggtagct cttgatccgg caaacaaacc accgctggta    1260
gcggtggttt ttttgtttgc aagcagcaga ttacgcgcag aaaaaaagga tctcaagaag    1320
atcctttgat cttttctacg ggtctgacgc tcagtggaa cgaaaactca cgttaaggga    1380
ttttggtcat gaacaataaa actgtctgct tacataaaca gtaatacaag gggtgttatg    1440
agccatatca acgggaaacg ctcgagtacg tatctagagc aaagcttatc gtcgacttat    1500
tagtgatggt gatggtgatg tttgctggca cgctgaccct ggaacatcgt ttgactacgt    1560
ttacgtttac gcagattgga gcgcggcgac agatcgttca aactttgat cagttctgag    1620 atggctttac gttggatctg caggttgtcc accgggattt tgatcagttt ttcgaaatcg    1680
ttcagtttac cagagctgcc gttcaggaag cgctgaaaca tgtcctgttt aataacatcc    1740
atactacgtt ggatcgcctg attgtctttg aagatttcga aaaatttgaa gtagaaggag    1800
```

```
acgatttgac tctggataat tttcttatcg ctttcttctt tccagttttt caggatttcc    1860
aggaacagcg gaccaccatt cgggacatcg gaggttgacg cattgaagta gtctttcagg    1920
atcgtgattt cttttgaaaaa cggggcttgg ccgccgattt gttcacggtg tgcttcgata   1980
atgtcgttgt cttccatgtc caggtcttcc ggggtttgat ccgcctggat gcgaataccg    2040
tcatacagga aacgcagact atccatttcc ttgccctgac gtttggcaaa cgcttccatc    2100
aggcgacgca gcggcgtggt cttttgatc ttaaagaaaa tttcagagct gccgtcacta     2160
actttcaggt tgatgtgggt ttccggtttc acttccggtt tcacttccgg tttcgcttct    2220
tggttcactt cgctatcgct catggtaccc agatctgggc tgtccatgtg ctggcgttcg    2280
aatttagcag cagcggtttc tttcatatgt attcctcctt cttaaagtta aacaaaaaaa    2340
cgggtatgga gaaacagtag caagttgcga taaaaagcgt caggtaggat ccgctaatct    2400
tatggataaa aatgctatgg catagcaaag tgtgacgccg tgcaaataat caatgtggac    2460
ttttctgccg tgattataga cactttgtt acgcgttttt gtcatggctt tggtcccgct     2520
ttgttacaga atgcttttaa taagcggggt taccggtttg gttagcgaga agagccagta    2580
aaagacgcag tgacggcaat gtctgatgca atatggacaa ttggtttctt ctctgaatgg    2640
cgggagtatg aaaagtatgg ctgaagcgca aaatgatccc ctgctgccgg atactcgtt    2700 taatgcccat ctggtggcgg gtttaacgcc gattgaggcc aacggttatc tcgatttttt    2760
tatcgaccga ccgctgggaa tgaaaggtta tattctcaat ctcaccattc gcggtcaggg    2820
ggtggtgaaa aatcagggac gagaatttgt ttgccgaccg ggtgatattt tgctgttccc    2880
gccaggagag attcatcact acggtcgtca tccggaggct cgcgaatggt atcaccagtg    2940
ggtttacttt cgtccgcgcg cctactggca tgaatggctt aactggccgt caatatttgc    3000
caatacgggg ttctttcgcc cggatgaagc gcaccagccg catttcagcg acctgtttgg    3060
gcaaatcatt aacgccgggc aaggggaagg gcgctattcg gagctgctgg cgataaatct    3120
gcttgagcaa ttgttactgc ggcgcatgga agcgattaac gagtcgctcc atccaccgat    3180
ggataatcgg gtacgcgagg cttgtcagta catcagcgat cacctggcag acagcaattt    3240
tgatatcgcc agcgtcgcac agcatgtttg cttgtcgccg tcgcgtctgt cacatctttt    3300
ccgccagcag ttagggatta gcgtcttaag ctggcgcgag gaccaacgta tcagccaggc    3360
gaagctgctt ttgagcacca cccggatgcc tatcgccacc gtcggtcgca atgttggttt    3420
tgacgatcaa ctctatttct cgcgggtatt taaaaaatgc accggggcca gcccgagcga    3480
gttccgtgcc ggttgtgaag aaaaagtgaa tgatgtagcc gtcaagttgt cataattggt    3540
aacgaatcag acaattgacg gcttgacgga gtagcatagg gtttgcagaa tccctgcttc    3600
gtccatttga caggcacatt atgcgaattc gctagcagat cttagtgaca ttagaaaacc    3660
gactgtaaaa agtacagtcg gcattatctc atattataaa agccagtcat taggcctatc    3720
tgacaattcc tgaatagagt tcataaacaa tcctgcatga taaccatcac aaacagaatg    3780
atgtacctgt aaagatagcg gtaaatatat tgaattacct ttattaatga attttcctgc    3840
tgtaataatg ggtagaaggt aattactatt attattgata tttaagttaa acccagtaaa    3900
tgaagtccat ggaataatag aaagagaaaa agcattttca ggtataggtg ttttgggaaa    3960
caatttcccc gaaccattat atttctctac atcagaaagg tataaatcat aaaactcttt    4020
gaagtcattc tttacaggag tccaaatacc agagaatgtt ttagatacac catcaaaaat    4080
tgtataaagt ggctctaact tatcccaata acctaactct ccgtcgctat tgtaaccagt    4140
```

```
tctaaaagct gtatttgagt ttatcaccct tgtcactaag aaaataaatg cagggtaaaa    4200
tttatatcct tcttgtttta tgtttcggta taaaacacta atatcaattt ctgtggttat    4260
actaaaagtc gtttgttggt tcaaataatg attaaatatc tcttttctct tccaattgtc    4320
taaatcaatt ttattaaagt tcatttgata tgcctcctaa atttttatct aaagtgaatt    4380
taggaggctt acttgtctgc tttcttcatt agaatcaatc cttttttaaa agtcaatcc     4439

<210> SEQ ID NO 96
<211> LENGTH: 42
<212> TYPE: DNA
<213> ORGANISM: Artificial Sequence
<220> FEATURE:
<223> OTHER INFORMATION: Synthetic: primer

<400> SEQUENCE: 96
gatatactcg agttatttta aagcgtcggt taaaatcaaa tg                        42

<210> SEQ ID NO 97
<211> LENGTH: 6318
<212> TYPE: DNA
<213> ORGANISM: Artificial Sequence
<220> FEATURE:
<223> OTHER INFORMATION: Synthetic: plasmid

<400> SEQUENCE: 97
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgagttattt taaagcgtcg gttaaaatca atgggcaat aaatcttctc atcctaatcg      240
catctttata atcaaaatcc aatggcgcat ctgcacttcc atagagagta ttcatacaaa     300
catatattcc gcagtcgtag ccatttggtt gctgcggaca atctaaatga atcaaatcaa     360
agtcttctcc tattgtatgc ttactttcct ccataacata ttttttgcaag tcagtcagta     420 tagcgaaact catagcattt ggaccattcg ataatgaatc tacgtaacct atagttttct     480
tttttaaatc aattatgccc aacgccagt ggggattggt caaatttatt ggtgtaaaga     540
ttttatcaag tttatcaatt tgtgtcttct ttctcttcat ccacctccgg acgccttgat     600 aaccccttc tgataaattg gtatagaaaa acgaattaaa cgccactgta ttaggggtag     660 attttttcaat gtatttcata aaaaactcaa tgatagtgtc atttagccat cttcgtggtg     720
ccaaggtctt aaaatcacgt actgttatct ctatattatc tctattcatt aactgagtat     780
tttctctaga tgccaaagct ttttgtactt ggtcatcgtc ttttttcattt aattcaggaa     840 caagggatcc aacgatgctg attgccgttc cggcaaacgc ggtccgtttt ttcgtctcgt     900
cgctggcagc ctccggccag agcacatcct cataacggaa cgtgccggac ttgtagaacg     960
tcagcgtggt gctggtctgg tcagcagcaa ccgcaagaat gccaacggca gcaccgtcgg    1020
tggtgccatc ccacgcaacc agcttacggc tggaggtgtc cagcatcagc ggggtcattg    1080
caggcgcttt cgcactcaat ccgccgggcg cggttgcggt atgagccggg tcactgttgc    1140
cctgcggctg gtaatgggta aaggttttctt tgctcgtcat ggtacccaga tctgggctgt    1200
ccatgtgctg gcgttcgaat ttagcagcag cggtttctttt catatgtata tctccttctt    1260
aaagttaaac aaaattattt ctagagggga attgttatcc gctcacaatt ccctatagt    1320 gagtcgtatt aatttcgcgg gatcgagatc gatctcgatc ctctacgccg gacgcatcgt    1380
ggccggcatc accggcgcca caggtgcggt tgctggcgcc tatatcgccg acatcaccga    1440
```

```
tggggaagat cgggctcgcc acttcgggct catgagcgct tgtttcggcg tgggtatggt   1500
ggcaggcccc gtggccgggg gactgttggg cgccatctcc ttgcatgcac cattccttgc   1560
ggcggcggtg ctcaacggcc tcaacctact actgggctgc ttcctaatgc aggagtcgca   1620
taagggagag cgtcgagatc ccggacacca tcgaatggcg caaaaccttt cgcggtatgg   1680
catgatagcg cccggaagag agtcaattca gggtggtgaa tgtgaaacca gtaacgttat   1740
acgatgtcgc agagtatgcc ggtgtctctt atcagaccgt ttcccgcgtg gtgaaccagg   1800
ccagccacgt ttctgcgaaa acgcgggaaa aagtggaagc ggcgatggcg gagctgaatt   1860
acattcccaa ccgcgtggca caacaactgg cgggcaaaca gtcgttgctg attggcgttg   1920
ccacctccag tctggccctg cacgcgccgt cgcaaattgt cgcggcgatt aaatctcgcg   1980
ccgatcaact gggtgccagc gtggtggtgt cgatggtaga acgaagcggc gtcgaagcct   2040
gtaaagcggc ggtgcacaat cttctcgcgc aacgcgtcag tgggctgatc attaactatc   2100
cgctggatga ccaggatgcc attgctgtgg aagctgcctg cactaatgtt ccggcgttat   2160
ttcttgatgt ctctgaccag acacccatca acagtattat tttctcccat gaagacggta   2220
cgcgactggg cgtggagcat ctggtcgcat tgggtcacca gcaaatcgcg ctgttagcgg   2280
gcccattaag ttctgtctcg gcgcgtctgc gtctggctgg ctggcataaa tatctcactc   2340
gcaatcaaat tcagccgata gcggaacggg aaggcgactg gagtgccatg tccggttttc   2400
aacaaaccat gcaaatgctg aatgagggca tcgttcccac tgcgatgctg gttgccaacg   2460
atcagatggc gctgggcgca atgcgcgcca ttaccgagtc cgggctgcgc gttggtgcgg   2520
acatctcggt agtgggatac gacgataccg aagacagctc atgttatatc cgccgttaa   2580 ccaccatcaa acaggatttt cgcctgctgg ggcaaaccag cgtggaccgc ttgctgcaac   2640
tctctcaggg ccaggcggtg aagggcaatc agctgttgcc cgtctcactg gtgaaaagaa   2700
aaaccaccct ggcgcccaat acgcaaaccg cctctccccg cgcgttggcc gattcattaa   2760
tgcagctggc acgacaggtt tcccgactgg aaagcgggca gtgagcgcaa cgcaattaat   2820
gtaagttagc tcactcatta ggcaccggga tctcgaccga tgcccttgag agccttcaac   2880
ccagtcagct ccttccggtg ggcgcggggc atgactatcg tcgccgcact tatgactgtc   2940
ttctttatca tgcaactcgt aggacaggtg ccggcagcgc tctgggtcat tttcggcgag   3000
gaccgctttc gctggagcgc gacgatgatc ggcctgtcgc ttgcggtatt cggaatcttg   3060
cacgccctcg ctcaagcctt cgtcactggt cccgccacca aacgtttcgg cgagaagcag   3120
gccattatcg ccggcatggc ggccccacgg gtgcgcatga tcgtgctcct gtcgttgagg   3180
acccggctag gctggcgggg ttgccttact ggttagcaga atgaatcacc gatacgcgag   3240
cgaacgtgaa gcgactgctg ctgcaaaacg tctgcgacct gagcaacaac atgaatggtc   3300
ttcggtttcc gtgtttcgta aagtctggaa acgcggaagt cagcgccctg caccattatg   3360
ttccggatct gcatcgcagg atgctgctgg ctaccctgtg aacacctac atctgtatta   3420 acgaagcgct ggcattgacc ctgagtgatt tttctctggt cccgccgcat ccataccgcc   3480
agttgtttac cctcacaacg ttccagtaac cgggcatgtt catcatcagt aacccgtatc   3540
gtgagcatcc tctctcgttt catcggtatc attaccccca tgaacagaaa tcccccttac   3600
acggaggcat cagtgaccaa acaggaaaaa accgccctta acatgcccg ctttatcaga   3660 agccagacat taacgcttct ggagaaactc aacgagctgg acgcggatga acaggcagac   3720
atctgtgaat cgcttcacga ccacgctgat gagctttacc gcagctgcct cgcgcgtttc   3780
```

```
ggtgatgacg gtgaaaacct ctgacacatg cagctcccgg agacggtcac agcttgtctg    3840
taagcggatg ccgggagcag acaagcccgt cagggcgcgt cagcgggtgt tggcgggtgt    3900
cggggcgcag ccatgaccca gtcacgtagc gatagcggag tgtatactgg cttaactatg    3960
cggcatcaga gcagattgta ctgagagtgc accatatatg cggtgtgaaa taccgcacag    4020
atgcgtaagg agaaaatacc gcatcaggcg ctcttccgct tcctcgctca ctgactcgct    4080
gcgctcggtc gttcggctgc ggcgagcggt atcagctcac tcaaaggcgg taatacggtt    4140
atccacagaa tcaggggata acgcaggaaa gaacatgtga gcaaaaggcc agcaaaaggc    4200
caggaaccgt aaaaaggccg cgttgctggc gtttttccat aggctccgcc ccctgacga    4260 gcatcacaaa aatcgacgct caagtcagag gtggcgaaac ccgacaggac tataaagata    4320
ccaggcgttt cccctggaa gctccctcgt gcgctctcct gttccgaccc tgccgcttac    4380 cggataccctg tccgccttc tcccttcggg aagcgtggcg ctttctcata gctcacgctg    4440
taggtatctc agttcggtgt aggtcgttcg ctccaagctg ggctgtgtgc acgaaccccc    4500
cgttcagccc gaccgctgcg ccttatccgg taactatcgt cttgagtcca acccggtaag    4560
acacgactta tcgccactgg cagcagccac tggtaacagg attagcagag cgaggtatgt    4620
aggcggtgct acagagttct tgaagtggtg gcctaactac ggctacacta aggacagt     4680 atttggtatc tgcgctctgc tgaagccagt taccttcgga aaaagagttg gtagctcttg    4740
atccggcaaa caaccaccg ctggtagcgg tggtttttt gtttgcaagc agcagattac     4800
gcgcagaaaa aaaggatctc aagaagatcc tttgatcttt tctacggggt ctgacgctca    4860
gtggaacgaa aactcacgtt aagggatttt ggtcatgaac aataaaactg tctgcttaca    4920
taaacagtaa tacaagggt gttatgagcc atattcaacg ggaaacgtct gctctaggc     4980 cgcgattaaa ttccaacatg gatgctgatt tatatgggta taaatgggct cgcgataatg    5040
tcgggcaatc aggtgcgaca atctatcgat tgtatgggaa gcccgatgcg ccagagttgt    5100
ttctgaaaca tggcaaaggt agcgttgcca atgatgttac agatgagatg gtcagactaa    5160
actggctgac ggaatttatg cctcttccga ccatcaagca ttttatccgt actcctgatg    5220
atgcatggtt actcaccact gcgatccccg ggaaaacagc attccaggta ttagaagaat    5280
atcctgattc aggtgaaaat attgttgatg cgctggcagt gttcctgcgc cggttgcatt    5340
cgattcctgt ttgtaattgt cctttaaca gcgatcgcgt atttcgtctc gctcaggcgc    5400
aatcacgaat gaataacggt ttggttgatg cgagtgattt tgatgacgag cgtaatggct    5460
ggcctgttga acaagtctgg aaagaaatgc ataaactttt gccattctca ccggattcag    5520
tcgtcactca tggtgatttc tcacttgata accttatttt tgacgagggg aaattaatag    5580
gttgtattga tgttggacga gtcggaatcg cagaccgata ccaggatctt gccatcctat    5640
ggaactgcct cggtgagttt tctccttcat tacagaaacg gctttttcaa aaatatggta    5700
ttgataatcc tgatatgaat aaattgcagt ttcatttgat gctcgatgag ttttctaag    5760 aattaattca tgagcggata catatttgaa tgtatttaga aaaataaaca aataggggtt    5820
ccgcgcacat ttccccgaaa agtgccacct gaaattgtaa acgttaatat tttgttaaaa    5880
ttcgcgttaa attttttgtta aatcagctca ttttttaacc aataggccga atcggcaaa    5940 atcccttata aatcaaaaga atagaccgag atagggttga gtgttgttcc agtttggaac    6000
aagagtccac tattaaagaa cgtggactcc aacgtcaaag ggcgaaaaac cgtctatcag    6060
ggcgatggcc cactacgtga accatcaccc taatcaagtt ttttggggtc gaggtgccgt    6120
aaagcactaa atcggaaccc taaagggagc ccccgattta gagcttgacg gggaaagccg    6180
```

-continued

| | |
|---|---|
| gcgaacgtgg cgagaaagga agggaagaaa gcgaaaggag cgggcgctag ggcgctggca | 6240 |
| agtgtagcgg tcacgctgcg cgtaaccacc acacccgccg cgcttaatgc gccgctacag | 6300 |
| ggcgcgtccc attcgcca | 6318 |

<210> SEQ ID NO 98
<211> LENGTH: 3662
<212> TYPE: DNA
<213> ORGANISM: Artificial Sequence
<220> FEATURE:
<223> OTHER INFORMATION: Synthetic: plasmid

<400> SEQUENCE: 98

| | |
|---|---|
| ggtaccaaag catgcaatga gctcagtaac ccgtatcgtg agcatcctct ctcgtttcat | 60 |
| cggtatcatt accccatga acagaaatcc cccttacacg gaggcatcag tgaccaaaca | 120 |
| ggaaaaaacc gcccttaaca tggcccgctt tatcagaagc cagacattaa cgcttctgga | 180 |
| gaaactcaac gagctggacg cggatgaaca ggcagacatc tgtgaatcgc ttcacgacca | 240 |
| cgctgatgag ctttaccgca gctgcctcgc gcgtttcggt gatgacggtg aaaacctctg | 300 |
| acacatgcag ctcccggaga cggtcacagc ttgtctgtaa gcggatgccg ggagcagaca | 360 |
| agcccgtcag ggcgcgtcag cgggtgttgg cgggtgtcgg ggcgcagcca tgacccagtc | 420 |
| acgtagcgat agcggagtgt atactggctt aactatgcgg catcagagca gattgtactg | 480 |
| agagtgcacc attgcggtgt gaaataccgc acagatgcgt aaggagaaaa taccgcatca | 540 |
| ggcgctcttc cgcttcctcg ctcactgact cgctgcgctc ggtcgttcgg ctgcggcgag | 600 |
| cggtatcagc tcactcaaag gcggtaatac ggttatccac agaatcaggg gataacgcag | 660 |
| gaaagaacat gtgagcaaaa ggccagcaaa aggccaggaa ccgtaaaaag gccgcgttgc | 720 |
| tggcgttttt ccataggctc cgcccccctg acgagcatca caaaaatcga cgctcaagtc | 780 |
| agaggtggcg aaacccgaca ggactataaa gataccaggc gtttccccct ggaagctccc | 840 |
| tcgtgcgctc tcctgttccg accctgccgc ttaccggata cctgtccgcc tttctccctt | 900 |
| cgggaagcgt ggcgctttct catagctcac gctgtaggta tctcagttcg gtgtaggtcg | 960 |
| ttcgctccaa gctgggctgt gtgcacgaac cccccgttca gcccgaccgc tgcgccttat | 1020 |
| ccggtaacta tcgtcttgag tccaacccgg taagacacga cttatcgcca ctggcagcag | 1080 |
| ccactggtaa caggattagc agagcgaggt atgtaggcgg tgctacagag ttcttgaagt | 1140 |
| ggtggcctaa ctacggctac actagaagga cagtatttgg tatctgcgct ctgctgaagc | 1200 |
| cagttacctt cggaaaaaga gttggtagct cttgatccgg caaacaaacc accgctggta | 1260 |
| gcggtggttt ttttgtttgc aagcagcaga ttacgcgcag aaaaaaagga tctcaagaag | 1320 |
| atcctttgat cttttctacg gggtctgacg ctcagtggaa cgaaaactca cgttaaggga | 1380 |
| ttttggtcat gaacaataaa actgtctgct tacataaaca gtaatacaag gggtgttatg | 1440 |
| agccatatca cgggaaacg ctcgagtacg tatctagagc aaagcttatc gtcgacatgc | 1500 |
| atctgcagcc cggggatcc tcgcgacata tgtattcctc cttcttaaag ttaaacaaaa | 1560 |
| aaacgggtat ggagaaacag tagcaagttg cgataaaaag cgtcaggtag gatccgctaa | 1620 |
| tcttatggat aaaaatgcta tggcatagca aagtgtgacg ccgtgcaaat aatcaatgtg | 1680 |
| gactttctg ccgtgattat agacactttt gttacgcgtt tttgtcatgg ctttggtccc | 1740 |
| gctttgttac agaatgcttt taataagcgg ggttaccggt tggttagcg agaagagcca | 1800 |
| gtaaaagacg cagtgacggc aatgtctgat gcaatatgga caattggttt cttctctgaa | 1860 |

| | |
|---|---|
| tggcgggagt atgaaaagta tggctgaagc gcaaaatgat cccctgctgc cgggatactc | 1920 |
| gtttaatgcc catctggtgg cgggtttaac gccgattgag gccaacggtt atctcgattt | 1980 |
| ttttatcgac cgaccgctgg gaatgaaagg ttatattctc aatctcacca ttcgcggtca | 2040 |
| gggggtggtg aaaaatcagg gacgagaatt tgtttgccga ccgggtgata ttttgctgtt | 2100 |
| cccgccagga gagattcatc actacggtcg tcatccggag gctcgcgaat ggtatcacca | 2160 |
| gtgggtttac tttcgtccgc gcgcctactg gcatgaatgg cttaactggc cgtcaatatt | 2220 |
| tgccaatacg gggttctttc gcccggatga agcgcaccag ccgcatttca gcgacctgtt | 2280 |
| tgggcaaatc attaacgccg ggcaagggga agggcgctat tcggagctgc tggcgataaa | 2340 |
| tctgcttgag caattgttac tgcggcgcat ggaagcgatt aacgagtcgc tccatccacc | 2400 |
| gatggataat cgggtacgcg aggcttgtca gtacatcagc gatcacctgg cagacagcaa | 2460 |
| ttttgatatc gccagcgtcg cacagcatgt ttgcttgtcg ccgtcgcgtc tgtcacatct | 2520 |
| tttccgccag cagttaggga ttagcgtctt aagctggcgc gaggaccaac gtatcagcca | 2580 |
| ggcgaagctg cttttgagca ccacccgat gcctatcgcc accgtcggtc gcaatgttgg | 2640 |
| ttttgacgat caactctatt tctcgcgggt atttaaaaaa tgcaccgggg ccagcccgag | 2700 |
| cgagttccgt gccggttgtg aagaaaaagt gaatgatgta gccgtcaagt tgtcataatt | 2760 |
| ggtaacgaat cagacaattg acggcttgac ggagtagcat agggtttgca gaatccctgc | 2820 |
| ttcgtccatt tgacaggcac attatgcgaa ttcgctagca gatcttagtg acattagaaa | 2880 |
| accgactgta aaaagtacag tcggcattat ctcatattat aaaagccagt cattaggcct | 2940 |
| atctgacaat tcctgaatag agttcataaa caatcctgca tgataaccat cacaaacaga | 3000 |
| atgatgtacc tgtaaagata gcggtaaata tattgaatta cctttattaa tgaattttcc | 3060 |
| tgctgtaata atgggtagaa ggtaattact attattattg atatttaagt taaacccagt | 3120 |
| aaatgaagtc catggaataa tagaaagaga aaaagcattt tcaggtatag gtgttttggg | 3180 |
| aaacaatttc cccgaaccat tatatttctc tacatcagaa aggtataaat cataaaactc | 3240 |
| tttgaagtca ttctttacag gagtccaaat accagagaat gttttagata caccatcaaa | 3300 |
| aattgtataa agtggctcta acttatccca ataacctaac tctccgtcgc tattgtaacc | 3360 |
| agttctaaaa gctgtatttg agtttatcac ccttgtcact aagaaaataa atgcagggta | 3420 |
| aaatttatat ccttcttgtt ttatgtttcg gtataaaaca ctaatatcaa tttctgtggt | 3480 |
| tatactaaaa gtcgtttgtt ggttcaaata atgattaaat atctcttttc tcttccaatt | 3540 |
| gtctaaatca attttattaa agttcatttg atatgcctcc taaattttta tctaaagtga | 3600 |
| atttaggagg cttacttgtc tgctttcttc attagaatca atccttttt aaaagtcaat | 3660 |
| cc | 3662 |

<210> SEQ ID NO 99
<211> LENGTH: 5671
<212> TYPE: DNA
<213> ORGANISM: Artificial Sequence
<220> FEATURE:
<223> OTHER INFORMATION: Synthetic: plasmid

<400> SEQUENCE: 99

| | |
|---|---|
| atccggatat agttcctcct ttcagcaaaa aacccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttgt | 180 |
| cgacggagct cgaattcgga tccaacgatg ctgattgccg ttccggcaaa cgcggtccgt | 240 |

-continued

```
tttttcgtct cgtcgctggc agcctccggc cagagcacat cctcataacg gaacgtgccg    300
gacttgtaga acgtcagcgt ggtgctggtc tggtcagcag caaccgcaag aatgccaacg    360
gcagcaccgt cggtggtgcc atcccacgca accagcttac ggctggaggt gtccagcatc    420
agcggggtca ttgcaggcgc tttcgcactc aatccgccgg gcgcggttgc ggtatgagcc    480
gggtcactgt tgccctgcgg ctggtaatgg gtaaaggttt ctttgctcgt catggtaccc    540
agatctgggc tgtccatgtg ctggcgttcg aatttagcag cagcggtttc tttcatatgt    600
atatctcctt cttaaagtta aacaaaatta tttctagagg ggaattgtta tccgctcaca    660
attcccctat agtgagtcgt attaatttcg cgggatcgag atcgatctcg atcctctacg    720
ccggacgcat cgtggccggc atcaccggcg ccacaggtgc ggttgctggc gcctatatcg    780
ccgacatcac cgatggggaa gatcgggctc gccacttcgg gctcatgagc gcttgtttcg    840
gcgtgggtat ggtggcaggc cccgtggccg ggggactgtt gggcgccatc tccttgcatg    900
caccattcct tgcggcggcg gtgctcaacg gcctcaacct actactgggc tgcttcctaa    960
tgcaggagtc gcataaggga gagcgtcgag atcccggaca ccatcgaatg cgcaaaacc    1020
tttcgcggta tggcatgata gcgcccgaa gagagtcaat tcaggtggt gaatgtgaaa    1080
ccagtaacgt tatacgatgt cgcagagtat gccggtgtct cttatcagac cgtttcccgc    1140
gtggtgaacc aggccagcca cgtttctgcg aaaacgcggg aaaaagtgga agcggcgatg    1200
gcggagctga attacattcc caaccgcgtg gcacaacaac tggcgggcaa acagtcgttg    1260
ctgattggcg ttgccacctc cagtctggcc ctgcacgcgc cgtcgcaaat tgtcgcggcg    1320
attaaatctc gcgccgatca actgggtgcc agcgtggtgg tgtcgatggt agaacgaagc    1380
ggcgtcgaag cctgtaaagc ggcggtgcac aatcttctcg cgcaacgcgt cagtgggctg    1440
atcattaact atccgctgga tgaccaggat gccattgctg tggaagctgc ctgcactaat    1500
gttccggcgt tatttcttga tgtctctgac cagacaccca tcaacagtat tattttctcc    1560
catgaagacg gtacgcgact gggcgtggag catctggtcg cattgggtca ccagcaaatc    1620
gcgctgttag cgggcccatt aagttctgtc tcggcgcgtc tgcgtctggc tggctggcat    1680
aaatatctca ctcgcaatca aattcagccg atagcggaac gggaaggcga ctggagtgcc    1740
atgtccggtt ttcaacaaac catgcaaatg ctgaatgagg gcatcgttcc cactgcgatg    1800
ctggttgcca acgatcagat ggcgctgggc gcaatgcgcg ccattaccga gtccgggctg    1860
cgcgttggtg cggacatctc ggtagtggga tacgacgata ccgaagacag ctcatgttat    1920
atcccgccgt taaccaccat caaacaggat tttcgcctgc tggggcaaac cagcgtggac    1980
cgcttgctgc aactctctca gggccaggcg gtgaagggca atcagctgtt gcccgtctca    2040
ctggtgaaaa gaaaaaccac cctggcgccc aatacgcaaa ccgcctctcc ccgcgcgttg    2100
gccgattcat taatgcagct ggcacgacag gtttcccgac tggaaagcgg gcagtgagcg    2160
caacgcaatt aatgtaagtt agctcactca ttaggcaccg ggatctcgac cgatgccctt    2220
gagagccttc aacccagtca gctccttccg gtgggcgcgg ggcatgacta tcgtcgccgc    2280
acttatgact gtcttcttta tcatgcaact cgtaggacag gtgccggcag cgctctgggt    2340
cattttcggc gaggaccgct ttcgctggag cgcgacgatg atcggcctgt cgcttgcggt    2400
attcggaatc ttgcacgccc tcgctcaagc cttcgtcact ggtcccgcca ccaaacgttt    2460
cggcgagaag caggccatta tcgccggcat ggcggcccca cgggtgcgca tgatcgtgct    2520
cctgtcgttg aggacccggc taggctggcg gggttgcctt actggttagc agaatgaatc    2580
```

```
accgatacgc gagcgaacgt gaagcgactg ctgctgcaaa acgtctgcga cctgagcaac    2640
aacatgaatg gtcttcggtt tccgtgtttc gtaaagtctg gaaacgcgga agtcagcgcc    2700
ctgcaccatt atgttccgga tctgcatcgc aggatgctgc tggctaccct gtggaacacc    2760
tacatctgta ttaacgaagc gctggcattg accctgagtg atttttctct ggtcccgccg    2820
catccatacc gccagttgtt taccctcaca acgttccagt aaccgggcat gttcatcatc    2880
agtaacccgt atcgtgagca tcctctctcg tttcatcggt atcattaccc ccatgaacag    2940
aaatccccct tacacggagg catcagtgac caaacaggaa aaaccgccc ttaacatggc     3000 ccgctttatc agaagccaga cattaacgct tctggagaaa ctcaacgagc tggacgcgga    3060
tgaacaggca gacatctgtg aatcgcttca cgaccacgct gatgagcttt accgcagctg    3120
cctcgcgcgt ttcggtgatg acggtgaaaa cctctgacac atgcagctcc cggagacggt    3180
cacagcttgt ctgtaagcgg atgccgggag cagacaagcc cgtcagggcg cgtcagcggg    3240
tgttggcggg tgtcggggcg cagccatgac ccagtcacgt agcgatagcg gagtgtatac    3300
tggcttaact atgcggcatc agagcagatt gtactgagag tgcaccatat atgcggtgtg    3360
aaataccgca cagatgcgta aggagaaaat accgcatcag gcgctcttcc gcttcctcgc    3420
tcactgactc gctgcgctcg gtcgttcggc tgcggcgagc ggtatcagct cactcaaagg    3480
cggtaatacg gttatccaca gaatcagggg ataacgcagg aaagaacatg tgagcaaaag    3540
gccagcaaaa ggccaggaac cgtaaaaagg ccgcgttgct ggcgtttttc cataggctcc    3600
gcccccctga cgagcatcac aaaaatcgac gctcaagtca gaggtggcga aacccgacag    3660
gactataaag ataccaggcg tttccccctg gaagctccct cgtgcgctct cctgttccga    3720
ccctgccgct taccggatac ctgtccgcct ttctcccttc gggaagcgtg gcgctttctc    3780
atagctcacg ctgtaggtat ctcagttcgg tgtaggtcgt tcgctccaag ctgggctgtg    3840
tgcacgaacc ccccgttcag cccgaccgct gcgccttatc cggtaactat cgtcttgagt    3900
ccaacccggt aagacacgac ttatcgccac tggcagcagc cactggtaac aggattagca    3960
gagcgaggta tgtaggcggt gctacagagt tcttgaagtg gtggcctaac tacggctaca    4020
ctagaaggac agtatttggt atctgcgctc tgctgaagcc agttaccttc ggaaaaagag    4080
ttggtagctc ttgatccggc aaacaaacca ccgctggtag cggtggtttt tttgtttgca    4140
agcagcagat tacgcgcaga aaaaaaggat ctcaagaaga tcctttgatc ttttctacgg    4200
ggtctgacgc tcagtggaac gaaaactcac gttaagggat tttggtcatg aacaataaaa    4260
ctgtctgctt acataaacag taatacaagg ggtgttatga ccatattca acgggaaacg    4320 tcttgctcta ggccgcgatt aaattccaac atggatgctg atttatatgg gtataaatgg    4380
gctcgcgata atgtcgggca atcaggtgcg acaatctatc gattgtatgg gaagcccgat    4440
gcgccagagt tgtttctgaa acatggcaaa ggtagcgttg ccaatgatgt tacagatgag    4500
atggtcagac taaactggct gacggaattt atgcctcttc cgaccatcaa gcattttatc    4560
cgtactcctg atgatgcatg gttactcacc actgcgatcc ccgggaaaac agcattccag    4620
gtattagaag aatatcctga ttcaggtgaa atattgttg atgcgctggc agtgttcctg     4680
cgccggttgc attcgattcc tgtttgtaat tgtcctttta acagcgatcg cgtatttcgt    4740
ctcgctcagg cgcaatcacg aatgaataac ggtttggttg atgcgagtga ttttgatgac    4800
gagcgtaatg gctggcctgt tgaacaagtc tggaaagaaa tgcataaact tttgccattc    4860
tcaccggatt cagtcgtcac tcatggtgat ttctcacttg ataaccttat ttttgacgag    4920
gggaaattaa taggttgtat tgatgttgga cgagtcggaa tcgcagaccg ataccaggat    4980
```

```
cttgccatcc tatggaactg cctcggtgag ttttctcctt cattacagaa acggcttttt    5040
caaaaatatg gtattgataa tcctgatatg aataaattgc agtttcattt gatgctcgat    5100 gagttttct  aagaattaat tcatgagcgg atacatattt gaatgtattt agaaaaataa    5160
acaaataggg gttccgcgca catttccccg aaaagtgcca cctgaaattg taaacgttaa    5220
tattttgtta aaattcgcgt taaattttg  ttaaatcagc tcattttta  accaataggc    5280 cgaaatcggc aaaatccctt ataaatcaaa agaatagacc gagatagggt tgagtgttgt    5340
tccagtttgg aacaagagtc cactattaaa gaacgtggac tccaacgtca agggcgaaa     5400 aaccgtctat cagggcgatg gcccactacg tgaaccatca ccctaatcaa gttttttggg    5460
gtcgaggtgc cgtaaagcac taaatcggaa ccctaaaggg agcccccgat ttagagcttg    5520
acggggaaag ccggcgaacg tggcgagaaa ggaagggaag aaagcgaaag gagcgggcgc    5580
tagggcgctg gcaagtgtag cggtcacgct gcgcgtaacc accacacccg ccgcgcttaa    5640
tgcgccgcta cagggcgcgt cccattcgcc a                                   5671

<210> SEQ ID NO 100
<211> LENGTH: 2340
<212> TYPE: DNA
<213> ORGANISM: Artificial Sequence
<220> FEATURE:
<223> OTHER INFORMATION: Synthetic: plasmid

<400> SEQUENCE: 100
ggtaccaaag catgcaatga gctcagtaac ccgtatcgtg agcatcctct ctcgtttcat      60
cggtatcatt acccccatga acagaaatcc cccttacacg gaggcatcag tgaccaaaca    120
ggaaaaaacc gcccttaaca tggcccgctt tatcagaagc cagacattaa cgcttctgga    180
gaaactcaac gagctggacg cggatgaaca ggcagacatc tgtgaatcgc ttcacgacca    240
cgctgatgag ctttaccgca gctgcctcgc gcgtttcggt gatgacggtg aaaacctctg    300
acacatgcag ctcccggaga cggtcacagc ttgtctgtaa gcggatgccg ggagcagaca    360
agcccgtcag ggcgcgtcag cgggtgttgg cgggtgtcgg ggcgcagcca tgacccagtc    420
acgtagcgat agcggagtgt atactggctt aactatgcgg catcagagca gattgtactg    480
agagtgcacc attgcggtgt gaaataccgc acagatgcgt aaggagaaaa taccgcatca    540
ggcgctcttc cgcttcctcg ctcactgact cgctgcgctc ggtcgttcgg ctgcggcgag    600
cggtatcagc tcactcaaag gcggtaatac ggttatccac agaatcaggg gataacgcag    660
gaaagaacat gtgagcaaaa ggccagcaaa aggccaggaa ccgtaaaaag gccgcgttgc    720
tggcgttttt ccataggctc cgcccccctg acgagcatca caaaaatcga cgctcaagtc    780
agaggtggcg aaacccgaca ggactataaa gataccaggc gtttccccct ggaagctccc    840
tcgtgcgctc tcctgttccg accctgccgc ttaccggata cctgtccgcc tttctccctt    900
cgggaagcgt ggcgctttct catagctcac gctgtaggta tctcagttcg gtgtaggtcg    960
ttcgctccaa gctgggctgt gtgcacgaac cccccgttca gcccgaccgc tgcgccttat   1020
ccggtaacta tcgtcttgag tccaacccgg taagacacga cttatcgcca ctggcagcag   1080
ccactggtaa caggattagc agagcgaggt atgtaggcgg tgctacagag ttcttgaagt   1140
ggtggcctaa ctacggctac actagaagga cagtatttgg tatctgcgct ctgctgaagc   1200
cagttacctt cggaaaaaga gttggtagct cttgatccgg caaacaaacc accgctggta   1260
gcggtggttt ttttgtttgc aagcagcaga ttacgcgcag aaaaaaagga tctcaagaag   1320
```

```
                                            -continued
atcctttgat cttttctacg gggtctgacg ctcagtggaa cgaaaactca cgttaaggga    1380
ttttggtcat gaacaataaa actgtctgct tacataaaca gtaatacaag gggtgttatg    1440
agccatatca acgggaaacg ctcgagtacg tatctagagc aaagcttatc gtcgacatgc    1500
atctgcagcc cggggatcc  tcgcgacata tgactagtga attcgctagc agatcttagt    1560
gacattagaa aaccgactgt aaaaagtaca gtcggcatta tctcatatta taaaagccag    1620
tcattaggcc tatctgacaa ttcctgaata gagttcataa acaatcctgc atgataacca    1680
tcacaaacag aatgatgtac ctgtaaagat agcggtaaat atattgaatt acctttatta    1740
atgaattttc ctgctgtaat aatgggtaga aggtaattac tattattatt gatatttaag    1800
ttaaacccag taaatgaagt ccatggaata atagaaagag aaaaagcatt ttcaggtata    1860
ggtgttttgg gaaacaattt ccccgaacca ttatatttct ctacatcaga aaggtataaa    1920
tcataaaact ctttgaagtc attctttaca ggagtccaaa taccagagaa tgttttagat    1980
acaccatcaa aaattgtata aagtggctct aacttatccc aataacctaa ctctccgtcg    2040
ctattgtaac cagttctaaa agctgtattt gagtttatca cccttgtcac taagaaaata    2100
aatgcagggt aaaatttata tccttcttgt tttatgtttc ggtataaaac actaatatca    2160
atttctgtgg ttatactaaa agtcgtttgt tggttcaaat aatgattaaa tatctctttt    2220
ctcttccaat tgtctaaatc aattttatta aagttcattt gatatgcctc ctaaattttt    2280
atctaaagtg aatttaggag gcttacttgt ctgctttctt cattagaatc aatccttttt    2340
```

METHOD OF PREPARING PORCINE CIRCOVIRUS TYPE 2 CAPSID PROTEIN AND PHARMACEUTICAL COMPOSITION COMPRISING SAME

REFERENCE TO SEQUENCE LISTING SUBMITTED VIA EFS-WEB

This application includes an electronically submitted sequence listing in .txt format. The .txt file contains a sequence listing entitled "2018-10-05_5025-0280PUS1_ST25" created on Oct. 5, 2018 and is 175,337 bytes in size. The sequence listing contained in this .txt file is part of the specification and is hereby incorporated by reference herein in its entirety.

BACKGROUND OF THE INVENTION

Field of the Invention

The present invention relates to a preparation method of PCV2 capsid protein, particularly to a preparation method of PCV2 capsid protein by using a prokaryotic cell expression system.

Description of the Prior Art

Porcine circovirus type 2 (PCV2) is a viral pathogen that vastly affects the global swine industry. PCV2 mainly causes post-weaning multisystemic wasting syndrome (PMWS), whose symptoms are fever, lymphadenopathy, weight loss or weakness, difficulty breathing, diarrhea, body paleness, occasionally jaundice, etc. It may also cause porcine dermatitis and nephropathy syndrome (PDNS), infectious congenital tremor (ICT), and reproductive disorders. In addition, infection of PCV2 in combination with other viral or bacterial pathogens causes porcine respiratory disease complex (PRDC). The disease caused by infection of PCV2 in pigs results in a decrease in the survival rate and feed conversion rate, leading to serious economic losses for pig producers.

Twenty points of feeding and management for prevention and control of PCV2 in the field are proposed, such as all-in/all-out (AIAO), good hygiene management, elimination or segregation of pigs with severe illness, and vaccination. Among them, vaccination can effectively reduce the PCV2 infection rate and further increase the survival rate. PCV2 vaccines in the current field are divided into three categories, including inactivated PCV2 vaccines, inactivated baculovirus subunit vaccines, and inactivated PCV1-PCV2 chimeric virus vaccines (Beach And Meng, 2012; Chanhee, 2012).

Inactivated PCV2 vaccine is produced by infecting porcine kidney cell line PK-15 with PCV2, harvesting the virus, inactivating the virus, and mixing the virus with adjuvant. For inactivated baculovirus subunit vaccines, insect cells are transfected with baculovirus carrying ORF2 gene encoding PCV2 capsid protein to express antigen ORF2. If the antigen is expressed in a cell, the vaccine is prepared by ultrasonically crushing the culture medium containing the cells, inactivating the virus, and mixing the virus with adjuvant. If the antigen is secreted into the extracellular milieu, the vaccine is prepared by collecting the cell culture supernatant, inactivating the virus, and mixing the virus with adjuvant. The inactivated PCV1-PCV2 chimeric virus vaccines is prepared by replacing PCV1 ORF2 with PCV2 ORF2, infecting cells, harvesting the virus, inactivating the virus, and mixing the virus with adjuvant.

In view of the fact that the current PCV2 vaccine production methods are all based on the method of culturing viruses, these methods have the disadvantages of long preparation time and high production cost. To reduce the cost of PCV2 vaccines, researchers in the field tried to use recombinant E. coli with lower cost of culture for production of vaccine antigen ORF2. However, the method has issues of low production of ORF2, inability to form virus-like particles of the recombinant ORF2, complicated processes, or low immunity.

SUMMARY OF THE INVENTION

Therefore, it is an object of the present invention to provide a preparation method of PCV2 capsid protein to reduce the production time and the cost of PCV2 vaccine.

Another object of the present invention is to provide a composition for preventing PCV2 infection. The composition uses PCV2 capsid protein as an active component and contains a suitable adjuvant to provide a tool for prevention of PCV2 infection for the industry.

Another object of the present invention is to provide a preparation method of porcine interferon to reduce the production time and the cost of porcine interferon and to facilitate the application of porcine interferon in a composition for preventing PCV2 infection.

To achieve the above objects, the present invention provides a method for expressing a protein, comprising: (a) obtaining an arabinose-induced expression vector, wherein the arabinose-induced expression vector comprises an expression element and a nucleotide sequence encoding a target protein; wherein the expression element comprises: a promoter; a T7 phage translation enhancing element having SEQ ID NO: 01; and a ribosome binding site having SEQ ID NO: 02; (b) transforming the arabinose-induced expression vector into an E. coli host and inducing expression of the target protein; wherein the target protein is PCV2 capsid protein or porcine interferon.

Preferably, the −16 site of the promoter has SEQ ID NO: 03.

Preferably, the expression element has SEQ ID NO: 04.

Preferably, the arabinose-induce expression vector further comprises a nucleotide sequence encoding a fusion partner, and/or a nucleotide sequence encoding a marker molecule. Preferably, the fusion partner is MsyB of E. coli, YjgD of E. coli, D protein of Lambda phage, SUMO protein of Baker's yeast, or a combination thereof. Preferably, the marker molecule is: His tag, Strep II tag, FLAG tag, or a combination thereof.

Preferably, the target protein is PCV2 capsid protein encoded from SEQ ID NO: 09 or SEQ ID NO: 24. Preferably, the arabinose-induced expression vector has SEQ ID NO: 46.

Preferably, the porcine interferon is porcine interferon-α or porcine interferon-γ. Preferably, the target protein is porcine interferon, and the porcine interferon encoded from SEQ ID NO: 64 or SEQ ID NO: 76. Preferably, the arabinose-induced expression vector has SEQ ID NO: 80, SEQ ID NO: 87, or SEQ ID NO: 95. Preferably the method does not comprise a step of refolding the porcine interferon.

Preferably, the method further comprises a step (c) after the step (b): purifying the target protein. Preferably, the method further comprises a step (d) after the step (c): treating the target protein with a SUMO protease. Preferably, in the step (d), the weight ratio of the target protein to the SUMO protease is 4 to 20.

The present invention further provides a composition for preventing PCV2 infection, comprising: 2.5 to 250 µg/mL PCV2 capsid protein; 2.5 to 25 µg/mL porcine interferon-α; 2.5 to 25 µg/mL porcine interferon-γ; and a pharmaceutically acceptable carrier.

Preferably, the composition further comprises a pharmaceutically acceptable adjuvant. Preferably, the pharmaceutically acceptable adjuvant is: MONTANIDE™ ISA 563 VG adjuvant, MONTANIDE™ GEL 01 adjuvant, Freund's complete or incomplete adjuvant, aluminum gel, surfactant, polyanionic polymers, peptides, oil emulsions, or a combination thereof.

Preferably, the composition comprises: 3.5 to 170 µg/mL PCV2 capsid protein; 5 to 20 µg/mL porcine interferon-α; 5 to 20 µg/mL porcine interferon-γ; and a pharmaceutically acceptable carrier.

In summary, the present invention primarily provides a method for expressing a protein by using an arabinose-induced expression vector. The method of the present invention efficiently facilitates synthesis of PCV2 capsid protein and porcine interferon used as an adjuvant in vaccine. On the other hand, the pharmaceutical composition of the present invention combines the capsid protein and other advantageous components at an appropriate ratio to obtain an excellent immunogenicity-inducing effect. Accordingly, the disclosure of the present invention has significant benefits for prevention and treatment of PCV2 in the field.

BRIEF DESCRIPTION OF THE DRAWINGS

FIG. 1 is a schematic diagram of five expression vectors of PCV2 capsid proteins prepared in Example 1.

FIG. 2 shows the results of protein expression of the five expression vectors made in Example 1 in *E. coli* hosts after transformation thereof by using protein electrophoresis and western blot. (A) Results of protein electrophoresis. (B) Results of western blot; lane 1: BL21(DE3)/pET29a; lane 2: BL21(DE3)/pET-SUMO-ORF2; lane 3: BL21(DE3)/pET-OPTSUMO-ORF2; lane 4: Rosetta2/pET-SUMO-ORF2; lane 5: BL21(DE3)/pET-SUMO-OPTORF2; lane 6: BL21 (DE3)/pET-OPTSUMO-OPTORF2; lane 7: BL21/pBA-OPTSUMO-OPTORF2.

FIG. 3 shows solubility of the fusion proteins expressed by the four expression vectors made in Example 1 in *E. coli* hosts after transformation thereof by using protein electrophoresis. T: total cell lysate; S: soluble protein fraction; IS: insoluble protein fraction. The arrows indicate the target proteins.

FIG. 4 shows an electrophoretogram of proteins expressed by *E. coli* BL21(DE3) harboring plasmid pBA-OPTSUMO-OPTORF2 and protein purification by immobilized metal ion affinity chromatography. Lane 1: total cell lysate of *E. coli* BL21 (pBA-OPTSUMO-OPTORF2); lane 2: purified fusion protein.

FIG. 5 shows the results of protein expression of the recombinant SUMO protease (SUMOPH) and the recombinant D-SUMO protease (DSUMOPH) in host cells [*E. coli* BL21 (DE3)] in Example 2 by using protein electrophoresis and western blot. (A) Results of protein electrophoresis. (B) Results of western blot. T: total cell lysate; S: soluble protein fraction; IS: insoluble protein fraction. The arrows indicate the target proteins.

FIG. 6 shows an electrophoretogram of proteins expressed by *E. coli* BL21 (DE3) harboring plasmids pET-SUMOPH and pET-D-SUMOPH and protein purification by immobilized metal ion affinity chromatography. Lane 1: purified SUMO protease (SUMOPH); lane 2: purified D-SUMO protease (DSUMOPH).

FIG. 7 shows an electrophoretogram of purified SUMO-ORF2, digested SUMO-ORF2 and purified ORF2. Lane 1: purified SUMO-ORF2 fusion protein. Lane 2: cleavage mixture of SUMO-ORF2 with D-SUMO protease. Lane 3: purified ORF2 (cleavage mixture filtrated with a 100 kDa molecular weight cut off membrane).

FIG. 8 shows transmission electron microscope images of virus-like particles of SUMO-ORF2 fusion protein (A), digested SUMO-ORF2 (SUMO-ORF2 fusion protein cleaved by protease) (B), purified ORF2 (C).

FIG. 9 shows electrophoretograms of protein expression of recombinant porcine interferon in Example 3; T: total cell lysate; S: soluble protein fraction. (A) pET-OPTPIFNAH/*E. coli* Shuffle; (B) pBA-OPTPIFNAH/*E. coli* Shuffle; (C) pET-SUMO-OPTPIFNAH/*E. coli* Shuffle; (D) pET-OPT-SUMO-OPTPIFNAH/*E. coli* Shuffle; (E) pBA-OPTSUMO-OPTPIFNAH/*E. coli* Shuffle; (F) pET-OPTPIFNRH/*E. coli* BL21 (DE3); (G) pET-SUMO-OPTPIFNRH/*E. coli* BL21 (DE3); (H) pET-OPTSUMO-OPTPIFNRH/*E. coli* BL21 (DE3); (I) pBA-OPTSUMO-OPTPIFNRH/*E. coli* BL21 (DE3). The arrows indicate the target proteins.

FIG. 10 shows electrophoretograms of purified recombinant porcine interferon expressed in Example 3. Lane 1: purified fusion protein expressed by *E. coli* Shuffle (pET-OPTPIFNAH); lane 2: fusion protein expressed by *E. coli* Shuffle (pBA-OPTSUMO-OPTPIFNAH) after being cleaved by D-SUMO protease [pET-D-SUMOP/*E. coli* BL21(DE3) cell disruption] and purified; lane 3: fusion protein expressed by *E. coli* BL21(DE3) (pET-OPTSUMO-OPTPIFNRH) after being cleaved by D-SUMO protease [pET-D-SUMOP/*E. coli* BL21(DE3) cell disruption] and purified.

FIG. 11 shows the ELISA results of anti-PCV2 antibody titers in pigs induced by the samples of Experiment 3 in Example 4.

FIG. 12 shows the level of viremia reduced in pigs by the samples of Experiment 3 in Example 4.

FIG. 13 shows the ELISA results of anti-PCV2 antibody titers in pigs induced by the samples of Experiment 4 in Example 4.

FIG. 14 shows the level of viremia reduced in pigs by the samples of Experiment 4 in Example 4.

FIG. 15 shows the ELISA results of anti-PCV2 antibody titers in pigs induced by the samples of Experiment 5 in Example 4.

DETAILED DESCRIPTION OF THE EMBODIMENTS

As described above, although attempts have been made in the field to produce PCV2 capsid protein through the *E. coli* expression system, as at the time of the present invention, the disadvantages of low yields have not yet been overcome. Therefore, there are obstacles to progress of the epidemic prevention of PCV2.

The method of the present invention uses the arabinose-inducing expression element disclosed by the applicants of the present invention in Taiwan patent application No. 103146225 (filing date: Dec. 30, 2014) to prepare PCV2 capsid proteins. The entire contents of the Taiwan patent application No. 103146225 are incorporated in the present invention as references.

As used herein, "a target protein" refers to a protein that is intended to be expressed by a prokaryotic expression system. In the present invention, the aforementioned target protein is a PCV2 capsid protein, porcine interferon-α, or porcine interferon-γ.

As used herein, "nucleotide sequence encoding the target protein" or other similar description refers to a nucleotide sequence which can form the aforementioned target protein by an in vivo or in vitro transcription/translation mechanism. Accordingly, the "nucleotide sequence encoding PCV2 capsid protein" or "nucleotide sequence encoding porcine interferon" of the present invention is also defined as above. Similarly, the "nucleotide sequence encoding the fusion partner" or the "nucleotide sequence encoding the marker molecule" of the present invention is also defined as before.

As used herein, "fusion partner" refers to a molecule that is used to increase the solubility of an aforementioned synthesized target protein. For the above purpose, the nucleotide sequence encoding a fusion partner and the nucleotide sequence encoding the aforementioned target protein are constructed in the same expression vector by a genetically engineering method, so that the aforementioned target protein is synthesized with the aforementioned fusion partner as a fusion protein. The aforementioned fusion partner is, for example but not limited to, MsyB of *E. coli*, YjgD of *E. coli*, D protein of Lambda phage, SUMO protein of Baker's yeast, or a combination thereof.

As used herein, "marker molecule" refers to a molecule that facilitates the observation of the synthesis of the aforementioned target protein or facilitates the purification of the aforementioned target protein. For the above purpose, the nucleotide sequence of a marker molecule and the nucleotide sequence of the aforementioned target protein are constructed in the same expression vector in a genetically engineered method, so that the aforementioned target protein is synthesized with the aforementioned marker molecule as a fusion protein. The aforementioned marker molecule is, for example but not limited to, a His tag, a Strep II tag, a FLAG tag, or a combination thereof.

The first aspect of the present invention is related to a method for preparing a PCV2 capsid protein, porcine interferon-α, or porcine interferon-γ. The aforementioned method comprises (a) obtaining an arabinose-induced expression vector, wherein the arabinose-induced expression vector comprises an expression element and a nucleotide sequence encoding a target protein; and (b) transforming the arabinose-induced expression vector into an *E. coli* host to induce expression of the target protein.

In an alternative embodiment, the aforementioned target protein is a PCV2 capsid protein. In an alternative embodiment, the aforementioned target protein is porcine interferon-α or porcine interferon-γ.

In a preferred embodiment, the aforementioned expression elements are as described in Taiwan patent application No. 103146225 (filing date: Dec. 30, 2014) by the applicants of the present invention. Specifically, the aforementioned expression element comprises: a promoter; a T7 phage translation enhancing element; and a ribosome binding site. For example, the aforementioned performance element is the araB-M11 expression element described in the Taiwan patent application No. 103146225.

In a preferred embodiment, the aforementioned T7 phage translation enhancing element has SEQ ID NO: 01. In a preferred embodiment, the aforementioned ribosome binding site has SEQ ID NO: 02. In a preferred embodiment, the −16 site of the aforementioned promoter has SEQ ID NO: 03. In a preferred embodiment, the aforementioned expression element has SEQ ID NO: 04.

In an alternative embodiment, the aforementioned step (b) is further followed by a step (c) of purifying the aforementioned target protein. When a His tag is used as the marker molecule in the method of the present invention, the target protein may be purified by immobilized metal ion affinity chromatography.

In an alternative embodiment, when the SUMO protein is used as the aforementioned fusion partner in the method of the present invention, a step (d) is further included after the aforementioned step (c): the target protein is treated with a SUMO protease. The "treated" mentioned above refers to that the SUMO fusion partner is cut by the SUMO protease so that the target protein is separated from the SUMO protein.

In an alternative embodiment, the SUMO protease is produced by a T7 expression vector. In a preferred embodiment, in the aforementioned treatment, the weight ratio of the target protein to the SUMO protease is 4 to 20.

In a preferred embodiment, the aforementioned method does not include a refolding step of the porcine interferon. A person of ordinary skill in the art can understand that the "refolding step" in a prokaryotic cell expression system means the process of forming a tertiary structure or a quaternary structure of a polypeptide by dissolving the inclusion body using urea or guanidine hydrochloride and then refolding the resulting polypeptide by dialysis and other steps. Therefore, those of ordinary skill in the art can understand that the "does not include a refolding step of the porcine interferon" of the present invention means that the polypeptides prepared in the method of the present invention can self-fold into the desired protein without using urea or guanidine hydrochloride, and dialysis.

In an alternative embodiment, the host is an *E. coli*. Preferably, the *E. coli* is BL21, BL21 (DE3), Rosetta 2, or Shuffle.

The second aspect of the present invention is a composition for preventing PCV2 infection, comprising PCV2 capsid protein, porcine interferon-α, porcine interferon-γ, and a pharmaceutical acceptable carrier.

In a preferred embodiment, the composition for preventing PCV2 infection comprises 2.5 to 250 μg/mL of PCV2 capsid protein; 2.5 to 25 μg/mL of porcine interferon-α; 2.5 to 25 μg/mL of porcine interferon-γ; and a pharmaceutically acceptable carrier. In yet another preferred embodiment, the composition for preventing PCV2 infection comprises 3.5 to 170 μg/mL of PCV2 capsid protein; 5 to 20 μg/mL porcine of interferon-α; 5 to 20 μg/mL of porcine interferon-γ; and a pharmaceutically acceptable carrier.

In a preferred embodiment, the PCV2 capsid protein is produced by the method of the present invention. In a preferred embodiment, the porcine interferon-α and/or the porcine interferon-γ are those produced by the method of the present invention.

The "pharmaceutically acceptable carrier" of the present invention refers to a substance that does not have negative impact on the purpose of preventing PCV2 infection by the PCV2 capsid protein, the porcine interferon-α and/or the porcine interferon-γ in the composition from the medical/pharmaceutical aspects. In an alternative embodiment, the pharmaceutically acceptable carrier is, for example but not limited to, water, phosphate buffered saline, alcohol, glycerin, chitin, alginate, chondroitin, vitamin E, minerals, or combinations thereof.

In a preferred embodiment, the composition further comprises a pharmaceutically acceptable adjuvant. The "pharmaceutically acceptable adjuvant" of the present invention refers to a substance that facilitates the purpose of preventing PCV2 infection by the PCV2 capsid protein, the porcine interferon-α and/or the porcine interferon-γ in the composition and increases immunity from the medical/pharmaceutical aspects. In an alternative embodiment, the pharmaceutically acceptable adjuvant is, for example but not limited to, MONTANIDE™ ISA 563 VG adjuvant, MONTANIDE™ GEL 01 adjuvant, Freund's complete or incomplete adjuvant, aluminum gel, surfactant, polyanionic polymers, peptides, oil emulsions, or combinations thereof. In a preferred embodiment, the pharmaceutically acceptable adjuvant is MONTANIDE™ ISA 563 VG adjuvant, MONTANIDE™ GEL 01 adjuvant, or a combination thereof.

The research process of the present invention will be further detailed in the following examples. However, the following contents only illustrate the features of the present invention for better understanding. Those of ordinary skill in the art can revise the following contents without departing from the spirit of the present invention and change them based on the general knowledge in the field, but still fall within the scope of the present invention.

Example 1: Construction of PCV2 Capsid Protein (PCV2 ORF2) Expression Vector Isolation and Sequencing of PCV2 Virus Lymphoid organs, such as spleen and lymph nodes, of sick pigs were obtained from pig farms having PCV2 infection (Yunlin, Taiwan). After being cut by a sterilized scissor, the lymphoid organs were grinded with a sterile grinding pestle and a grinding stick, and an appropriate amount of sterile phosphate buffer solution was added and mixed to make emulsion. The emulsion was centrifuged (6,000×g, 20 minutes) to collect the supernatant, and then the supernatant was filtered through a sieve to remove tissue debris. DNA extraction was performed by using a DNA purification kit (DNeasy Blood & Tissue kit; Qiagen, USA). One hundred (100) μL of the emulsion supernatant was added to 180 μL of ATL Buffer and 20 μL of proteinase K (10 mg/mL) and incubated at 56° C. for 2 hours. After that, add 200 μL of absolute alcohol and mix well. All solutions were pipetted to a spin column, which was placed in a collection tube, and centrifuged at 6,000×g for 1 minute. The spin column was placed in a new collection tube, 500 μL of AW1 Buffer was added to the tube, and the tube was centrifuged at 6,000×g for 1 minute. Place the spin column in a new collection tube, add 500 μL of AW2 Buffer to the spin column, and the spin column was centrifuged at 20,630×g for 5 minutes. The spin column was placed in a sterile eppendorf, and an appropriate amount of sterile deionized water was added to elute the DNA.

Primers of PCVF (5'-ACCAGCGCACTTCGGCAGC-3'; SEQ ID NO: 05) and PCVR (5'-AATACTTACAGCG-CACTTCTTTCGTTTTC-3; SEQ ID NO: 06) were designed, and PCV2 genomic DNA was amplified by polymerase chain reaction (PCR). The volume of the PCR reaction mixture was 100 μL, which included 10 μL of DNA extracted from the lymphoid organs, 10 μL of 10× Taq buffer, 200 μM of dATP, dTTP, dGTP and dCTP, 1 μM of amplification primers, and 2.5 U of DreamTaq DNA Polymerase. (Thermo, USA). PCR reaction conditions were 94° C. for 5 minutes (1 cycle); 94° C. for 30 seconds, 59° C. for 30 seconds, 72° C. for 1 minute and 30 seconds (35 cycles); 72° C. for 7 minutes (1 cycle). DNA electrophoresis was used to confirm the presence of a DNA fragment with predicted size.

The PCR product was recovered by PCR-M™ Clean Up kit (GMbiolab, Taiwan) and subjected to TA cloning by using yT&A Cloning Vector Kit (Yeastern, Taiwan). The experimental procedure was carried out based on the manufacturer's Manual for yT&A Cloning Vector Kit. Five (5) μL of the recovered and purified PCR product was mixed well with 2 μL of yT&A vector, 1 μL of ligation buffer A, 1 μL of ligation buffer B, and 1 μL of T4 DNA ligase (2 unit/μL). The mixture was incubated at 22° C. for 30 minutes. One (1) μL of the ligation mixture was transformed into E. coli ECOS 9-5 (Yeastern, Taiwan). The transformed cells were added to 1 mL of SOC recovery medium and shaken at 37° C., 250 rpm for 60 minutes. After that, a suitable amount of the bacterial solution was applied to a solid medium containing ampicillin (a final concentration of 100 μg/mL) and cultured at 37° C. for 16 hours.

Afterwards, the transformants were selected by colony polymerase chain reaction. The procedure of colony polymerase chain reaction is described as follows. First, 50 μL of 2× Premix Reaction Buffer (GMbiolab, Taiwan), 0.5 μL of 100 mM PCVF primer, 0.5 μL of 100 mM PCVR primer, and 49 μL of sterile water were add into an eppendorf and mix well. The PCR reaction solution was dispensed into PCR tubes (10 μL/tube). The PCR was performed after the colony was put in the PCR tube with a toothpick. PCR reaction conditions was 95° C. for 5 minutes (1 cycle); 95° C. for 30 seconds, 59° C. for 30 seconds, 72° C. for 1 minute and 30 seconds (25 cycles); 72° C. for 7 minutes (1 cycle). DNA electrophoresis was used to confirm the presence of the DNA fragments with predicted size. After confirming that the recombinant plasmids in the transformants carried insert DNA, the plasmids in the transformants were extracted and DNA sequencing was performed (Tri-I Biotech, Inc.). The plasmid containing PCV2 DNA was named pTA-PCV2.

Amplification and Cod on Optimization of ORF2 Gene (ie, the Gene Encoding Capsid Protein)

(1) Amplification of ORF2 Gene:

Using the pTA-PCV2 as a template and performing amplification of the ORF2 gene by using the ORF2F/ORF2R primer set (ORF2F; 5'-CAATATGGATCCATGACGTATC-CAAGGAGGCGTTTC-3; SEQ ID NO: 07 and ORF2R; 5'-GATATAGTCGACTTAGGGTT-TAAGTGGGGGGTCTTTAAGATTAA-3'; SEQ ID NO: 08). The 50 μL PCR reaction mixture contained 1×GDP-HiFi PCR Buffer B, 200 μM dATP, dTTP, dGTP and dCTP, 1 μM amplification primers, 100 ng pTA-PCV2, and 1 U GDP-HiFi DNA polymerase. The PCR reaction condition was 96° C. for 2 minutes (1 cycle); 94° C. for 30 seconds, 60° C. for 30 seconds, 68° C. for 30 seconds (35 cycles); 68° C. for 5 minutes (1 cycle). Agarose gel electrophoresis was used to confirm whether the PCR product contained DNA fragments with predicted size. Next, the PCR product was recovered by using the PCR-M™ Clean Up kit. Based on the sequencing results, the sequence of the ORF2 gene is shown as SEQ ID NO: 09.

(2) Gene Synthesis of Codon-Optimized ORF2 (OP-TORF2):

The amino acid sequence of ORF2 was reversed to the nucleotide sequence based on the preferred codons of E. coli. Primers were designed based on the aforementioned nucleotide sequences: OPTORF2-T1, OPTORF2-T2, OPTORF2-T3, OPTORF2-T4, OPTORF2-T5, OPTORF2-T6, OPTORF2-T7, OPTORF2-T8, OPTORF2-T9, OPTORF2-T10, OPTORF2-T11, OPTORF2-T12, OPTORF2F, and OPTORF2R. The sequences of primers are shown in Table 1.

TABLE 1

Primers used for synthesis of the codon-optimized ORF2 (OPTORF2) gene.

| Name | SEQ ID NO | Sequences (5' to 3') |
|---|---|---|
| OPTORF2-T1 | SEQ ID NO: 10 | ATGACCTACCCGCGTCGTCG TTTCCGTCGTCGTCGTCACC GTCCGCGTTCTCACCTGGGT CAGATCCTGCGTC |
| OPTORF2-T2 | SEQ ID NO: 11 | AGACGGGTGTTGAAGATACC GTTTTTACGACGCCAACGGT AACGGTGACGCGGGTGAACC AGCCACGGACGACGACGCAG GATCTGACCCAGG |
| OPTORF2-T3 | SEQ ID NO: 12 | AACGGTATCTTCAACACCCG TCTGTCTCGTACCTTCGGTT ACACCGTTAAAGCGTCTACC GTTCGTACCCCGTCTTG |
| OPTORF2-T4 | SEQ ID NO: 13 | ATTTTGTTGGTACCACCACC CGGCGGAACGAAGTCGTTGA TGTTGAAACGCATCATGTCA ACCGCCCAAGACGGGGTACG AACGG |
| OPTORF2-T5 | SEQ ID NO: 14 | CGGGTGGTGGTACCAACAAA ATCTCTATCCCGTTCGAATA CTACCGTATCCGTAAAGTTA AAGTTGAGTTTTGGCCGTGC TCTC |
| OPTORF2-T6 | SEQ ID NO: 15 | GTAACGAAGTTGTCGTCCAG GATAACCGCGGTAGAACCAA CACCACGGTCACCCTGGGTG ATCGGAGAGCACGGCCAAAA CTCAAC |
| OPTORF2-T7 | SEQ ID NO: 16 | GTTATCCTGGACGACAACTT CGTTACCAAAGCGACCGCGC TGACCTACGACCCGTACGTT AACTACTCTTCTCGTCACAC CATCCCGCAG |
| OPTORF2-T8 | SEQ ID NO: 17 | CGGCTGGAAGTAGTCGATGG TAGAGTCCAGAACCGGTTTC GGGGTGAAGTAACGAGAGTG GTAAGAGAACGGCTGCGGGA TGGTGTGACG |
| OPTORF2-T9 | SEQ ID NO: 18 | CTACCATCGACTACTTCCAG CCGAACTCTAAACGTAACCA GATCTGGCTGCGTCTGCAGA CCTCTGCGAACGTTG |
| OPTORF2-T10 | SEQ ID NO: 19 | CTGGTCGTATTTAGAGTTTT CGAACGCGGTACCCAGACCA ACGTGGTCAACGTTCGCAGA GGTCTGC |
| OPTORF2-T11 | SEQ ID NO: 20 | CGTTCGAAAACTCTAAATAC GACCAGGACTACAACATCCG TGTTACCATGTACGTTCAGT TCCG |
| OPTORF2-T12 | SEQ ID NO: 21 | TTACGGTTTCAGCGGCGGGT CTTTCAGGTTAAACTCACGG AACTGAACGTACATGGTAAC |
| OPTORF2F | SEQ ID NO: 22 | GATATAGGATCCATGACCTA CCCGCGTCGTCGTTTC |
| OPTORF2R | SEQ ID NO: 23 | CAATATGTCGACTTATTACG GTTTCAGCGGCGGGTC |

OPTORF2-T1 to OPTORF2-T12 were used as template primers, and OPTORF2 and OPTORF2R were used as amplification primers. Overlapping-extension polymerase chain reaction (OEPCR) was used to massively amplify the codon-optimized ORF2 gene. The 50 μL PCR reaction mixture contained 1×GDP-HiFi PCR Buffer B, 200 μM dATP, dTTP, dGTP and dCTP, 1 μM of each primer, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit. Based on the sequencing results, the sequence of the codon-optimized ORF2 gene is shown as SEQ ID NO: 24.

Amplification and Codon Optimization of SUMO Genes
(1) Amplification of SUMO Gene:

The Baker's yeast (*Saccharomyces cerevisiae*) isolated from DIY instant yeast of Sun Right Food Co. was inoculated into an YPD (20% peptone, 10% yeast extract, 20% glucose; pH 6.5) medium and shake-cultured at 30° C., 200 rpm for 16 hours. After cultivation, extraction of the yeast genome was performed by using a YeaStar™ Genomic DNA kit (Zymo Research, USA). 1.5 mL of the overnight culture broth was added to an eppendorf, collect the bacterial fractions by centrifugation (2,000×g, 5 minutes, room temperature), and 120 μL of YD Digestion Buffer and 5 μL of R-Zymolase was mixed thoroughly and incubated at 37° C. for 1 hour. Then 120 μL of YD Lysis Buffer was added to the mixture and gently mixed several times. Two hundred and fifty (250) μL of chloroform was added to the mixture and shook for 1 minute. The supernatant was collected by centrifugation (10,000×g, 2 minutes, room temperature). A spin column was placed in a collection tube, and the supernatant was added into the spin column. After centrifugation (10,000×g, 1 minute, room temperature), the filtrate was discarded. 300 μL of DNA Wash Buffer was added to the spin column, the spin column was centrifuged (10,000× g, 1 minute, room temperature), the filtrate was discarded, and this procedure was repeated once. The spin column was placed in a sterile eppendorf, an appropriate amount of elution solution was added to the spin column, and the spin column and the eppendorf were centrifuged (10,000×g, 2 minutes, room temperature) to elute the genomic DNA.

The SUMO gene was amplified by using the genomic DNA of *Saccharomyces cerevisiae* obtained in the previous paragraph as template and using SUMOF (5'-GATATAGG-TACCATGTCGGACTCAGAAGTCAATCAAG-3; SEQ ID NO: 25)/SUMOR (5'-CAATATGGATCCACCAC-CAATCTG TTCTCTGTGAGC-3; SEQ ID NO: 26) as the primer set. The 50 μL PCR reaction mixture contained 1× GDP-HiFi PCR Buffer B, 200 μM dATP, dTTP, dGTP and dCTP, 1 μM of amplification primers, 200 ng of the genomic DNA of *Saccharomyces cerevisiae*, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

(2) Gene Synthesis of Codon-Optimized SUMO (OPT-SUMO) Gene:

The amino acid sequence of SUMO was reversed to the nucleotide sequence based on the preferred codons of *E. coli*. Primers were designed based on the aforementioned nucleotide sequences: OPTSUMO-T1, OPTSUMO-T2, OPTSUMO-T3, OPTSUMO-T4, OPTSUMO-T5, OPTSUMO-T6, OPTSUMO-T7, OPTSUMO-T8, OPTSUMOF, and OPTSUMOR. The sequences are shown in Table 2.

TABLE 2

Primers used for synthesis of the codon-optimized SUMO (OPTSUMO) gene.

| Name | SEQ ID NO | Sequence (5' to 3') |
|---|---|---|
| OPTSUMO-T1 | SEQ ID NO: 27 | ATGAGCGATAGCGAAGTGA ACCAAGAAGCGAAACCGGA AGTGAAACCGGAAGTGAAA C |
| OPTSUMO-T2 | SEQ ID NO: 28 | GCTGCCGTCACTAACTTTC AGGTTGATGTGGGTTTCCG GTTTCACTTCCGGTTTCAC TTCC |
| OPTSUMO-T3 | SEQ ID NO: 29 | CCTGAAAGTTAGTGACGGC AGCTCTGAAATTTTCTTTA AGATCAAAAAGACCACGCC GCTGC |
| OPTSUMO-T4 | SEQ ID NO: 30 | TGCCCTGACGTTTGGCAAA CGCTTCCATCAGGCGACGC AGCGGCGTGGTCTTTTT |
| OPTSUMO-T5 | SEQ ID NO: 31 | TTTGCCAAACGTCAGGGCA AGGAAATGGATAGTCTGCG TTTCCTGTATGACGG |
| OPTSUMO-T6 | SEQ ID NO: 32 | TTCCGGGGTTTGATCCGCC TGGATGCGAATACCGTCAT ACAGGAAACGCAGAC |
| OPTSUMO-T7 | SEQ ID NO: 33 | GCGGATCAAACCCCGGAAG ACCTGGACATGGAAGACAA CGACATTATCGAAGC |
| OPTSUMO-T8 | SEQ ID NO: 34 | GCCGCCGATTTGTTCACGG TGTGCTTCGATAATGTCGT TGTCTTCC |
| OPTSUMOF | SEQ ID NO: 35 | CAATATGGTACCATGAGCG ATAGCGAAGTGAACCAAG |
| OPTSUMOR | SEQ ID NO: 36 | GATATAGGATCCGCCGCCG ATTTGTTCACGG |

OPTSUMO-T1 to OPTSUMO-T8 were used as template primers, and OPTSUMOF and OPTSUMOR were used as amplification primers. Overlapping-extension polymerase chain reaction was used to massively amplify the codon-optimized SUMO gene. The 50 µL PCR reaction mixture contained 1× GDP-HiFi PCR Buffer B, 200 µM dATP, dTTP, dGTP and dCTP, 1 µM of each primer, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up kit. Based on the sequencing results, the sequence of the codon-optimized SUMO gene is shown as SEQ ID NO: 37.

Construction of Expression Vector of ORF2 Fusion Protein (1) Construction of pET-DRAHIS:

The PCR reaction was carried out by using pET29a as the template and DRAF (5'-GATATACATAT-GAAAAAAAAATTCGTATCGCATCACCATCACCAT-CACAGCG GTGGTGGTACCCCAGATCTGGGTAC-CCTGG-3; SEQ ID NO: 38)/T7 terminator (GCTAGTTATTGCTCAGCGG; SEQ ID NO: 39) as the primer set. The 50 µL PCR reaction mixture contained 1× Ex Taq™ buffer, 200 µM dATP, dTTP, dGTP, and dCTP, 1 µM amplification primers, 100 ng pET29a, and 1.25 U TakaRa Ex Taq™ DNA polymerase (Takara, Japan). The PCR reaction condition was 94° C. for 5 minutes (1 cycle); 94° C. for 30 seconds, 55° C. for 30 seconds, 72° C. for 50 seconds (35 cycles); 72° C. for 7 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with NdeI and SalI, the DNA fragments were ligated into pET29a cut with the same restriction enzymes by using T4 DNA ligase. The ligated products were transformed into E. coli XL1-blue (Protech, Taiwan). The transformants were randomly selected for confirmation of DNA sequences. The plasmid with the correct DNA sequence was named pET-DRAHIS. This plasmid has a start codon followed with the downstream sequence (DS) AAAAAAAAATTCGTATCG (SEQ ID NO: 40) and the His tag DNA sequence CATCACCATCACCAT-CAC (SEQ ID NO: 41).

(2) Construction of the pET-SUMO-ORF2 Expression Vector:

After the SUMO gene was amplified from Saccharomyces cerevisiae genome and cut with KpnI and BamHI, the DNA fragment was ligated into pET-DRAHIS cut with the same restriction enzymes by using T4 DNA ligase. The ligated product was transformed into E. coli ECOS 9-5. Transformants were selected by colony polymerase chain reaction. After confirming that the recombinant plasmids in the transformants did carry the inserted DNA by DNA electrophoresis, the plasmids in the transformants were extracted and the DNA was sequenced. The plasmid with the correct DNA sequence was named pET-SUMO.

After the ORF2 gene amplified from the PCV2 Yunlin virus genome was cut with BamHI and SalI, the DNA fragment was inserted into pET-SUMO cut with the same restriction enzymes by using T4 DNA ligase. The ligated product was transformed into E. coli ECOS 9-5. Transformants were selected by colony polymerase chain reaction. After confirming that the recombinant plasmids in the transformants did carry the inserted DNA by DNA electrophoresis, the plasmids in the transformant were extracted and the DNA was sequenced. The plasmid with the correct DNA sequence is named pET-SUMO-ORF2, which has the sequence of SEQ ID NO: 42.

(3) Construction of the pET-OPTSUMO-ORF2 Expression Vector:

After the synthetic OPTSUMO gene was cut with KpnI and BamHI, the DNA fragment was ligated into pET-DRAHIS cut with the same restriction enzymes by using T4 DNA ligase. The ligated product was transformed into E. coli ECOS 9-5. Transformants were selected by colony polymerase chain reaction. After confirming that the recombinant plasmid in the transformants did carry the inserted DNA by DNA electrophoresis, the plasmids in the transformants were extracted and the DNA was sequenced. The plasmid with the correct DNA sequence was named pET-OPTSUMO.

After the ORF2 gene amplified from the PCV2 Yunlin virus genome was cut with BamHI and SalI, the DNA fragment was ligated into pET-OPTSUMO cut with the same restriction enzymes by using T4 DNA ligase. The ligated product was transformed into E. coli ECOS 9-5.

Transformants were selected by colony polymerase chain reaction. After confirming that the recombinant plasmid in the transformants did carry the inserted DNA by DNA electrophoresis, the plasmids in the transformants were extracted and the DNA was sequenced. The plasmid with the correct DNA sequence is named pET-OPTSUMO-ORF2, which has SEQ ID NO: 43.

(4) Construction of the pET-SUMO-OPTORF2 Expression Vector:

After the synthetic OPTORF2 gene was cut with BamHI and SalI, the DNA fragment was ligated into pET-SUMO cut with the same restriction enzymes by using T4 DNA ligase. The ligated product was transformed into *E. coli* ECOS 9-5. Transformants were selected by colony polymerase chain reaction. After confirming that the recombinant plasmid in the transformants did carry the inserted DNA by DNA electrophoresis, the plasmids in the transformant were extracted and the DNA was sequenced. The plasmid with the correct DNA sequence is named pET-SUMO-OPTORF2, which has SEQ ID NO: 44.

(5) Construction of the pET-OPTSUMO-OPTORF2 Expression Vector:

After the synthetic OPTORF2 gene was cut with BamHI and SalI, the DNA fragment was inserted into pET-OPT-SUMO cut with the same restriction enzymes by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformants were extracted and the DNA was sequenced. The plasmid with the correct DNA sequence is named pET-OPTSUMO-OPTORF2, which has SEQ ID NO: 45.

(6) Construction of the pBA-OPTSUMO-OPTORF2 Expression Vector:

The pBA-OPTSUMO-OPTORF2 constructed in this experiment was obtained by inserting the DNA fragment of OPTSUMO-OPTORF2 into a novel arabinose-inducing expression vector pBCM-araM11. pBCM-araM11 was constructed with the arabinose-inducing expression element and pBRCMMCS (SEQ ID NO: 100) disclosed in Taiwan patent application No. 103146225 (filing date: Dec. 30, 2014) and No. 103142753 (filing date: Dec. 9, 2014) by the applicants of the present invention. The construction process of the expression vector is described as follows.

After pARABM11-GFPT was cut with EcoRI and NdeI, the DNA fragment containing araC and araB-M11 expression elements was recovered by using a Gel-M™ gel extraction system kit (GMbiolab, Taiwan). The araC and araB-M11 expression elements were ligated into pBRCMMCS cut with the same restriction enzymes by using T4 DNA ligase. The ligated product was transformed into *E. coli* ECOS 9-5. The transformants were selected by colony polymerase chain reaction and the plasmids were extracted for confirmation of DNA sequence. The plasmid with the correct sequence is named pBCM-araM11, which has SEQ ID NO: 98.

After pET-OPTSUMO-OPTORF2 was cut with NdeI and SalI, the DNA fragment containing OPTSUMO-OPTORF2 was recovered by using a Gel-M™ gel extraction system kit. OPTSUMO-OPTORF2 was ligated into pBCM-araM11 cut with the same restriction enzymes by using T4 DNA ligase. The ligated product was transformed into *E. coli* ECOS 9-5. The transformants were selected by colony polymerase chain reaction and the plasmids were extracted for confirmation of DNA sequencing. The plasmid with the correct sequence is named pBA-OPTSUMO-OPTORF2, which has SEQ ID NO: 46.

The DNA fragment containing the araB-M11 expression element is the arabinose inducing expression element of the present invention, which comprises a promoter (the −16 part is shown as SEQ ID NO: 03) and a T7 phage translation enhancement element (SEQ ID NO: 01), and a ribosome binding site (SEQ ID NO: 02). The arabinose-inducing expression element is as shown in Taiwan Patent Application No. 103146225 (filing date: Dec. 30, 2014), which has of SEQ ID NO: 04.

Summary

In summary, five PCV2 capsid protein expression vectors were prepared in this example, namely: pET-SUMO-ORF2 (SEQ ID NO: 42) and pET-OPTSUMO-ORF2 (SEQ ID. NO: 43), pET-SUMO-OPTORF2 (SEQ ID NO: 44), pET-OPTSUMO-OPTORF2 (SEQ ID NO: 45), and pBA-OPT-SUMO-OPTORF2 (SEQ ID NO: 46). Please refer to FIG. 1.

Example 2 Preparation of PCV2 Capsid Proteins of the Present Invention

As described above, each of the vectors obtained in Example 1 (SEQ ID NOs: 42 to 46) contains the DNA of the capsid protein ORF2 and can be applied to the production of capsid proteins. In addition, for the purpose of purification and solubility performance, the target proteins were fused with the SUMO protein and the His tag. This fusion protein is referred to herein as the SUMO-ORF2 fusion protein, and the fact that the fusion protein contains His tag will not be mentioned again. This Example will use the expression vector described in Example 1 to prepare the SUMO-ORF2 fusion protein of the present invention.

Transformation of *E. coli* and Induced Expression of Recombinant SUMO-ORF2 Fusion Protein (1) Experimental Procedure:

Expression vectors such as pET-SUMO-ORF2, pET-OPT-SUMO-ORF2, pET-SUMO-OPTORF2, and pET-OPT-SUMO-OPTORF2 were transformed into *E. coli* BL21 (DE3) (Yeastern, Taiwan). pET-SUMO-ORF2 was transformed into *E. coli* Rosetta2 (EMD Millipore, USA). pBA-OPTSUMO-OPTORF2 was transformed into *E. coli* BL21 (New England Biolabs, USA). The method of transformation was followed by the operating procedures provided by the manufacturers.

The *E. coli* BL21(DE3) transformant was inoculated into an LB medium containing kanamycin (final concentration: 30 μg/mL) and was shake-cultured at 37° C. and 180 rpm. After overnight incubation, the bacterial solution was inoculated at a ratio of 1:100 into LB medium containing kanamycin (final concentration 30 μg/mL). Shake culture was performed at 37° C. and 180 rpm. Bacteria were cultured to a concentration of approximately 0.4 to 0.6 $OD_{600}$ measured by spectrophotometer, and 0.1 mM isopropyl-β-D-thiogalactoside (IPTG) was added for protein expression induction. After 4 hours of induction, the bacterial fractions were collected by centrifugation (8,000×g, 30 minutes, 4° C.) and the expression of the SUMO-ORF2 fusion protein was observed by protein electrophoresis and Western blot. The primary and secondary antibodies used in Western blot methods were rabbit anti-6×His polyclonal antibody (Protech, Taiwan) and alkaline phosphatase-conjugated goat anti-rabbit IgG (H+L), respectively. The colorant used was NBT/BCIP (Thermo, USA). The soluble and insoluble proteins of the bacteria were also differentiated, and the solubility of the SUMO-ORF2 fusion protein was observed by protein electrophoresis.

The *E. coli* Rosetta2 transformant was inoculated into LB medium containing chloramphenicol (final concentration of 34 μg/mL) and kanamycin (final concentration of 30 μg/mL). The shake-culture was performed at 37° C. and 180 rpm. After overnight incubation, the bacterial solution was inoculated at a ratio of 1:100 into LB medium containing chloramphenicol (final concentration of 34 μg/mL) and kanamycin (final concentration of 30 μg/mL). Shake culture was performed at 37° C. and 180 rpm. Bacteria were cultured to a concentration of approximately 0.4 to 0.6 $OD_{600}$ measured by spectrophotometer, and 0.1 mM IPTG was added for protein expression induction. After 4 hours of induction, the bacterial fractions were collected by centrifugation (8,000×g, 30 minutes, 4° C.) and the expression of the SUMO-ORF2 fusion protein was observed by protein electrophoresis and Western blot. The soluble and insoluble proteins of the bacteria were also differentiated, and the solubility of the SUMO-ORF2 fusion protein was observed by protein electrophoresis.

The *E. coli* BL21 transformant was inoculated into LB medium containing chloramphenicol (25 μg/mL). The shake-culture was performed at 37° C. and 180 rpm. After overnight incubation, the bacterial solution was inoculated at a ratio of 1:100 into LB medium containing chloramphenicol (25 μg/mL). Shake culture was performed at 37° C. and 180 rpm. Bacteria were cultured to a concentration of approximately 0.4 to 0.6 $OD_{600}$ measured by spectrophotometer, and 0.2% arabinose was added for protein expression induction. After 4 hours of induction, the bacterial fractions were collected by centrifugation (8,000×g, 30 minutes, 4° C.) and the expression of the SUMO-ORF2 fusion protein was observed by protein electrophoresis and Western blot. The soluble and insoluble proteins of the bacteria were also differentiated, and the solubility of the SUMO-ORF2 fusion protein was observed by protein electrophoresis.

After the protein electrophoretic film was scanned, the percentage of expression of the recombinant SUMO-ORF2 fusion protein was estimated by using Image Quant TL 7.0 (GE Healthcare Life Sciences, USA) software, and the yield of the fusion protein was further calculated.

Figure 2:
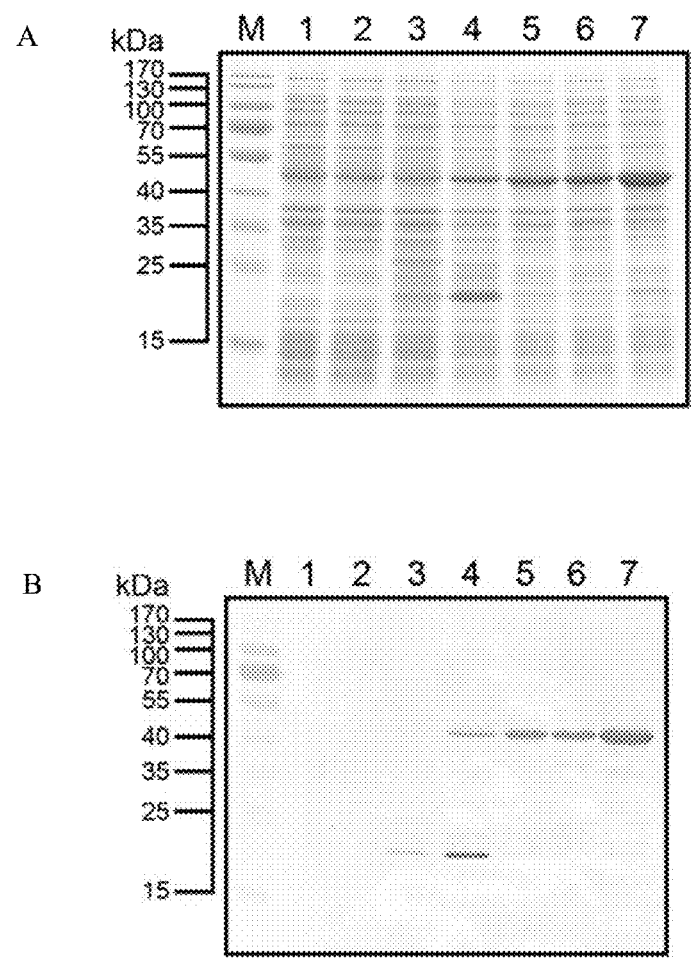

(2) Experimental Results:

The results showed that, in the group of pET-SUMO-ORF2 and pET-OPTSUMO-ORF2 transformed and induced in *E. coli* BL21 (DE3), the recombinant SUMO-ORF2 fusion protein was completely absent (FIG. 2). In the group that the pET-SUMO-ORF2 was transformed and induced in *E. coli* Rosetta2, which is able to produce the corresponding rare codon tRNA, the recombinant SUMO-ORF2 fusion protein can be expressed (FIG. 2) and most of them were soluble (FIG. 3) according to the results. The yield of soluble recombinant SUMO-ORF2 fusion protein is 46.81 mg/L. The fact that the above ORF2 gene cannot be expressed in *E. coli* BL21 (DE3) indicates that the codons carried by ORF2 severely affect the performance of the SUMO-ORF2 fusion protein in *E. coli*.

pET-SUMO-OPTORF2 with the codon-optimized ORF2 gene was transformed into *E. coli* BL21(DE3) and induced. The results showed that the recombinant SUMO-ORF2 fusion protein was successfully expressed (FIG. 2) and was mainly a soluble protein (FIG. 3); the yield of soluble recombinant SUMO-ORF2 fusion protein was 54.62 mg/L. This result shows that after optimizing the ORF2 codon, the performance of the SUMO-ORF2 fusion protein in *E. coli* BL21 (DE3) can be improved.

The pET-OPTSUMO-OPTORF2 expression vector carrying the codon-optimized ORF2 full-length gene and the codon-optimized SUMO gene was transformed into *E. coli* BL21 (DE3) and induced. The results showed that the recombinant SUMO-ORF2 fusion protein can be successfully expressed (FIG. 2), and is mainly a soluble protein (FIG. 3); the yield of the soluble recombinant SUMO-ORF2 fusion protein is 81.66 mg/L. This result shows that after the codon usage of the fusion partner gene is optimized, the performance of the ORF2 fusion protein in *E. coli* can be further improved. Previous studies have never shown that optimizing SUMO gene codons can increase fusion protein expression. The inventors of the present invention have confirmed that the optimization of the SUMO gene codon can increase the production of SUMO-ORF2 fusion protein.

Figure 3:
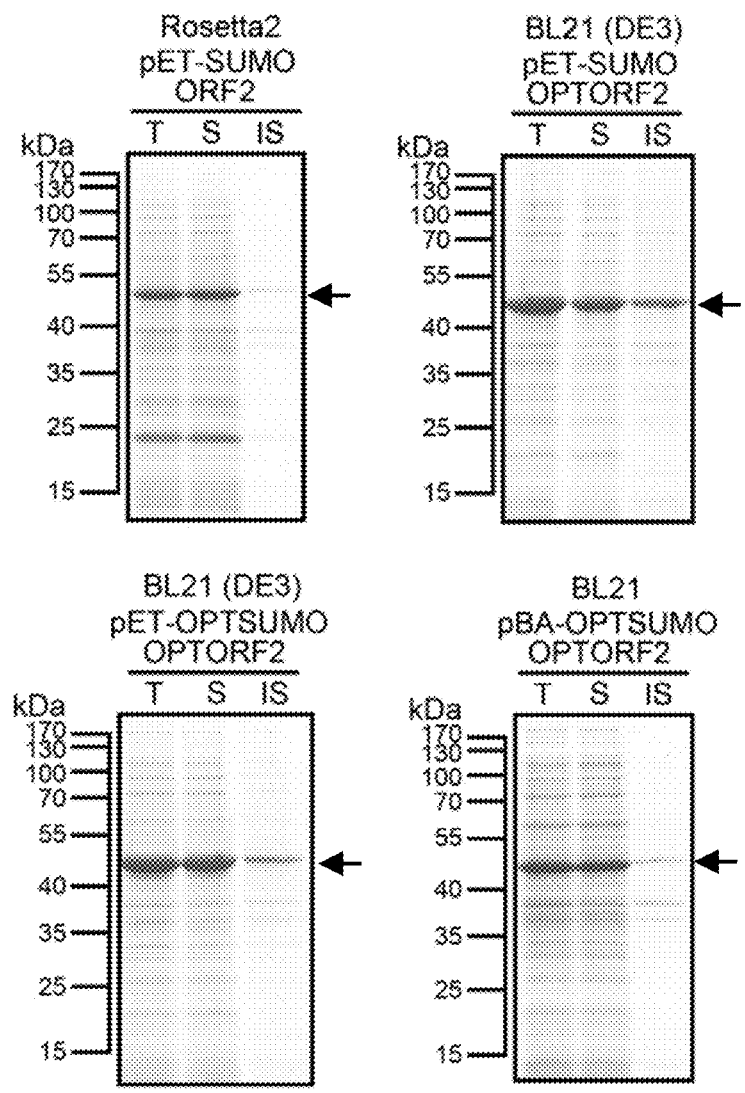

A DNA fragment carrying the downstream sequence-His tag DNA—the codon-optimized SUMO gene—the codon-optimized ORF2 gene was inserted into the arabinose-inducing expression vector pBCM-araM11 and transformed into *E. coli* BL21 for recombinant SUMO-ORF2 fusion protein production. The results show that the recombinant SUMO-ORF2 fusion protein (FIG. 2) can also be produced by using arabinose-inducing expression systems and is mainly a soluble protein (FIG. 3). By using this expression vector for SUMO-ORF2 fusion protein production, the highest yield (103.04 mg/L) could be obtained. Comparing with the highest yield (81.66 mg/L) of the T7 expression system, the yield could be increased by approximately 1.27 times. Each expression vector of Example 1 of the present invention exhibits the yield of the soluble SUMO-ORF2 fusion protein in this experiment as summarized in Table 3 below.

TABLE 3

Yields of soluble SUMO-ORF2 fusion protein.

| Expression Vector | Host-*E. coli* | Yields of Soluble SUMO-ORF2 Fusion Protein (mg/L) |
|---|---|---|
| pET-SUMO-ORF2 | BL21 (DE3) | 0 |
| pET-OPTSUMO-ORF2 | BL21 (DE3) | 0 |
| pET-SUMO-ORF2 | Rosetta2 | 46.81 |
| pET-SUMO-OPTORF2 | BL21 (DE3) | 54.62 |
| pET-OPTSUMO-OPTORF2 | BL21 (DE3) | 81.66 |
| pBA-OPTSUMO-OPTORF2 | BL21 | 103.04 |

Purification of Recombinant SUMO-ORF2 Fusion Protein by Using Immobilized Metal Ion Affinity Chromatography The protein was purified by immobilized metal ion affinity chromatography by taking the advantage of the recombinant SUMO-ORF2 fusion protein's feature of having a His tag at N terminus thereof, which can form a covalent bond with a nickel or cobalt ion. The purification was performed by using a protein liquid chromatography system AKTA prime plus (GE Healthcare, Sweden) with a 5 mL HiTrap™ Ni excel column (GE Healthcare, Sweden).

The pellets were suspended in Lysis buffer (50 mM Tris-HCl, 500 mM NaCl, pH 8.0) and disrupted by an ultrasonic disrupter. The supernatant was collected by centrifugation (8,000×g, 15 minutes). After equilibrating the column with 25 mL Lysis buffer, the disrupted supernatant was injected into the HiTrap™ Ni excel column. After the sample injection was completed, the non-specifically bound proteins were washed with 100 mL washing buffer (50 mM Tris-HCl, 500 mM NaCl, 30 mM imidazole, pH 8.0).

Figure 4:
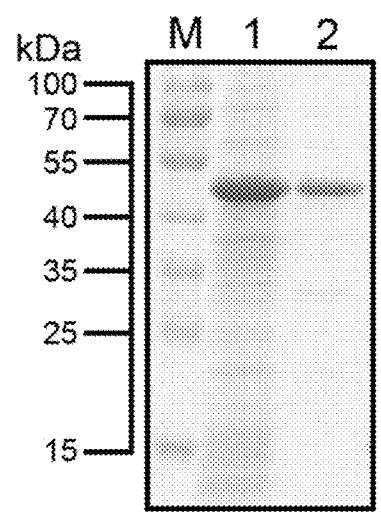

Finally, the recombinant protein on the resin was eluted with 150 mL Elution buffer (50 mM Tris-HCl, 500 mM NaCl, 250 mM imidazole, pH 8.0), which competed with the recombinant protein for binding to the resin binding site with the aid of high concentration of imidazole, resulting in the elution of the recombination SUMO-ORF2 fusion protein from the resin. Protein electrophoresis was used to observe the purification of the recombinant SUMO-ORF2 fusion protein. The experimental results are shown in the FIG. 4.

The SUMO-ORF2 Fusion Protein of the Present Invention is Cut with SUMO Protease

This experiment utilized SUMO protease to cut the ORF2 fusion protein prepared from the *E. coli* expression system. After cutting, SUMO fusion partner fragments with a His tag and capsid protein fragments can be obtained. In this experiment, SUMO protease was produced through an *E. coli* expression system and applied to the applications mentioned above. Those of ordinary skill in the art can also perform this step using SUMO protease obtained in other ways.

(1) Construction of Recombinant SUMO Protease Expression Vector pET-SUMOPH:

The SUMO protease gene was amplified by using *Saccharomyces cerevisiae* genome as the template and SUMOPF (5'-CAATATGGATCCCTTGTTCCTGAAT-TAAATGAAAAAGACG-3'; SEQ ID NO: 47)/SUMOPEN-ZHISR (5'-GATATACTCGAGTTAGTGATGGTGATGGT-GATGACCACTGCCGCTACCTTT TAAAGCGTCGGTTAAAATCAAATG-3; SEQ ID NO: 48) as the primer set. The 50 μL PCR reaction mixture contained 1×GDP-HiFi PCR Buffer B, 200 μM dATP, dTTP, dGTP and dCTP, 1 μM of amplification primers, 200 ng of the genomic DNA of *Saccharomyces cerevisiae*, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the SUMO protease gene amplified from the yeast genome was cut with BamHI and XhoI, the DNA fragment was ligated into pET29a cut with BamHI and SalI by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pET-SUMOPH, which has SEQ ID NO: 49.

(2) Construction of the Recombinant D-SUMO Protease Expression Vector pET-D-SUMOPH:

The D protein gene was amplified by using Lambda phage DNA (Promega, USA) as a template and DF (5'-GATATAG-GTACCATGACGAGCAAAGAAACCTTTACC-3'; SEQ ID NO: 50) and DR (5'-CAATATGGATCCAACGATGCT-GATTGCCGTTC-3; SEQ ID NO: 51) as the primer set. The 50 μL PCR reaction mixture contained 1×GDP-HiFi PCR Buffer B, 200 μM dATP, dTTP, dGTP and dCTP, 1 μM of amplification primers, 100 ng of Lambda phage DNA, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the D protein gene amplified from Lambda phage DNA was cut with KpnI and BamHI, the DNA fragment was ligated into pET29a cut with the same restriction enzymes by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pET-D, which has SEQ ID NO: 99.

After SUMO protease gene amplified from the yeast genome was cut with BamHI and XhoI, the DNA fragment was ligated into pET-D cut with BamHI and SalI by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA is named pET-D-SUMOPH, which has SEQ ID NO: 52.

(3) Induced Expression and Purification of Recombinant Proteases:

Expression vectors of pET-SUMOPH and pET-D-SUMOPH were transformed into *E. coli* BL21(DE3), respectively. The *E. coli* BL21(DE3) transformant was inoculated into an LB medium containing kanamycin (final concentration: 30 μg/mL) and shake-cultured at 37° C. and 180 rpm. After overnight incubation, the bacterial solution was inoculated at a 1:100 ratio into LB medium containing kanamycin (final concentration 30 μg/mL). Shake culture was performed at 37° C. and 180 rpm. Bacteria were cultured to a concentration of approximately 0.4 to 0.6 $OD_{600}$ measured by spectrophotometer, and 0.1 mM IPTG was added for protein expression induction. After 4 hours of induction, the bacterial fractions were collected by centrifugation (8,000× g, 30 minutes, 4° C.) for differentiation of soluble and insoluble proteins. The solubility of the recombinant protease was observed by protein electrophoresis and Western blot. The primary and secondary antibodies used in Western blot methods were rabbit anti-His tag polyclonal antibodies and alkaline phosphatase conjugated goat anti-rabbit antibodies, respectively. The coloring agent used was NBT/BCIP. The purification method of the recombinant protease is the same as the purification method of the recombinant ORF2 fusion protein.

Figure 5:
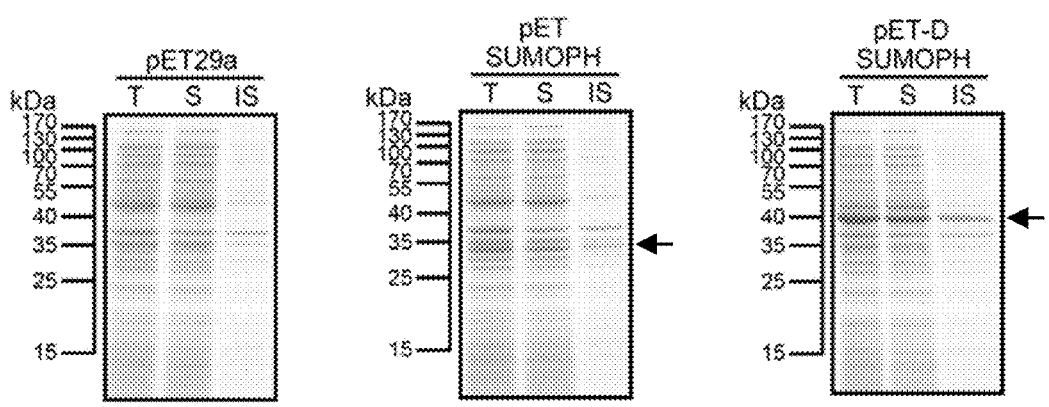
Figure 5:
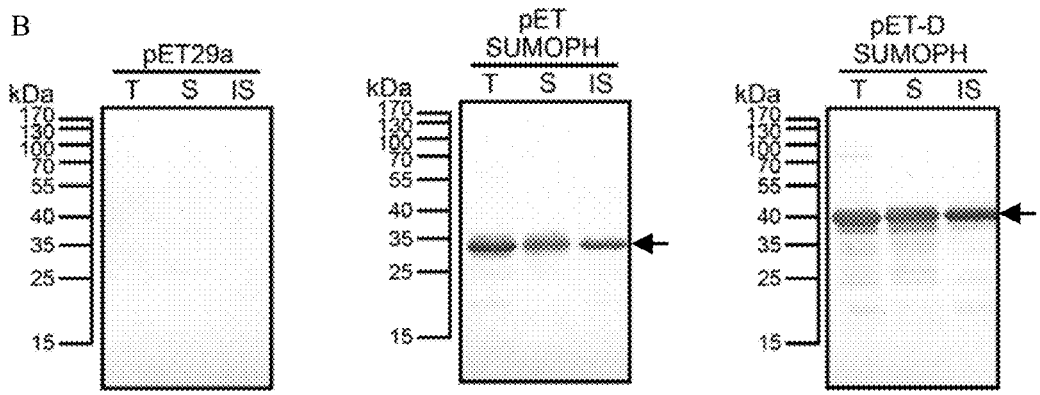

The results showed that both SUMO protease and D-SUMO protease can be expressed in *E. coli* BL21 (DE3) (FIG. 5), with yields of 20.55 mg/L and 46.94 mg/L, respectively, in which the yield of D-SUMO protease was higher. The molar number was about 2.2 times of that of SUMO protease. This result shows that the strategy of fusion expression can increase the expression level of SUMO protease in *E. coli*.

Figure 6:
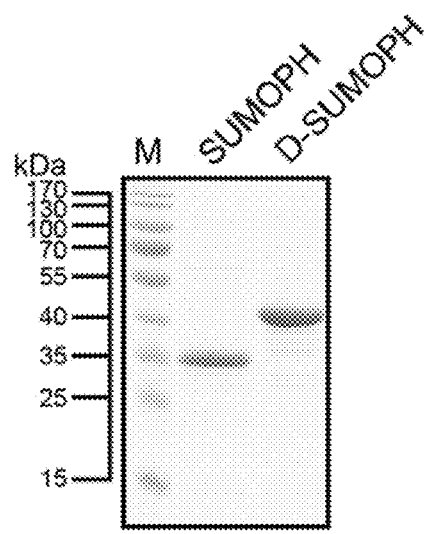

The protein was then purified by immobilized metal ion affinity chromatography taking the advantage of the feature of the recombinant protease of having the His-tag at C-terminus thereof. The results showed that the soluble recombinant SUMO protease and D-SUMO protease could be purified by using the immobilized metal ion affinity column (FIG. 6), in which the purified yield of D-SUMO protease was higher. Twenty-one point five (21.50) mg of protein can be purified from 1 L medium, which is approximately 1.4 times of the purified yield of SUMO protease (15.33 mg).

Figure 7:
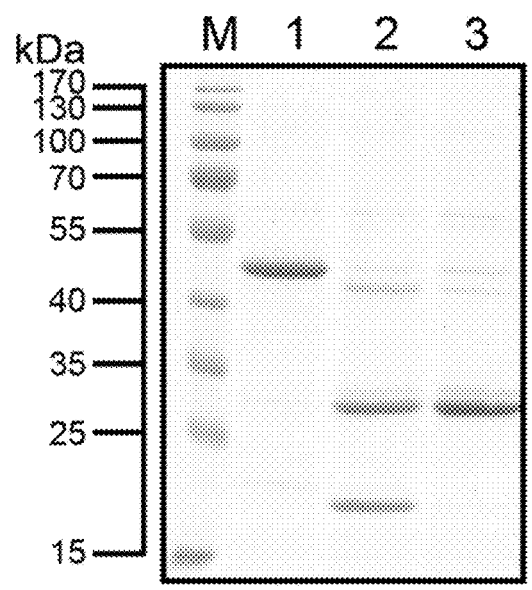

(4) Cutting the Recombinant SUMO-ORF2 Fusion Protein and Observing the Formation of Virus-Like Particles:

The purified recombinant SUMO-ORF2 fusion protein was mixed with a recombinant protease (SUMO protease or D-SUMO protease) at a ratio of 1:0.05 by weight (for example, 1 mg of recombinant ORF2 fusion protein and 0.05 mg of recombinant protease), and the mixture was incubated at 4° C. for 16 hours. The cut protein solution was placed in an Amicon ultra-15 ultracel-100K spin column (Merck Millipore, USA) and centrifuged at 2,600×g at 4° C. to an appropriate volume. After that, the cut protein was filtered by using a 100 kDa regenerated cellulose filter. The results showed that the use of a 100 kDa membrane can effectively remove fusion partners, eliminating the need to use column chromatography to separate ORF2 from its fusion partner, which effectively lower the costs for antigen production (FIG. 7).

Next, the SUMO-ORF2 fusion protein, the protease-cut SUMO-ORF2 fusion protein, and the ORF2 fusion protein obtained by protease cleavage and filtration were respectively placed on a copper grid and left at room temperature for 3 minutes. The excess water was then removed with a filter paper, and uranyl acetate dye was added for negative staining. The staining time was about 40 seconds to 1 minute. The excess dye was then removed with a filter paper, and the virus-like particles were observed with a field emission transmission electron microscope JEM-2100F (JEOL, Japan).

Figure 8:
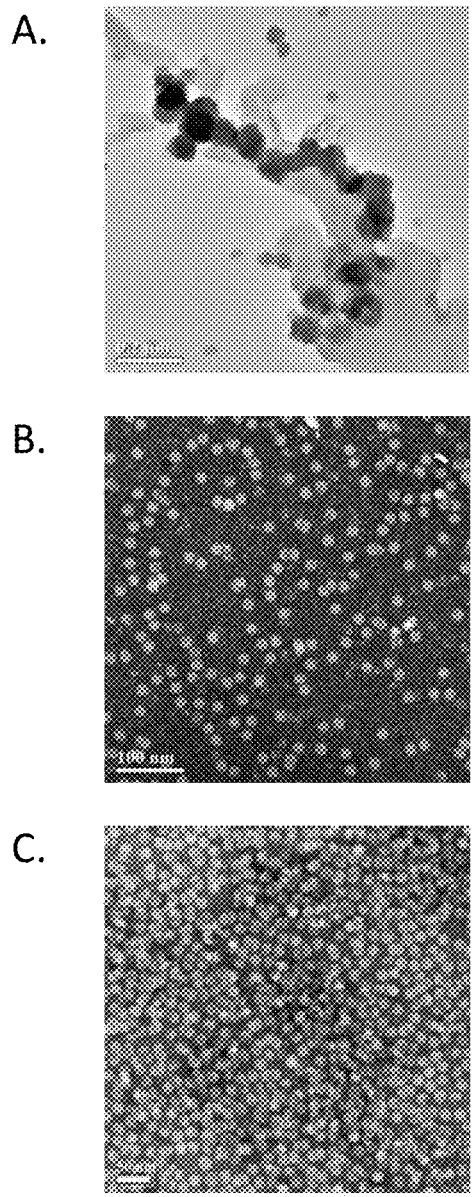

The results showed that the SUMO-ORF2 fusion protein could not form virus-like particles, but the recombinant SUMO-ORF2 fusion protein cut by protease, and the ORF2 fusion protein obtained by cutting with protease and filtered can both form virus-like particles (FIG. 8). The average particle size of the virus-like particles calculated by transmission electron micrographs was approximately 19 nm.

Example 3: Preparation of Porcine Interferon

The present invention discloses that porcine interferon can be used as an adjuvant that is particularly suitable for a subunit vaccine of PCV2. Therefore, the porcine interferon-α and porcine interferon-γ required for the subunit vaccine of the present invention are produced in E. coli host cells in this Example.

Synthesis of Recombinant Porcine Interferon-α (IFN-α) and γ (IFN-γ) Genes (1) Synthesis of IFN-α Gene:

The amino acid sequence of the mature porcine interferon-α-6 was inversely derived as a nucleotide sequence based on a preferred codon for E. coli. Primers were designed based on the nucleotide sequence: OPTIFNA-T1, OPTIFNA-T2, OPTIFNA-T3, OPTIFNA-T4, OPTIFNA-T5, OPTIFNA-T6, OPTIFNA-T7, OPTIFNA-T8, OPTIFNAF, and OPTIFNAR. The sequences are shown in Table 4.

TABLE 4

Primers for synthesis of the codon-optimized porcine interferon-α-6 gene.

| Name | SEQ ID NO | Sequence (5' to 3') |
|---|---|---|
| OPTIFNA-T1 | SEQ ID NO: 53 | TGCGATCTGCCGCAAACCC ACAGTCTGGCTCACACCCG TGCCCTGCGTCTGCTGGCC CAAATGC |
| OPTIFNA-T2 | SEQ ID NO: 54 | CTTCGTGCGGAGAGCCAAA GTCGCGACGATGATCCAGA CAACTGAACGGGGAGATAC GACGCATTTGGGCCAGCAG ACG |
| OPTIFNA-T3 | SEQ ID NO: 55 | ACTTTGGCTCTCCGCACGA AGCATTCGGCGGTAACCAG GTGCAAAAAGCTCAGGCGA TGGCCCTGGT |
| OPTIFNA-T4 | SEQ ID NO: 56 | GCAGTGATTCATCCCATGC GGCCGCGGAGCCTTCCGTA CTGAACAGTTGAAAGGTTT GCTGCAGCATTTCATGAAC CAGGGCCATCGCCTGAG |
| OPTIFNA-T5 | SEQ ID NO: 57 | CCGCATGGGATGAATCACT GCTGCACCAGTTTTGCACC GGTCTGGATCAGCAACTGC GTGACCTGGAAGCATGTGT CATGC |
| OPTIFNA-T6 | SEQ ID NO: 58 | TACGCACCGCCAGAATCGA ATCTTCTTCCAGCAGCGGG GTGCCTTCCAGGCCAGCTT CCTGCATGACACATGCTTC CAGGTCA |
| OPTIFNA-T7 | SEQ ID NO: 59 | ATTCGATTCTGGCGGTGCG TAAATATTTCCATCGCCTG ACGCTGTATCTGCAGGAAA AGAGCTACTCTCCGTGCGC GTGGGAAATCGTTC |
| OPTIFNA-T8 | SEQ ID NO: 60 | TTCCTTTTTACGCAGGCGG TCTTGCAGATTACGGCTTG ACGAGAACGAACGCATCAC TTCGGCGCGAACGATTTCC CACGCGCAC |
| OPTIFNAF | SEQ ID NO: 61 | TGCGATCTGCCGCAAACC |
| OPTIFNAR | SEQ ID NO: 62 | TTCCTTTTTACGCAGGCGG TC |

OPTIFNA-T1 to OPTIFNA-T8 were used as template primers, and OPTIFNAF and OPTIFNAR were used as amplification primers. Overlapping-extension polymerase chain reaction was used to massively amplify the codon-optimized IFN-α gene. The 50 μL PCR reaction mixture contained 1×GDP-HiFi PCR Buffer B, 200 μM dATP, dTTP, dGTP and dCTP, 1 μM of each primer, and 1 U GDP-HiFi DNA Polymerase. The PCR reaction condition was 96° C. for 2 minutes (1 cycle); 94° C. for 30 seconds, 58° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

Cloning of the gene was performed by using the CloneJET PCR Cloning Kit (Thermo, USA), and the ligation mixture was transformed into E. coli ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pJET-IFNA-6, which has SEQ ID NO: 63. After sequence verification, the codon-optimized IFN-α gene has SEQ ID NO: 64.

(2) Synthesis of IFN-γ:

The amino acid sequence of the mature porcine interferon-γ was reversed to a nucleotide sequence based on a preferred codon for *E. coli*. Primers were designed based on the aforementioned nucleotide sequences: OPTIFNR-T1, OPTIFNR-T2, OPTIFNR-T3, OPTIFNR-T4, OPTIFNR-T5, OPTIFNR-T6, OPTIFNR-T7, OPTIFNR-T8, OPTIFNRF, and OPTIFNRR. The sequences are shown in Table 5.

TABLE 5

Primers for synthesis of the codon-optimized porcine interferon-γ gene.

| Name | SEQ ID NO | Sequences (5' to 3') |
|---|---|---|
| OPTIFNR-T1 | SEQ ID NO: 65 | CAAGCCCCGTTTTTCAAAGAAATCACGATCCTGAAAGACTACTTCAATGCGTCAACCTCCGATGTC |
| OPTIFNR-T2 | SEQ ID NO: 66 | TCGCTTTCTTCTTTCCAGTTTTTCAGGATTTCCAGGAACAGCGGACCACCATTCGGGACATCGGAGGTTGACGCATTG |
| OPTIFNR-T3 | SEQ ID NO: 67 | CTGAAAAACTGGAAAGAAGAAAGCGATAAGAAAATTATCCAGAGTCAAATCGTCTCCTTCTACTTCAAATTTTTCG |
| OPTIFNR-T4 | SEQ ID NO: 68 | CATGTCCTGTTTAATAACATCCATACTACGTTGGATCGCCTGATTGTCTTTGAAGATTTCGAAAAATTTGAAGTAGAAGGAGACGA |
| OPTIFNR-T5 | SEQ ID NO: 69 | ACGTAGTATGGATGTTATTAAACAGGACATGTTTCAGCGCTTCCTGAACGGCAGCTCTGGTAAACTGAACGATTTCGAAAAACTGATCAAAATC |
| OPTIFNR-T6 | SEQ ID NO: 70 | CAGTTCTGAGATGGCTTTACGTTGGATCTGCAGGTTGTCCACCGGGATTTTGATCAGTTTTTCGAAATCGTTC |
| OPTIFNR-T7 | SEQ ID NO: 71 | CCAACGTAAAGCCATCTCAGAACTGATCAAAGTTATGAACGATCTGTCGCCGCGCTCCAATCTGCGTAAACG |
| OPTIFNR-T8 | SEQ ID NO: 72 | TTTGCTGGCACGCTGACCCTGGAACATCGTTTGACTACGTTTACGTTTACGCAGATTGGAGCGC |
| OPTIFNRF | SEQ ID NO: 73 | CAAGCCCCGTTTTTCAAAGAA |
| OPTIFNRR | SEQ ID NO: 74 | TTTGCTGGCACGCTGACC |

OPTIFNR-T1 to OPTIFNR-T8 were used as template primers, and OPTIFNRF and OPTIFNRR were used as amplification primers. Overlapping-extension polymerase chain reaction was used to massively amplify the codon-optimized IFN-γ gene. The 50 µL PCR reaction mixture contained 1×GDP-HiFi PCR Buffer B, 200 µM dATP, dTTP, dGTP and dCTP, 1 µM of each primer, and 1 U GDP-HiFi DNA Polymerase. The PCR reaction condition was 96° C. for 2 minutes (1 cycle); 94° C. for 30 seconds, 57° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

Cloning of the gene was performed by using the CloneJET PCR Cloning Kit, and the ligation mixture was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pJET-IFNR, which has SEQ ID NO: 75. After sequence verification, the codon-optimized IFN-γ gene has SEQ ID NO: 76.

Construction of Porcine Interferon-α and γ Expression Vectors (1) Construction of the pET-OPTPIFNAH Expression Vector:

The IFN-α gene was amplified by using the pJET-IFNA-6 plasmid as a template and the PIFNANDEIF (5'-CAATAT-CATATGTGCGATCTGCCGCAAACC-3; SEQ ID NO: 77)/PIFNAHISSALIR (5'-GATATAGTCGACTTATTAGT-GATGGTG ATGGTGATGTTCCTTTTTACGCAGGCG-GTC-3; SEQ ID NO: 78) as the primer set. The 50 µL PCR reaction mixture contained 1×GDP-HiFi PCR Buffer B, 200 µM dATP, dTTP, dGTP and dCTP, 1 µM of amplification primers, 100 ng of pJET-IFNA-6, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with NdeI and SalI, the DNA fragment was ligated into pET29a cut with the same restriction enzymes by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pET-OPTPIFNAH, which has SEQ ID NO: 79.

(2) Construction of the pBA-OPTPIFNAH Expression Vector:

After the PCR-amplified IFN-α gene was cut with NdeI and SalI, the DNA fragments were respectively ligated into pBCM-araM11 cut with the same restriction enzymes by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pBA-OPTPIFNAH, which has SEQ ID NO: 80.

(3) Construction of the pET-SUMO-OPTPIFNAH Expression Vector:

The SUMO gene was amplified by using *Saccharomyces cerevisiae* genome as the template and SUMOF (SEQ ID NO: 25)/SUMOR2 (5'-ACCACCAATCTGTTCTCTGT-GAGC-3; SEQ ID NO: 81) as the primer set. The 50 µL PCR reaction mixture contained 1×GDP-HiFi PCR Buffer B, 200

μM dATP, dTTP, dGTP and dCTP, 1 μM of amplification primers, 200 ng of the genomic DNA of *Saccharomyces cerevisiae*, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The IFN-α gene was amplified by using pJET-IFNA-6 plasmid as the template and SUMOIFNAF (5'-GCTCACA-GAGAACAGATTGGTGGTTGCGATCTGCCG-CAAACC-3; SEQ ID NO: 82)/PIFNAHISSALIR (SEQ ID NO: 78) as the primer set. The 50 μL PCR reaction mixture contained 1×GDP-HiFi PCR Buffer B, 200 μM dATP, dTTP, dGTP and dCTP, 1 μM of amplification primers, 100 ng of pJET-IFNA-6 plasmid, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The SUMO-IFN-α fusion gene was obtained by polymerase chain reaction using the two PCR products obtained above as the template and SUMOF (SEQ ID NO: 25)/PIFNAHISSALIR (SEQ ID NO: 78) as the primer set. The 50 μL PCR reaction mixture contained 1×GDP-HiFi PCR Buffer B, 200 μM dATP, dTTP, dGTP and dCTP, 1 μM of amplification primers, 100 ng of SUMO PCR product, 100 ng of IFN-α PCR product, and 1 U GDP-HiFi DNA Polymerase. The PCR reaction condition was 96° C. for 2 minutes (1 cycle); 94° C. for 30 seconds, 55° C. for 30 seconds, 68° C. for 1 minute (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with KpnI and SalI, the DNA fragment was ligated into pET29a cut with the same restriction enzymes by using T4 DNA ligase. The ligated product was transformed into *E. coli* ECOS 9-5. Transformants were selected by colony polymerase chain reaction. After confirming that the recombinant plasmid in the transformant did carry the inserted DNA by DNA electrophoresis, the plasmids in the transformant were extracted and the DNA was sequenced. The plasmid with the correct DNA sequence is named pET-SUMO-OPTPIFNAH, which has SEQ ID NO: 83.

(4) Construction of the pET-OPTSUMO-OPTPIFNAH Expression Vector:

The OPTSUMO gene was amplified by using pET-OPTSUMO-ORF2 (SEQ ID NO: 43) as the template and OPTSUMOF (SEQ ID NO: 35)/OPTSUMOR2 (5'-GCCGC-CGATTTGTTCACGG-3; SEQ ID NO: 84) as the primer set.

The 50 μL PCR reaction mixture contained 1×GDP-HiFi PCR Buffer B, 200 μM dATP, dTTP, dGTP and dCTP, 1 μM of amplification primers, 100 ng of pET-OPTSUMO-ORF2, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The IFN-α gene was amplified by using pJET-IFNA-6 plasmid (SEQ ID NO: 63) as the template and OPTSU-MOIFNAF (CCGTGAACAAATCGGCGGCTGCGATCT-GCCGCAAACC; SEQ ID NO: 85)/PIFNAHISSALIR (SEQ ID NO: 78) as the primer set. The 50 μL PCR reaction mixture contained 1×GDP-HiFi PCR Buffer B, 200 μM dATP, dTTP, dGTP and dCTP, 1 μM of amplification primers, 100 ng of pJET-IFNA-6, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The OPTSUMO-IFN-α fusion gene was obtained by polymerase chain reaction using the above two PCR products as a template and OPTSUMOF (SEQ ID NO: 35)/PIFNAHISSALIR (SEQ ID NO: 78) as the primer set. The 50 μL PCR reaction mixture contained 1×GDP-HiFi PCR Buffer B, 200 μM dATP, dTTP, dGTP and dCTP, 1 μM of amplification primers, 100 ng of OPTSUMO PCR product, 100 ng of IFN-α PCR product, and 1 U GDP-HiFi DNA Polymerase. The PCR reaction condition was 96° C. for 2 minutes (1 cycle); 94° C. for 30 seconds, 55° C. for 30 seconds, 68° C. for 1 minute (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with KpnI and SalI, the DNA fragment was ligated into pET29a cut with the same restriction enzymes by using T4 DNA ligase. The ligated product was transformed into *E. coli* ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA sequence is named pET-OPTSUMO-OPTPIFNAH, which has SEQ ID NO: 86.

(5) Construction of pBA-OPTSUMO-OPTPIFNAH Expression Vector:

After pET-OPTSUMO-OPTPIFNAH was cut with NdeI and SalI, the DNA fragment containing the OPTSUMO-IFN-α fusion gene was recovered by using a Gel-M™ gel extraction system kit. The DNA fragment was ligated into pBCM-araM11 cut with the same restriction enzymes by using T4 DNA ligase. The ligated product was transformed into *E. coli* ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA sequence is named pBA-OPTSUMO-OPTPIFNAH, which has SEQ ID NO: 87.

(6) Construction of the pET-OPTPIFNRH Expression Vector:

The IFN-γ gene was amplified by using pJET-IFNR plasmid as the template, PIFNRNDEIF (5'-CAATAT-CATATGCAAGCCCCGTTTTTCAAAGAA-3; SEQ ID NO: 88)/PIFNRHISSALIR (5'-GATATAGTCGACTTATT- AGTGATG GTGATGGTGATGTTTGCTGGCACGCT- GACC-3'; SEQ ID NO: 89) as the primer set. The 50 μL PCR reaction mixture contained 1×GDP-HiFi PCR Buffer B, 200 μM dATP, dTTP, dGTP and dCTP, 1 μM of amplification primers, 100 ng of pJET-IFNR plasmid, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with NdeI and SalI, the DNA fragment was ligated into pET29a cut with the same restriction enzymes by using T4 DNA ligase. The ligated product was transformed into E. coli ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA sequence is named pET-OPTPIFNRH, which has SEQ ID NO: 90.

(7) Construction of the pET-SUMO-OPTPIFNRH Expression Vector:

The SUMO gene was amplified by using *Saccharomyces cerevisiae* genome as the template and SUMOF (SEQ ID NO: 25)/SUMOR2 (SEQ ID NO: 81) as the primer set. Amplification conditions and PCR product recovery methods are as described previously.

The IFN-γ gene was amplified by using pJET-IFNR plasmid (SEQ ID NO: 75) as the template and SUMOIFNRF (5'-GCTCACAGAGAACAGATTGGTGGTCAAGC- CCCGTTTTTCAAAGAA-3'; SEQ ID NO: 91)/PIFN- RHISSALIR (SEQ ID NO: 89) as the primer set. The 50 μL PCR reaction mixture contained 1×GDP-HiFi PCR Buffer B, 200 μM dATP, dTTP, dGTP and dCTP, 1 μM of amplification primers, 100 ng of pJET-IFNR plasmid, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The SUMO-IFN-γ fusion gene was obtained by polymerase chain reaction using the two PCR products described above as the templates and using SUMOF (SEQ ID NO: 25)/PIFNRHISSALIR (SEQ ID NO: 89) as the primer set. The 50 μL PCR reaction mixture contained 1×GDP-HiFi PCR Buffer B, 200 μM dATP, dTTP, dGTP and dCTP, 1 μM of amplification primers, 100 ng of SUMO PCR product, 100 ng of IFN-γ PCR product, and 1 U GDP-HiFi DNA Polymerase. The PCR reaction condition was 96° C. for 2 minutes (1 cycle); 94° C. for 30 seconds, 55° C. for 30 seconds, 68° C. for 1 minute (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with KpnI and SalI, the DNA fragment was ligated into pET29a cut with the same restriction enzyme by using T4 DNA ligase. The ligated product was transformed into E. coli ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA sequence is named pET-SUMO-OPTPIFNRH, which has SEQ ID NO: 92.

(8) Construction of the pET-OPTSUMO-OPTPIFNRH Expression Vector:

The OPTSUMO gene was amplified by using pET-OPT- SUMO-ORF2 (SEQ ID NO: 43) as the template and OPT- SUMOF (SEQ ID NO: 35)/OPTSUMOR2 (SEQ ID NO: 84) as the primer set. Amplification conditions and PCR product recovery methods are as described previously.

The porcine interferon-γ gene was amplified by using pJET-IFNR plasmid (SEQ ID NO: 75) as the template and OPTSUMOIFNRF (5'-CCGTGAACAAATCGGCGGC- CAAGCCCCGTTTTTCAAAGAAATC-3'; SEQ ID NO: 93)/PIFNRHISSALIR (SEQ ID NO: 89) as the primer set. The 50 μL PCR reaction mixture contained 1×GDP-HiFi PCR Buffer B, 200 μM dATP, dTTP, dGTP and dCTP, 1 μM of amplification primers, 100 ng of pJET-IFNR plasmid, and 1 U GDP-HiFi DNA Polymerase. The PCR reaction condition was 96° C. for 2 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the Gel-M™ gel extraction system kit.

The OPTSUMO-IFN-γ fusion gene was obtained by polymerase chain reaction using the above two PCR products as the templates and OPTSUMOF (SEQ ID NO: 35)/PIFN- RHISSALIR (SEQ ID NO: 89) as the primer set. The 50 μL PCR reaction mixture contained 1×GDP-HiFi PCR Buffer B, 200 μM dATP, dTTP, dGTP and dCTP, 1 μM of amplification primers, 100 ng of OPTSUMO PCR product, 100 ng of porcine IFN-γ PCR product, and 1 U GDP-HiFi DNA Polymerase. The PCR reaction condition was 96° C. for 2 minutes (1 cycle); 94° C. for 30 seconds, 55° C. for 30 seconds, 68° C. for 1 minute (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the PCR product was cut with KpnI and SalI, the DNA fragment was ligated into pET29a cut with the same restriction enzyme by using T4 DNA ligase. The ligated product was transformed into E. coli ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA plasmid is named pET-OPTSUMO-OPTPIFNRH, which has SEQ ID NO: 94.

(9) Construction of the pBA-OPTSUMO-OPTPIFNRH Expression Vector:

After pET-OPTSUMO-OPTPIFNRH was cut with NdeI and SalI, a DNA fragment containing the OPTSUMO-IFR-γ fusion gene was recovered by using a Gel-M™ gel extraction system kit. The DNA fragment was inserted into pBCM-araM11 cut with the same restriction enzymes by using T4 DNA ligase. The ligated product was transformed into E. coli ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced.

The plasmid with the correct DNA sequence is named pBA-OPTSUMO-OPTPIFNRH, which has SEQ ID NO: 95.

The Expression and Purification of Recombinant Porcine Interferon (1) Expression of Recombinant Porcine Interferon:

pET-OPTPIFNAH (SEQ ID NO: 79), pBA-OPTPIFNAH (SEQ ID NO: 80), pET-SUMO-OPTPIFNAH (SEQ ID NO: 83), pET-OPTSUMO-OPTPIFNAH (SEQ ID NO: 86), and pBA-OPTSUMO-OPTPIFNAH (SEQ ID NO: 87) were transformed into E. coli Shuffle (NEB, USA), respectively. pET-OPTPIFNRH (SEQ ID NO: 90), pET-SUMO-OPTPIF-NHR (SEQ ID NO: 92), pET-OPTSUMO-OPTPIFNRH (SEQ ID NO: 94) and pBA-OPTSUMO-OPTPIFNRH (SEQ ID NO: 95) were transformed into E. coli BL21(DE3), respectively. The transformants were inoculated into LB medium containing kanamycin (final concentration: 30 μg/mL), and shake-culture was performed at 37° C. and 180 rpm. After overnight incubation, the bacterial solution was inoculated in a ratio of 1:100 to LB medium containing a final concentration of 30 μg/mL of conomycin. Shake culture was performed at 37° C. and 180 rpm. Bacteria were cultured to a concentration of approximately 0.4 to 0.6 $OD_{600}$ measured by spectrophotometer, and 0.1 mM IPTG was added for induction of protein expression at 25° C. and 180 rpm. After 4 hours of induction, the bacterial fractions were collected by centrifugation (8,000×g, 30 minutes, 4° C.) and the expression of recombinant porcine interferon was observed by protein electrophoresis. In addition, the soluble and insoluble proteins of the bacteria were also differentiated, and the solubility of recombinant porcine interferon was observed by protein electrophoresis.

Figure 9:
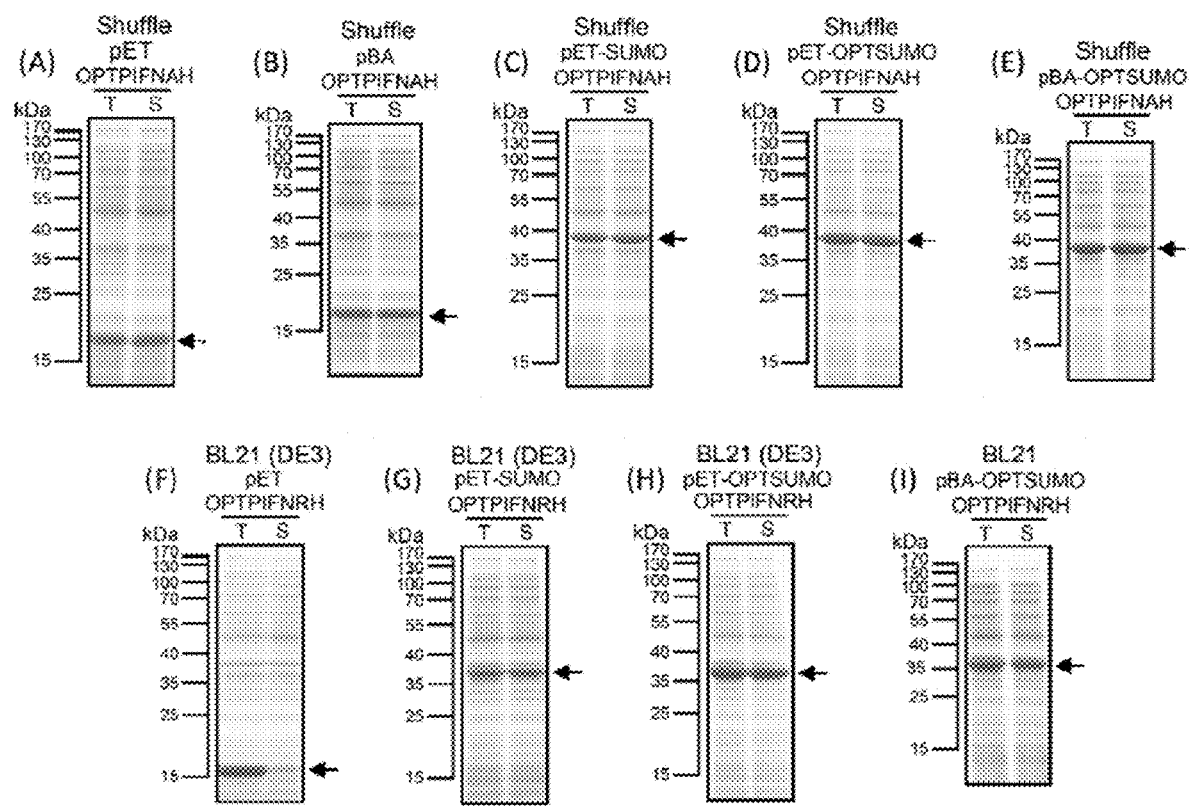

Please refer to the experimental results in FIG. 9 (A to E). The results show that the present invention can successfully produce soluble recombinant porcine IFN-α and SUMO-IFN-α fusion protein by using the E. coli Shuffle host, and the refolding step can be omitted, so as to avoid the problem that the biological activity could be affected by poor refolding efficiency. For expression of the SUMO-IFN-α fusion protein, production of the SUMO-IFN-α fusion protein can be increased by optimizing the SUMO gene codon. The effect of different expression systems on the expression of the SUMO-IFN-α fusion protein showed that the production of SUMO-IFN-α was higher using the mutant arabinose-inducing expression system (155.07 mg/L; FIG. 9(E)). Please refer to the experimental results in FIG. 9 (F to I). The results show that the strategy having SUMO fusion protein can increase the solubility of recombinant porcine IFN-γ. After optimization of the codons of the SUMO gene, the production of SUMO-IFN-γ fusion proteins can be increased. The effect of different expression systems on the expression of SUMO-IFN-γ fusion protein showed that the production of SUMO-IFN-γ by using the T7-inducible expression system and the mutant arabinose-inducible expression system was quite satisfactory.

(2) Construction and Expression of Recombinant SUMO Protease Expression Vector pET-D-SUMOP:

To cleave the SUMO-porcine interferon expressed in the E. coli expression system described in the previous paragraphs to obtain porcine interferon without the SUMO protein fragment, SUMO protease was produced through the E. coli expression system in this experiment. Those of ordinary skill in the art can also perform this step using SUMO protease obtained in other ways.

The SUMO protease gene was amplified by using Saccharomyces cerevisiae genome as the template and SUMPOF (SEQ ID NO: 47)/SUMOPENZR (5'-GATATACTC-GAGTTATTTTAAAGCGTCGGT TAAAATCAAATG-3; SEQ ID NO: 96) as the primer set. The 50 μL PCR reaction mixture contained 1×GDP-HiFi PCR Buffer B, 200 μM dATP, dTTP, dGTP and dCTP, 1 μM of amplification primers, 200 ng of Saccharomyces cerevisiae genome, and 1 U GDP-HiFi DNA Polymerase. The PCR reaction condition was 96° C. for 5 minutes (1 cycle); 94° C. for 30 seconds, 55° C. for 30 seconds, 68° C. for 30 seconds (35 cycles); 68° C. for 5 minutes (1 cycle). After the reaction, agarose gel electrophoresis was used to confirm whether the PCR product contained DNA fragments with predicted size. Next, the PCR product was recovered by using the PCR-M™ Clean Up system kit.

After the SUMO protease gene amplified from the yeast genome was cut with BamHI and XhoI, the DNA fragment was inserted into pET-D cut with BamHI and SalI by using T4 DNA ligase. The ligated product was transformed into E. coli ECOS 9-5. Transformants were selected by colony polymerase chain reaction. After confirming that the recombinant plasmids in the transformant did carry the inserted DNA by DNA electrophoresis, the plasmids in the transformant were extracted and the DNA was sequenced. The plasmid with the correct DNA sequence is named pET-D-SUMOP, which has SEQ ID NO: 97.

pET-D-SUMOP (SEQ ID NO: 97) was transformed into E. coli BL21 (DE3). The E. coli BL21(DE3) was inoculated into LB medium containing kanamycin (final concentration: 30 μg/mL) and shake-cultured at 37° C. and 180 rpm. After overnight incubation, the bacterial solution was inoculated at a 1:100 ratio into LB medium containing kanamycin (final concentration 30 μg/mL). Shake-culture was performed at 37° C. and 180 rpm. Bacteria were cultured to a concentration of approximately 0.4 to 0.6 $OD_{600}$ measured by spectrophotometer, and 0.1 mM IPTG was added for induction of protein expression at 28° C. and 180 rpm. After 4 hours of induction, the bacterial fraction was collected by centrifugation (8,000×g, 30 minutes, 4° C.).

(3) Cleavage and Purification of Recombinant Porcine Interferon:

After induced expression of the transformants carrying the SUMO-porcine interferon fusion protein expression vector and the SUMO protease expression vector, the bacterial fractions were collected by centrifugation (8,000×g, 30 minutes, 4° C.). The collected bacteria were suspended in an appropriate amount of Lysis buffer (20 mM sodium phosphate, 500 mM NaCl, pH 7.4) to have an absorbance of 50 at 600 nm. After disrupting the bacteria by using an ultrasonic processor, the supernatant was collected by centrifugation (8,000×g, 15 minutes, 4° C.). The purified recombinant SUMO-porcine interferon fusion protein and recombinant protease (SUMO protease) were mixed at a weight ratio of 4 and incubated at 4° C. for 16 hours. During this period, the SUMO-porcine interferon fusion protein was cut by SUMO protease into the SUMO protein and porcine interferon with the His-tag at the C-terminus.

Figure 10:
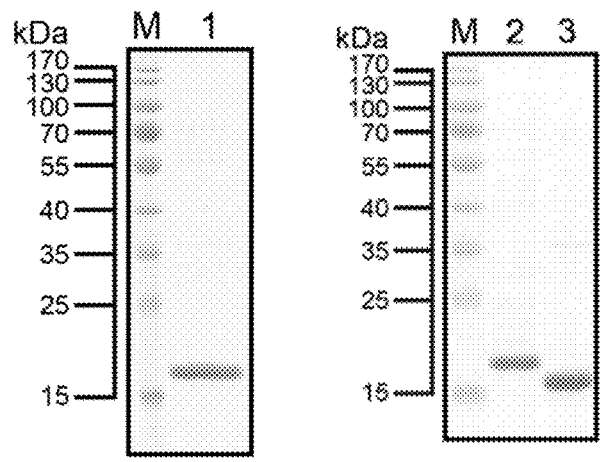

The protein was then purified by using immobilized metal ion affinity chromatography. Purification was performed by using a protein liquid chromatography system AKTA prime plus with a 5 mL HiTrap™ Ni excel column. After equilibrating the column with 25 mL Lysis buffer, the fusion protein cleavage solution was injected into the HiTrap™ Ni excel column. After the sample injection was completed, the non-specifically bound proteins were washed with 100 mL washing buffer (20 mM sodium phosphate, 500 mM NaCl, 30 mM imidazole, pH 7.4). Finally, the recombinant porcine interferon on the resin was eluted with 150 mL Elution buffer (20 mM sodium phosphate, 500 mM NaCl, 250 mM imidazole, pH 7.4) and the purification was observed by protein electrophoresis (as shown in FIG. 10).

Example 4: Preparation and Application of the Present Composition for Preventing PCV2 Infection In this example, the ORF2 encoding protein, the SUMO-ORF2 fusion protein, and the porcine interferon prepared in the foregoing Example 2 and Example 3 were used to prepare a composition for preventing and treating PCV2 infection. In many samples used herein, the composition further comprises MONTANIDE™ ISA 563 VG adjuvant (SEPPIC, France) and/or MONTANIDE™ GEL 01 adjuvant (SEPPIC, France). The components are mixed based on the following experimental design, and then inoculated to piglets to observe the induced immune response or whether there are adverse effects (such as vomiting, trembling, depression, shortness of breath, and swelling of the applied area; if the incidence rate of at least three of the adverse effects is higher than 50%, the safety of the composition is low.)

(1) Experiment 1: Effect of the Content of Porcine Interferon on the Safety of the Present Composition:

Fourteen three-week old field piglets were selected and grouped randomly. They were divided into 7 groups A to G, and the number of piglets in each group was two. One intramuscular injection was performed in each group and the immunization dose was 2 mL. Components of each vaccine are shown in Table 6 below. Observations were made on the day of vaccination and the next day thereof, and the proportion of clinical adverse effects was recorded.

TABLE 6

Experimental design of Experiment 1.

| Group | Vaccine | ORF2 (μg) | IFN-α (μg) | IFN-γ (μg) | Adjuvant (%, v/v) |
|---|---|---|---|---|---|
| A | V-001 | 340 | — | — | GEL 01 (20) |
| B | V-002 | — | 50 | 50 | GEL 01 (20) |
| C | V-003 | 340 | 50 | 50 | GEL 01 (20) |
| D | V-004 | 340 | 25 | 25 | GEL 01 (20) |
| E | V-005 | 340 | 10 | 10 | GEL 01 (20) |
| F | V-006 | 340 | 5 | 5 | GEL 01 (20) |
| G | V-007 | — | — | — | GEL 01 (20) |

The results of the experiment (Table 7) showed that pigs vaccinated with V-001 showed clinical symptoms of depression but no other adverse effects. Pigs vaccinated with V-002 showed symptoms of vomiting and trembling. In addition, the safety of the V-003 sample was more skeptical, and the adverse effects of the V-004, V-005, or V-006 on inoculated pigs were milder. Based on these results, the porcine interferon content will be maintained at 25 μg per dose (2 mL) in the following experiments.

TABLE 7

Experimental results of Experiment 1.

Proportion of Clinical Symptoms (%)

| Vaccine | Vomiting | Trembling | Depression | Shortness of breath | Swelling | Mortality rate |
|---|---|---|---|---|---|---|
| V-001 | 0 | 0 | 100 | 0 | 0 | 0 |
| V-002 | 50 | 50 | 0 | 0 | 0 | 0 |
| V-003 | 100 | 0 | 50 | 50 | 0 | 50 |
| V-004 | 0 | 0 | 50 | 0 | 0 | 0 |
| V-005 | 100 | 0 | 50 | 0 | 0 | 0 |
| V-006 | 50 | 50 | 0 | 0 | 0 | 0 |
| V-007 | 0 | 0 | 0 | 0 | 0 | 0 |

(2) Experiment 2: Effects of the Content of Adjuvant on the Safety of the Present Composition:

Seventy-three three-week-old field piglets were selected and randomly divided into groups A and B. The number of piglets in group A was 38, and that in group B was 35. One intramuscular injection was performed in each group and the immunization dose was 2 mL. The composition of each vaccine is shown in Table 8 below. Observations were made on the day and on the next day of the vaccination, and the proportion of clinical adverse effects was recorded. The experimental results show (Table 9) that the safety of the V-009 sample is high, but the safety of the V-008 sample is also acceptable.

TABLE 8

Experimental Design of Experiment 2.

| Group | Vaccine | ORF2 (μg) | IFN-α (μg) | IFN-γ (μg) | Adjuvant(%) |
|---|---|---|---|---|---|
| A | V-008 | 170 | 25 | 25 | GEL 01 (20) |
| B | V-009 | 170 | 25 | 25 | GEL 01 (10) |

TABLE 9

Experimental Results of Experiment 2.

Proportion of Clinical Symptoms (%)

| Vaccine | Vomiting | Trembling | Depression | Shortness of breath | Swelling | Mortality rate |
|---|---|---|---|---|---|---|
| V-008 | 10.5 | 10.5 | 18.4 | 13.2 | 0 | 10.5 |
| V-009 | 14.3 | 14.3 | 11.4 | 5.7 | 0 | 2.9 |

(3) Experiment 3: Effect of Different Adjuvants on Immune Induction of the Present Composition:

This experiment was conducted in animal husbandry of genetically modified organisms (GMOs) in the Animal Drugs Inspection Branch of the Animal Health Research Institute (AHRI). Eleven 4-week old piglets without being infected by any specific pathogens were grouped randomly and divided into 5 groups A to E. Groups A to D were experimental groups, in which the number of piglets of each group was 2, and group E was the control group, which has 3 piglets. Piglets in groups A to D were immunized intramuscularly at 4th and 6th weeks of age respectively, and the immunization dose was 2 mL. Group E was not immunized. The components of each vaccine are shown in Table 10 below.

TABLE 10

Experimental Design of Experiment 3.

| Group | Vaccine | ORF2 (μg) | IFN-α (μg) | IFN-γ (μg) | Adjuvant (%) |
|---|---|---|---|---|---|
| A | V-009 | 170 | 25 | 25 | GEL 01 (10) |
| B | V-010 | 170 | 25 | 25 | ISA 563 (50) |
| C | V-011 | 67 | 25 | 25 | GEL 01 (10) |
| D | V-012 | 67 | 25 | 25 | ISA 563 (50) |
| E | — | — | — | — | — |

The piglets in each group were challenged with PCV2 at 8th week of age and all were undergone autopsies four weeks after challenge. Serum and plasma samples were collected before immunization (4 weeks of age), after immunization (6 and 8 weeks of age) and after challenge (9, 10, 11 and 12 weeks of age) from the pigs. The titer of anti-PCV2 antibody in serum was determined by using a commercially available ELISA kit (BioCheck, Netherlands). The amount of virus in plasma was determined by using real-time quantitative polymerase chain reaction.

Figure 11:
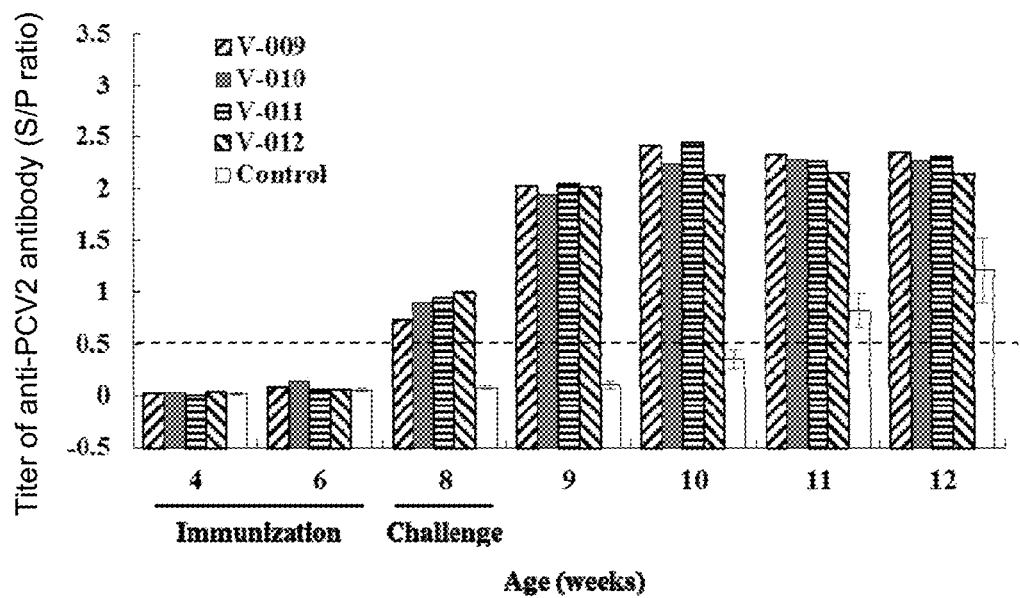
Figure 12:
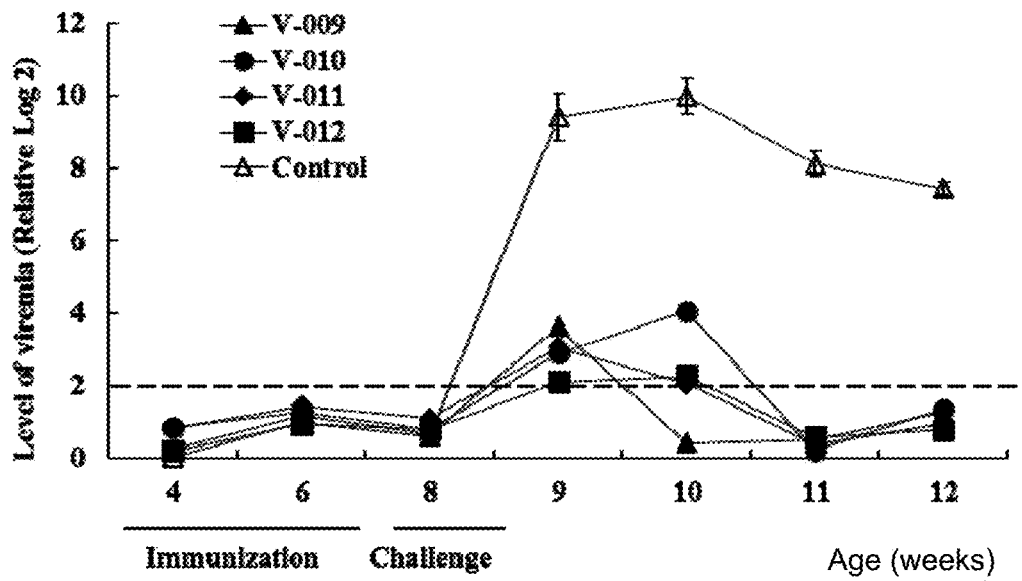

The experimental results showed that V-009, V-010, V-011, and V-012 all induced anti-ORF2 antibody (FIG. 11), and reduced viremia in experimental pigs (FIG. 12). Based on the experimental results, it also shows that each dose (2 mL), which contains 67 μg of ORF2, can produce sufficient immune responses (V-011 and V-012).

(4) Experiment 4: Effects of SUMO-ORF2 Fusion Protein and OFR2 on the Immune Induction of the Present Composition:

This experiment was conducted in animal husbandry of genetically modified organisms (GMOs) in the Animal Drugs Inspection Branch of the Animal Health Research Institute (AHRI). Sixteen 4-week old piglets without being infected by any specific pathogens were grouped randomly and divided into 5 groups A to E. Groups A to D were experimental groups, in which the number of piglets of each group was 3, and group E was the control group, which has 4 piglets. Pigs in groups A to D were immunized intramuscularly at 4 and 6 weeks of age respectively, and the immunization dose was 2 mL. Group E was not immunized. The components of each vaccine are shown in Table 11 below.

TABLE 11

Experimental Design of Experiment 4.

| | | Component/Dosage | | | | |
|---|---|---|---|---|---|---|
| Group | Vaccine | ORF2 (μg) | SUMO-ORF2 (μg) | IFN-α (μg) | IFN-γ (μg) | Adjuvant (%) |
| A | V-013 | 27 | — | 25 | 25 | GEL 01 (10) |
| B | V-014 | 13.5 | — | 25 | 25 | GEL 01 (10) |
| C | V-015 | 6.7 | — | 25 | 25 | GEL 01 (10) |
| D | V-016 | — | 100 | 25 | 25 | GEL 01 (10) |
| E | — | — | — | — | — | — |

The pigs in each group were challenged with PCV2 at 8th week of age, and all were undergone autopsies 5 weeks after challenge. Serum and plasma samples were collected at specific time points. The titer of anti-PCV2 antibody in serum was determined by using a commercially available ELISA kit. The amount of virus in plasma was determined by using real-time quantitative polymerase chain reaction.

Figure 13:
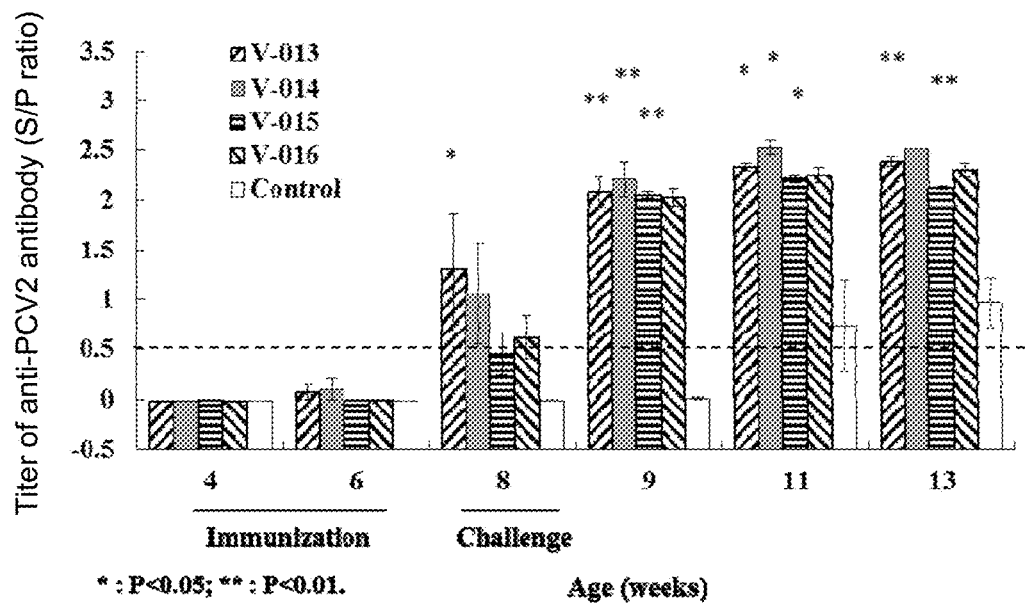
Figure 14:
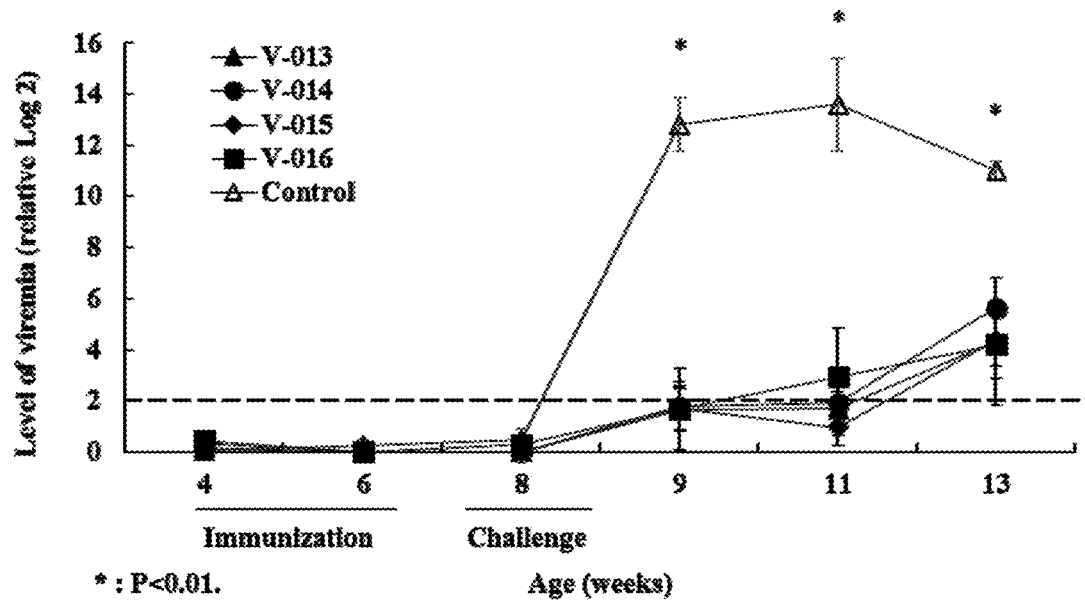
Figure 15:
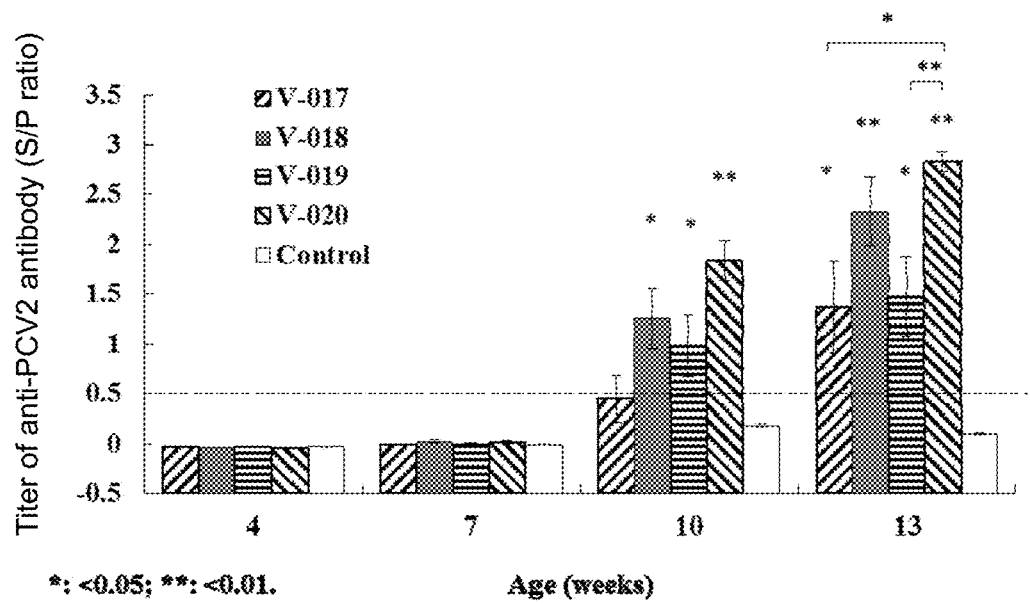

The results showed that each sample could induce pigs to produce anti-PCV2 antibodies, and the best results were obtained with V-013 samples (containing 27 μg of ORF2) (FIG. 13). In addition, all samples reduced viremia in pigs (FIG. 14).

(5) Experiment 5: Effects of Porcine Interferon-α and Porcine Interferon-γ on the Immune Induction of the Present Composition:

This experiment was conducted in a pig farm with low levels of pathogen contamination and without PCV2 infection. Twenty 4-week old SPF piglets without PCV2 infection were selected and randomly divided into 5 groups A to E, in which each group had 4 piglets. Groups A to D were the experimental groups, and group E was the control group. Pigs in groups A to D were immunized intramuscularly at 4th and 7th weeks of age respectively, and the immunization dose was 2 mL. Group E was not immunized. The components of each vaccine are shown in Table 12 below. Serum samples were collected at specific time points. The titer of anti-PCV2 antibody in serum was determined by using a commercially available ELISA kit.

TABLE 12

Experimental Design of Experiment 5.

| | | Component/Dosage | | | |
|---|---|---|---|---|---|
| Group | Vaccine | ORF2 (μg) | IFN-α (μg) | IFN-γ (μg) | Adjuvant (%) |
| A | V-017 | 13 | — | — | GEL 01 (10) |
| B | V-018 | 13 | 25 | — | GEL 01 (10) |
| C | V-019 | 13 | — | 25 | GEL 01 (10) |
| D | V-020 | 13 | 25 | 25 | GEL 01 (10) |
| E | — | — | — | — | — |

The experimental results show that the addition of IFN-α (V-018) or IFN-γ (V-019) alone in the composition of the present invention had an enhanced effect on the induction of immune response. The effect of adding IFN-α is better than adding IFN-γ. On the other hand, addition of both IFN-α and IFN-γ (V-020) in the composition of the present invention induced a better immune response. The results indicate that in the composition of the present invention, IFN-α and IFN-γ have a synergistic effect on immune induction (FIG. 15).

What is claimed is:

1. A composition for preventing porcine circovirus type 2 (PCV2) infection, comprising:
    an effective amount of 2.5 to 250 µg/mL PCV2 capsid protein for inducing a protective immune response;
    2.5 to 25 µg/mL porcine interferon-α;
    2.5 to 25 µg/mL porcine interferon-γ; and
    a pharmaceutically acceptable carrier,
    wherein a combination of the porcine interferon-α and the porcine interferon-γ elicits a synergistic humoral response to the PCV2 capsid protein.

2. The composition of claim 1, comprising:
    3.5 to 170 µg/mL PCV2 capsid protein;
    2.5 to 20 µg/mL porcine interferon-α;
    2.5 to 20 µg/mL porcine interferon-γ; and
    a pharmaceutically acceptable carrier.

3. The composition of claim 2, comprising:
    3.5 to 170 µg/mL PCV2 capsid protein;
    2.5 to 12.5 µg/mL porcine interferon-α;
    2.5 to 12.5 µg/mL porcine interferon-γ; and
    a pharmaceutically acceptable carrier.

4. The composition of claim 1, further comprising pharmaceutically acceptable adjuvant; wherein said pharmaceutically acceptable adjuvant is: MONTANIDE™ ISA 563 VG adjuvant, MONTANIDE™ GEL 01 adjuvant, Freund's complete or incomplete adjuvant, aluminum gel, surfactant, polyanionic polymers, oil emulsions, or a combination thereof.

5. The composition of claim 1, wherein said PCV2 capsid protein, said porcine interferon-α and/or said porcine interferon-γ are manufactured by a method comprising steps:
    (a) obtaining an arabinose-induced expression vector, wherein the arabinose-induced expression vector comprises an expression element and a nucleotide sequence encoding a target protein;
    wherein the expression element comprises:
        a promoter having a −16 site, wherein the −16 site has SEQ ID NO: 03;
        a T7 phage translation enhancing element having SEQ ID NO: 01; and
        a ribosome binding site having SEQ ID NO: 02;
    (b) transforming the arabinose-induced expression vector into an E. coli host and inducing expression of the target protein;
    wherein said target protein is said PCV2 capsid protein, said porcine interferon-α and/or said porcine interferon-γ.

6. The composition of claim 5, wherein said expression element has SEQ ID NO: 04.

7. The composition of claim 5, wherein said arabinose-induce expression vector further comprises a nucleotide sequence encoding a fusion partner, and/or a nucleotide sequence encoding a marker molecule.

8. The composition of claim 5, wherein said arabinose-induce expression vector further comprises a fusion partner; wherein said fusion partner is MsyB of E. coli, YjgD of E. coli, D protein of Lambda phage, SUMO protein of Baker's yeast, or a combination thereof.

9. The composition of claim 5, wherein said arabinose-induce expression vector further comprises a marker molecule; wherein said marker molecule is: His tag, Strep II tag, Flag tag, or a combination thereof.

10. The composition of claim 5, wherein said PCV2 capsid protein is encoded from SEQ ID NO: 09 or SEQ ID NO: 24.

11. The composition of claim 5, wherein said porcine interferon-α is encoded from SEQ ID NO: 64.

12. The composition of claim 5, wherein said porcine interferon-γ is encoded from SEQ ID NO: 76.

13. The composition of claim 5, wherein said PCV2 capsid protein is manufactured by said method and said arabinose-induced expression vector has SEQ ID NO: 46.

14. The composition of claim 5, wherein said porcine interferon-α is manufactured by said method and said arabinose-induced expression vector has SEQ ID NO: 80 or SEQ ID NO: 87.

15. The composition of claim 5, wherein said porcine interferon-γ is manufactured by said method and said arabinose-induced expression vector has SEQ ID NO: 95.

* * * * *